United States Patent [19]

Kirstgen et al.

[11] Patent Number: 5,545,664
[45] Date of Patent: Aug. 13, 1996

[54] SUBSTITUTED PHENOXYMETHYLPHENYL DERIVATIVES, THEIR PREPARATION AND THEIR USE FOR CONTROLLING PESTS AND FUNGI

[75] Inventors: Reinhard Kirstgen, Neustadt; Klaus Oberdorf, Heidelberg; Hubert Sauter; Herbert Bayer, both of Mannheim; Wassilios Grammenos, Ludwigshafen; Harald Rang, Altrip; Volker Harries, Frankenthal; Gisela Lorenz, Hambach; Eberhard Ammermann, Heppenheim, all of Germany

[73] Assignee: BASF Aktiengesellschaft, Ludwigshafen, Germany

[21] Appl. No.: 409,039

[22] Filed: Mar. 23, 1995

[30] Foreign Application Priority Data

Mar. 25, 1994 [DE] Germany ............... 44 10 424.3

[51] Int. Cl.⁶ .................. A01N 37/34; A61K 31/275
[52] U.S. Cl. .................. 514/521; 514/522; 514/539; 558/391; 558/404; 558/414; 560/35; 564/164; 564/165
[58] Field of Search ................ 562/440; 558/391, 558/404, 414; 564/164, 165; 560/35; 514/539, 521, 522

[56] References Cited

U.S. PATENT DOCUMENTS

| | | | |
|---|---|---|---|
| 5,166,399 | 11/1992 | Schuetz et al. | 560/35 |
| 5,298,527 | 3/1994 | Grammenos et al. | 514/539 |
| 5,358,968 | 10/1994 | Oberdorf et al. | 514/620 |

FOREIGN PATENT DOCUMENTS

| | | |
|---|---|---|
| 386561 | 9/1990 | European Pat. Off. . |
| 398692 | 11/1990 | European Pat. Off. . |
| 513580 | 11/1992 | European Pat. Off. . |
| 579124 | 1/1994 | European Pat. Off. . |

*Primary Examiner*—Johann Richter
*Attorney, Agent, or Firm*—Keil & Weinkauf

[57] ABSTRACT

Substituted phenoxymethylphenyl derivatives I

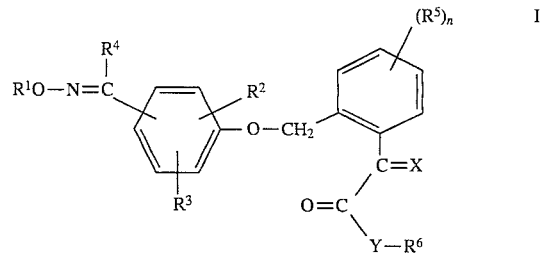

$X$ is $=CH-OCH_3$, $=C-CH_3$ or $=N-OCH_3$;
$R^1$ is, inter alia,
$R^2$ and $R^3$ are, inter alia,
H, halogen, CN, $NO_2$, $C_1-C_4$-alkyl, $C_1-C_2$-haloalkyl, $C_1-C_4$-alkoxy or $C_1-C_2$-haloalkoxy;
$R^4$ is, inter alia,
CN, Cl, Br, $C_1-C_6$-alkoxy, $C_1-C_6$-alkylthio or $C_1-C_4$-haloalkoxy;
$R^5$ is, inter alia,
$NO_2$, CN, halogen, $C_1-C_4$-alkyl, $C_1-C_4$-haloalkyl, $C_1-C_4$-alkoxy or $C_1-C_4$-haloalkoxy;
n is 0–4; Y is —O—, —NH—, —N(CH₃)—; $R^6$ is H, $C_1-C_4$-alkyl.
The compounds are useful for controlling pests and fungi.

20 Claims, No Drawings

SUBSTITUTED PHENOXYMETHYLPHENYL DERIVATIVES, THEIR PREPARATION AND THEIR USE FOR CONTROLLING PESTS AND FUNGI

The present invention relates to novel substituted phenoxymethylphenyl derivatives of the formula I

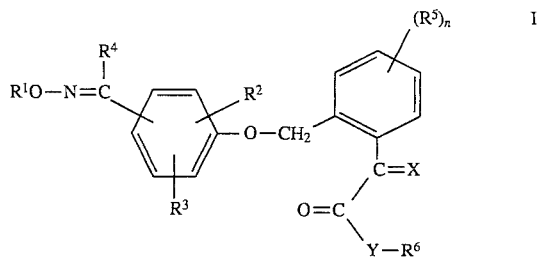

where the variables have the following meanings:

X is =CH—OCH$_3$, =CH—CH$_3$ or =N—OCH$_3$;

R$^1$ is

C$_1$–C$_6$-alkyl, C$_2$–C$_6$-alkenyl, C$_3$–C$_6$-alkynyl, C$_1$–C$_6$-haloalkyl, C$_3$–C$_6$-haloalkenyl, C$_1$–C$_4$-alkoxy-C$_1$–C$_6$-alkyl, cyano-C$_1$–C$_6$-alkyl, C$_1$–C$_6$-alkoxycarbonyl-C$_1$–C$_6$-alkyl, a C$_3$–C$_6$-cycloalkyl or C$_3$–C$_6$-cycloalkyl-C$_1$–C$_4$-alkyl group, an aryl-C$_1$–C$_6$-alkyl or aryl-C$_3$–C$_6$-alkenyl or aryloxy-C$_1$–C$_6$-alkyl group, a saturated or unsaturated 4- to 6-membered heterocyclyl or heterocyclyl-C$_1$–C$_4$-alkyl group or a heteroaryl-C$_1$–C$_6$-alkyl group, the heterocyclic rings in addition to C atoms in each case containing one or two ring members which are selected from the group consisting of an oxygen or sulfur atom and one or two nitrogen atoms and one or two groups —N(CH$_3$)—, it being possible for the carbocyclic and heterocyclic rings in each case in turn to carry one or more radicals selected from the group consisting of: halogen, C$_1$–C$_4$-alkyl, C$_1$–C$_2$-haloalkyl, C$_3$–C$_6$-cycloalkyl, C$_1$–C$_4$-alkoxy, C$_1$–C$_2$-haloalkoxy, halogen, aryl and aryloxy;

R$^2$ and R$^3$ are hydrogen, halogen, cyano, nitro, C$_1$–C$_4$-alkyl, C$_1$–C$_2$-haloalkyl, C$_1$–C$_4$-alkoxy, C$_1$–C$_2$-haloalkoxy, or, if R$^2$ and R$^3$ are adjacent, together are an oxymethylidenoxy or oxyethylidenoxy bridge, it being possible for each C atom of these bridges if desired to carry one or two halogen atoms and/or methyl radicals;

R$^4$ is cyano, chlorine, bromine, C$_1$–C$_6$-alkoxy, C$_1$–C$_6$-alkylthio, C$_1$–C$_4$-haloalkoxy, C$_1$–C$_4$-alkoxy-C$_1$–C$_4$-alkoxy, C$_3$–C$_6$-cycloalkyl-C$_1$–C$_2$-alkoxy, C$_1$–C$_6$-alkylamino, di-(C$_1$–C$_6$-alkyl)amino, C$_3$–C$_6$-alkenyloxy, C$_3$–C$_6$-alkynyloxy, aryloxy, arylthio, it being possible for the aromatic rings to carry one to three radicals selected from the group consisting of C$_1$–C$_4$-alkyl, C$_1$–C$_4$-haloalkyl, C$_1$–C$_4$-alkoxy, C$_1$–C$_4$-haloalkoxy and C$_1$–C$_4$-alkylthio, and it being possible for the aromatic rings additionally to carry sufficient halogen atoms such that the total number of radicals is 4 or 5;

R$^5$ is nitro, cyano, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, phenyl or phenoxy, it being possible for the aromatic rings to carry one to three radicals selected from the group consisting of C$_1$–C$_4$-alkyl, C$_1$–C$_4$-haloalkyl, C$_1$–C$_4$-alkoxy, C$_1$–C$_4$-haloalkoxy and C$_1$–C$_4$-alkylthio, and it being possible for the aromatic rings additionally to carry sufficient halogen atoms such that the total number of radicals is 4 or 5;

or, if n is 2, 3, or 4, is a 1,3-butadiene-1,4-diyl group or a mono- or dihalogenated 1,3-butadiene-1,4-diyl group fused to two adjacent C atoms of the parent substance, it being possible for these fused rings in turn to carry one or two radicals selected from the group consisting of nitro, cyano, halogen, C$_1$–C$_4$-haloalkyl, C$_1$–C$_4$-alkoxy, C$_1$–C$_4$-haloalkoxy and C$_1$–C$_4$-alkylthio;

n is 0, 1, 2, 3 or 4, it being possible for the radicals R$^5$ to be identical or different if n is 2, 3 or 4;

Y is oxygen, —NH— or —N(CH$_3$)—;

R$^6$ is hydrogen or C$_1$–C$_4$-alkyl.

The invention additionally relates to processes and intermediates for preparing the compounds I, their use as fungicides and for controlling pests, fungicidal compositions and compositions for controlling pests which contain these compounds as active substances, and processes for controlling harmful fungi and pests. Compounds of the phenoxymethylphenyl derivatives I type have already been disclosed in the following publications:

EP-A 386 561 describes [(iminoalkyl)phenoxymethyl]phenylacetic ester derivatives of the formula I' having fungicidal and pesticidal properties

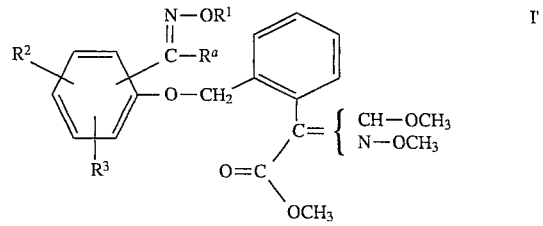

R$^a$ being hydrogen, alkyl or aryl.

In addition, it can be inferred from EP-A 579 124 that 2-[(iminoalkyl)phenoxymethyl]phenylacetamides of the formula I"

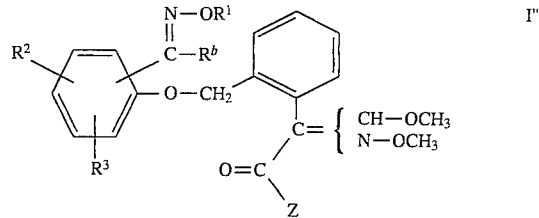

R$^b$ being hydrogen, alkyl, cycloalkyl, haloalkyl or aryl and Z being amino, alkylamino or dialkylamino, are suitable for controlling fungi and pests. Compounds in which Z is alkoxy are additionally considered suitable for controlling pests.

EP-A 513 580 discloses that α-phenylacrylic acid derivatives which in common have a certain basic structure are fungicidally and pesticidally active. On suitable choice of the individual substituents, compounds of the formula I'''

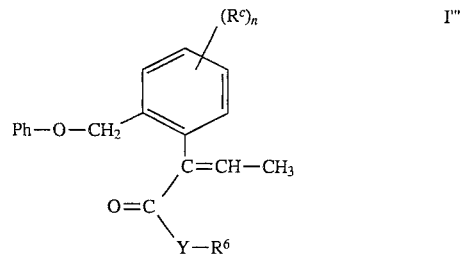

can be constructed, where

R$^c$ is hydrogen, nitro, cyano, halogen, C$_1$–C$_4$-alkyl, C$_1$–C$_4$-alkoxy, C$_1$–C$_4$-haloalkyl, C$_1$–C$_4$-haloalkoxy or C$_1$–C$_4$-alkylthio, or, in the case where n is 2, 3 or 4, two adjacent substituents R$^c$ together form an unsubstituted or substituted 1,3-butadiene-1,4-diyl group, and where Ph is a phenyl ring which, in addition to various other substituents, inter alia can carry a group —C(Rd)=NOR$^6$, where R$^d$ is hydrogen, C$_1$–C$_6$-alkyl or unsubstituted or substituted aryl and R$^e$ is unsubstituted or substituted C$_1$–C$_6$-alkyl, C$_2$–C$_6$-alkenyl or C$_2$–C$_6$-alkynyl, or is a 5- or 6-membered aromatic or heteroaromatic system.

Compounds of this type, but having at most one radical R$^c$ which, on the phenyl radical Ph, in addition to the group —C(Rd)=NOR$^e$, can additionally carry one or two cyano, halogen, C$_1$–C$_4$-alkyl, C$_1$–C$_4$-haloalkyl and/or C$_1$–C$_4$-alkoxy substituents, are emphasized in EP-A 513 580 as preferred fungicides under the formula Ib.

Finally, EP-A 398 692 discloses, inter alia, substituted 2-[2-(phenoxymethyl)phenyl]-2-alkoxyiminoacetamides having fungicidal properties.

However, the fungicidal or insecticidal actions of the known compounds may only be satisfactory to a limited extent, particularly at low application rates and concentrations.

It is an object of the present invention to make available novel compounds having improved fungicidal and/or pesticidal properties.

We have found that this object is achieved by the substituted phenoxymethylphenyl derivatives I defined at the outset. We have furthermore found processes and intermediates for preparing these compounds, compositions containing them, and methods for their use for controlling harmful fungi and pests.

The meanings listed above for the substituents R$^1$ to R$^6$ are collective terms for individual lists of the separate group members. All carbon atoms, ie. all alkyl, alkenyl, alkynyl, haloalkyl, haloalkenyl, alkoxy, haloalkoxy, alkenyloxy, alkynyloxy, alkoxycarbonyl, alkylthio and alkylamino moieties can be straight-chain or branched. Halogenated substituents preferably carry one to five identical or different halogen atoms.

Specific examples are:

—halogen: fluorine, chlorine, bromine or iodine, preferably fluorine or chlorine;

—C$_1$–C$_4$-alkyl: methyl, ethyl, n-propyl, 1-methylethyl, n-butyl, 1-methylpropyl, 2-methylpropyl, 1,1-dimethylethyl, preferably methyl;

—C$_1$–C$_6$-alkyl: C$_1$–C$_4$-alkyl as mentioned above, and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, preferably methyl, ethyl, n-propyl, 1-methylethyl, n-butyl or 1,1-dimethylethyl;

—C$_2$–C$_6$-alkenyl: ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethyl-prop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methylprop-1-en-1-yl, 1-ethyl-2-methylprop-2-en-1-yl, preferably ethenyl or prop-2-en-1-yl;

—C$_3$–C$_6$-alkynyl: prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl, 4-methylpent-2-yn-5-yl, preferably prop-2-yn-1-yl;

—C$_1$–C$_2$-haloalkyl: eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, preferably difluoromethyl or trifluoromethyl;

—C$_1$–C$_6$-haloalkyl: C$_1$–C$_6$-alkyl as mentioned above, which is partially or completely substituted by fluorine, chlorine and/or bromine, that is eg. the abovementioned C$_1$–C$_2$-haloalkyl radicals, and also 3-chloropropyl or heptafluoropropyl, preferably trifluoromethyl, pentafluoroethyl or heptafluoropropyl;

—C$_3$–C$_6$-haloalkenyl: C$_3$–C$_6$-alkenyl as mentioned above, which is partially or completely substituted by fluorine, chlorine and/or bromine, that is eg. 2-chloroallyl, 3-chloroallyl or 3,3-dichloroallyl;

—C$_1$–C$_4$-alkoxy: methoxy, ethoxy, n-propoxy, 1-methylethoxy, n-butoxy, 1-methylpropoxy, 2-methylpropoxy, 1,1-dimethylethoxy, preferably methoxy or ethoxy;

—C$_1$–C$_6$-alkoxy: C$_1$–C$_4$-alkoxy as mentioned above, and also n-pentoxy, 1-methylbutoxy, 2-methylbutoxy, 3-methylbutoxy, 2,2-dimethylpropoxy, 1-ethylpropoxy, n-hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, preferably $C_1$–$C_4$-alkoxy as mentioned above;

—$C_1$–$C_4$-haloalkoxy: $C_1$–$C_4$-alkoxy as mentioned above, which is partially or completely substituted by fluorine, chlorine and/or bromine, that is eg. chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 3-chloropropoxy, preferably difluoromethoxy, trifluoromethoxy, 2,2,2-trifluoroethoxy or pentafluoroethoxy;

—$C_1$–$C_6$-alkoxycarbonyl in the substituent $C_1$–$C_6$-alkoxycarbonyl-$C_1$–$C_6$-alkyl: methoxycarbonyl, ethoxycarbonyl, n-propoxycarbonyl, 1-methylethoxycarbonyl, n-butoxycarbonyl, 1-methylpropoxycarbonyl, 2-methylpropoxycarbonyl, and 1,1-dimethylethoxycarbonyl, n-pentoxycarbonyl, 1-methylbutoxycarbonyl, 2-methylbutoxycarbonyl, 3-methylbutoxycarbonyl, 2,2-dimethylpropoxycarbonyl, 1-ethylpropoxycarbonyl, n-hexoxycarbonyl, 1,1-dimethylpropoxycarbonyl, 1,2-dimethylpropoxycarbonyl, 1-methylpentoxycarbonyl, 2-methylpentoxycarbonyl, 3-methylpentoxycarbonyl, 4-methylpentoxycarbonyl, 1,1-dimethylbutoxycarbonyl, 1,2-dimethylbutoxycarbonyl, 1,3-dimethylbutoxycarbonyl, 2,2-dimethylbutoxycarbonyl, 2,3-dimethylbutoxycarbonyl, 3,3-dimethylbutoxycarbonyl, 1-ethylbutoxycarbonyl, 2-ethylbutoxycarbonyl, 1,1,2-trimethylpropoxycarbonyl, 1,2,2-trimethylpropoxycarbonyl, 1-ethyl-1-methylpropoxycarbonyl, 1-ethyl-2-methylpropoxycarbonyl, preferably $C_1$–$C_4$-alkoxycarbonyl; examples of $C_1$–$C_6$-alkoxycarbonyl-$C_1$–$C_6$-alkyl are ethoxycarbonylmethyl, tert-butoxycarbonylmethyl and tert-butoxycarbonylpropyl;

—$C_3$–$C_6$-cycloalkyl: cyclopropyl, cyclobutyl, cyclopentyl, cyclohexyl, preferably cyclopropyl, cylopentyl or cyclohexyl;

—$C_3$–$C_6$-cycloalkyl-$C_1$–$C_4$-alkyl: eg. cyclopropylmethyl, cyclobutylmethyl, cyclopentylmethyl, cyclohexylmethyl, 2-(cyclopropyl)ethyl, 2-(cyclobutyl)ethyl, 2-(cyclopentyl)ethyl, 2-(cyclohexyl)ethyl, 3-(cyclopropyl)propyl, 3-(cyclobutyl)propyl, 3-(cyclopentyl)propyl, 3-(cyclohexyl)propyl, 4-(cyclopropyl)butyl, 4-(cyclobutyl)butyl, 4-(cyclopentyl)butyl, 4-(cyclohexyl)butyl, preferably cyclopropylmethyl or cyclopentylmethyl;

—cyano-$C_1$–$C_6$-alkyl: eg. cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, 2-cyanomethylprop-2-yl, preferably cyanomethyl;

—aryl-$C_1$–$C_6$-alkyl: arylmethyl, 1-arylethyl, 2-arylethyl, 1-arylprop-1-yl, 2-arylprop-1-yl, 3-arylprop-1-yl, 1-arylbut-1-yl, 2-arylbut-1-yl, 3-arylbut-1-yl, 4-arylbut-1-yl, 1-arylbut-2-yl, 2-arylbut-2-yl, 3-arylbut-2-yl, 3-arylbut-2-yl, 4-arylbut-2-yl, 1-(arylmethyl)eth-1-yl, 1-(arylmethyl)-1-(methyl)eth-1-yl, 1-(arylmethyl)prop-1-yl, preferably arylmethyl or 1-arylethyl;

—heteroaryl-$C_1$–$C_6$-alkyl: heteroarylmethyl, 1-(heteroaryl)ethyl, 2-(heteroaryl)ethyl, 1-(heteroaryl)prop-1-yl, 2-(heteroaryl)prop-1-yl, 3-(heteroaryl)prop-1-yl, 1-(heteroaryl)but-1-yl, 2-(heteroaryl)but-1-yl, 3-(heteroaryl)but-1-yl, 4-(heteroaryl)but-1-yl, 1-(heteroaryl)but-2-yl, 2-(heteroaryl)but-2-yl, 3-(heteroaryl)but-2-yl, 3-(heteroaryl)but-2-yl, 4-(heteroaryl)but-2-yl, 1-(heteroarylmethyl)eth-1-yl, 1-(heteroarylmethyl)-1-(methyl)eth-1-yl, 1-(heteroarylmethyl)prop-1-yl, preferably heteroarylmethyl;

—$C_1$–$C_4$-alkylthio: methylthio, ethylthio, n-propylthio, 1-methylethylthio, n-butylthio, 1-methylpropylthio, 2-methylpropylthio, 1,1-dimethylethylthio, preferably methylthio or ethylthio;

—$C_1$–$C_6$-alkylthio: $C_1$–$C_4$-alkylthio as mentioned above, and also n-pentylthio, 1-methylbutylthio, 2-methylbutylthio, 3-methylbutylthio, 2,2-dimethylpropylthio, 1-ethylpropylthio, n-hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio, 1-ethyl-2-methylpropylthio, preferably $C_1$–$C_4$-alkylthio as mentioned above;

—$C_1$–$C_4$-alkoxy-$C_1$–$C_6$-alkyl: methoxymethyl, ethoxymethyl, n-propoxymethyl, (1-methylethoxy)methyl, n-butoxymethyl, (1-methylpropoxy)methyl, (2-methylpropoxy)methyl, (1,1-dimethylethoxy)methyl, 2-methoxyethyl, 2-ethoxyethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 3-(methoxy)propyl, 2-(ethoxy)propyl, 3-(ethoxy)propyl, 3-propoxypropyl, 3-butoxypropyl, 4-(methoxy)butyl, 4-(ethoxy)butyl, 4-(n-propoxy)butyl, 4-(n-butoxy)butyl, 5-(methoxy)pentyl, 5-(ethoxy)pentyl, 5-(n-propoxy)pentyl, 5-(n-butoxy)pentyl, 6-(methoxy)hexyl, 6-(ethoxy)hexyl, 6-(n-propoxy)hexyl, 6-(n-butoxy)hexyl, preferably methoxymethyl, ethoxymethyl, (1,1-dimethylethoxy)methyl or 2-methoxyethyl;

—$C_1$–$C_6$-alkylamino: methylamino, ethylamino, n-propylamino, 1-methylethylamino, n-butylamino, 1-methylpropylamino, 2-methylpropylamino, 1,1-dimethylethylamino, n-pentylamino, 1-methylbutylamino, 2-methylbutylamino, 3-methylbutylamino, 2,2-dimethylpropylamino, 1-ethylpropylamino, n-hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino, 1-ethyl-2-methylpropylamino, preferably $C_1$–$C_4$-alkylamino such as methylamino, ethylamino, n-propylamino and n-butylamino;

—di-($C_1$–$C_6$)-alkylamino: eg. N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methyl-ethyl)amino, N-butyl-N-ethylamino, N-ethyl-N-(1-methyl-propyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1

-methylethyl)-N-(1-methylpropyl)amino, N-(1 -methylethyl)-N-(2-methylpropyl)amino, N-(1,1 -dimethylethyl)-N-(1-methylethyl)amino, N-butyl-N-(1-methylpropyl)amino, N-butyl-N-(2-methylpropyl)amino, N-butyl-N-( 1,1-dimethylethyl)amino, N-(1-methylpropyl)-N-(2-methylpropyl)amino, N-(1,1-dimethylethyl)-N-(1-methylpropyl)amino, N-(1,1-dimethylethyl)-N-(2-methylpropyl)amino, preferably di-($C_1$–$C_4$)-alkylamino such as N,N-dimethylamino and N,N-diethylamino;

—$C_3$–$C_6$-alkenyloxy: prop-2-en-1-yloxy, n-buten-2-yloxy, n-buten-3-yloxy, 1-methylprop-2-en-1-yloxy, 2 -methylprop-2-en-1-yloxy, n-penten-2-yloxy, n-penten-3-yloxy, n-penten-4-yloxy, 1-methylbut-2-en-1-yloxy, 2 -methylbut-2-en-1-yloxy, 3-methylbut-2-en-1-yloxy, 1 -methylbut-3-en-1-yloxy, 2-methylbut-3-en-1-yloxy, 3 -methylbut-3-en-1-yloxy, 1,1-dimethylprop-2-en-1-yloxy, 1,2 -dimethylprop-2-en-1-yloxy, 1-ethylprop-2-en-1-yloxy, n-hex-2-en-1-yloxy, n-hex-3-en-1-yloxy, n-hex-4-en-1-yloxy, n-hex-5-en-1-yloxy, 3-methylpent-1-en-1-yloxy, 4 -methylpent-1-en-1-yloxy, 1-methylpent-2-en-1-yloxy, 2 -methylpent-2-en-1-yloxy, 3-methylpent-2-en-1-yloxy, 4 -methylpent-2-en-1-yloxy, 1-methylpent-3-en-1-yloxy, 2 -methylpent-3-en-1-yloxy, 3-methylpent-3-en-1-yloxy, 4 -methylpent-3-en-1-yloxy, 1-methylpent-4-en-1-yloxy, 2 -methylpent-4-en-1-yloxy, 3-methylpent-4-en-1-yloxy, 4 -methylpent-4-en-1-yloxy, 1,1-dimethylbut-2-en-1-yloxy, 1,1-dimethylbut-3-en-1-yloxy, 1,2-dimethylbut-2-en-1-yloxy, 1,2-dimethylbut-3-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-2-en-1-yloxy, 2,3-dimethylbut-3-en-1-yloxy, 3,3-dimethylbut-2-en-1-yloxy, 1-ethylbut-2-en-1-yloxy, 1-ethylbut-3-en-1-yloxy, 2-ethylbut-2-en-1-yloxy, 2 -ethylbut-3-en-1-yloxy, 1,1,2-trimethylprop-2-en-1-yloxy, 1-ethyl-1-methylprop-2-en-1-yloxy, 1-ethyl-2 -methylprop-1-en-1-yloxy, 1-ethyl-2-methylprop-2-en-1-yloxy, preferably prop-2-en-1-yloxy;

—$C_3$–$C_6$-alkynyloxy: prop-2-yn-3-yloxy, n-but-1-yn-4-yloxy, n-but-2-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3 -methylbut-1-yn-3-yloxy, 3-methylbut-1-yn-4-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yloxy, n-hex-2-yn-6-yloxy, n-hex-3-yn-1-yloxy, n-hex-3-yn-2-yloxy, 3-methylpent-1-yn-3-yloxy, 3 -methylpent-1-yn-4-yloxy, 3-methylpent-1-yn-5-yloxy, 4 -methylpent-2-yn-4-yloxy, 4-methylpent-2-yn-5-yloxy, preferably prop-2-yn-1-yloxy;

—aryloxy-$C_1$–$C_6$-alkyl: aryloxymethyl, 1-(aryloxy)ethyl, 2-(aryloxy)ethyl, 1-(aryloxy)prop-1-yl, 2-(aryloxy)prop-1-yl, 3-(aryloxy)prop-1-yl, 1-(aryloxy)but-1-yl, 2 -(aryloxy)but-1-yl, 3-(aryloxy)but-1-yl, 4-(aryloxy)but-1-yl, 1-(aryloxy)but-2-yl, 2-(aryloxy)but-2-yl, 3 -(aryloxy)but-2-yl, 3-(aryloxy)but-2-yl, 4-(aryloxy)but-2-yl, 1-(aryloxymethyl)eth-1-yl, 1 -(aryloxymethyl)-1-(methyl)eth-1-yl, 1-(aryloxymethyl)prop-1-yl, preferably aryloxymethyl and 1-(aryloxy)ethyl;

—aryl-$C_3$–$C_6$-alkenyl: eg. 3-arylallyl, 4-arylbut-2-enyl, 4-arylbut-3-enyl, 5-arylpent-4-enyl, preferably 3-arylallyl or 4-arylbut-2-enyl;

—a saturated or unsaturated 4- to 6-membered heterocyclyic-$C_1$–$C_4$-alkyl group: (heterocyclyl)methyl, 1-(heterocyclyl)ethyl, 2-(heterocyclyl)ethyl, 1 -(heterocyclyl)prop-1-yl, 2-(heterocyclyl)prop-1-yl, 3 -(heterocyclyl)prop-1-yl, 1-(heterocyclyl)but-1-yl, 2 -(heterocyclyl)but-1-yl, 3-(heterocyclyl)but-1-yl, 4 -(heterocyclyl)but-1-yl, 1-(heterocyclyl)but-2-yl, 2 -(heterocyclyl)but-2-yl, 3-(heterocyclyl)but-2-yl, 3 -(heterocyclyl)but-2-yl, 4-(heterocyclyl)but-2-yl, 1-[(heterocyclyl)methyl]eth- 1-yl, 1-[(heterocyclyl)methyl] -1-(methyl)eth-1-yl, 1-[(heterocyclyl)methyl]prop-1-yl, preferably (heterocyclyl)methyl and 1-(heterocyclyl)ethyl.

Aryl is preferably phenyl or naphthyl, in particular phenyl;

aryloxy is preferably phenoxy, 1-naphthyloxy or 2-naphthyloxy, in particular phenoxy;

arylthio is preferably phenylthio, 1-naphthylthio or 2-naphthylthio, in particular phenylthio;

heteroaryl is preferably a 5- or 6-membered aromatic heterocycle containing an oxygen atom and a sulfur atom or a 5- or 6-membered aromatic heterocycle containing 1 or 2 heteroatoms selected from a group consisting of 2 nitrogen atoms and one oxygen or sulfur atom: such as: 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl, in particular pyridyl, pyrimidyl, furanyl and thienyl.

Among the saturated or unsaturated 4- to 6-membered heterocycles which, in addition to C atoms, in each case carry one or two ring members selected from the group consisting of one oxygen or sulfur atom and one or two nitrogen atoms and one or two groups —$N(CH_3)$—, the following rings are particularly preferred: oxetanyl, tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, 1,2,4-oxadiazolidinyl, 1,3,4-oxadiazolidinyl, 1,2,4-thiadiazolidinyl, 1,3,4-thiadiazolidinyl, 1,2,4-triazolidinyl, 1,3,4-triazolidinyl, 2,3-dihydrofuryl, 2,4-dihydrofuryl, 2,3-dihydrothienyl, 2,4-dihydrothienyl, 2,3-pyrrolinyl, 2,4-pyrrolinyl, 2,3-isoxazolinyl, 3,4-isoxazolinyl, 4,5-isoxazolinyl, 2,3-isothiazolinyl, 3,4-isothiazolinyl, 4,5-isothiazolinyl, 2,3-dihydropyrazolyl, 3,4-dihydropyrazolyl, 4,5-dihydropyrazolyl, 2,3-dihydrooxazolyl, 3,4-dihydrooxazolyl, thiazolyl, imidazolyl, 1,2,4-oxadiazolyl, 1,3,4-oxadiazolyl, 1,2,4-thiadiazolyl, 1,3,4-thiadiazolyl, 1,2,4-triazolyl and 1,3,4-triazolyl, 1,3-dioxolanyl, piperidinyl, tetrahydropyridazinyl, tetrahydropyrimidinyl, tetrahydropyrazinyl, 1,3,5-tetrahydrotriazinyl and 1,2,4-tetrahydrotriazinyl.

If desired, the aryl ring and all saturated, unsaturated or aromatic heterocycles can carry one of the following radicals on each substitutable C atom:

—halogen, preferably fluorine or chlorine;

—$C_1$–$C_4$-alkyl, preferably methyl;

—$C_1$— or $C_2$-haloalkyl, preferably trifluoromethyl;

—$C_3$–$C_6$-cycloalkyl, preferably cyclopropyl;

—$C_1$–$C_4$-alkoxy, preferably methoxy;

—$C_1$— or $C_2$-haloalkoxy, preferably difluoromethoxy.

The aryl rings and the heterocycles are preferably unsubstituted or carry 1 to 3 of the abovementioned radicals.

In the case where n is 2, 3 or 4, two adjacent radicals $R^5$ can also together form a fused 1,3-butadiene-1,4-diyl bridge or a mono- or dihalogenated 1,3-butadiene-1,4-diyl bridge, among the halogen atoms fluorine, chlorine and bromine being particularly preferred.

The radical —C(R⁴)=N—O—R¹ can be on the phenyl radical in the 2-position, or preferably in the 3- or 4-position, relative to the bridge —O—CH₂— in the 1-position.

Among the compounds I in which X is =CH—OCH₃, those are particularly preferred in which Y is oxygen, R¹ is C₁-C₆-alkyl, C₂-C₆-alkenyl, C₃-C₆-alkynyl, C₁-C₆-haloalkyl or C₃-C₆-haloalkenyl;

R² is cyano, chlorine, fluorine, methyl, trifluoromethyl or methoxy;

R³ is hydrogen, cyano, chlorine, fluorine, methyl or methoxy;

R⁴ is cyano, chlorine, bromine, C₁-C₆-alkoxy, C₁-C₆-alkylthio, C₃-C₆-alkenyloxy, phenyloxy or phenylthio and R⁵ is cyano, halogen, C₁-C₆-alkyl, C₁-C₆-haloalkyl, C₁-C₆-alkoxy or phenyl.

Among the compounds I in which X is =CH—CH₃, those are particularly preferred in which Y is oxygen, R¹ is C₁-C₆-alkyl, C₂-C₆-alkenyl, C₃-C₆-alkynyl, C₁-C₆-haloalkyl or C₃-C₆-haloalkenyl;

R² is cyano, chlorine, fluorine, methyl, trifluoromethyl or methoxy;

R³ is hydrogen, cyano, chlorine, fluorine, methyl or methoxy;

R⁴ is cyano, chlorine, bromine, C₁-C₆-alkoxy, C₁-C₆-alkylthio, C₃-C₆-alkenyloxy, phenyloxy or phenylthio and R⁵ is cyano, halogen, C₁-C₆-alkyl, C₁-C₆-haloalkyl, C₁-C₆-alkoxy or phenyl.

Among the compounds I in which X is =N—OCH₃, those are particularly preferred in which Y is oxygen or —NH— and R¹ is C₁-C₆-alkyl, C₂-C₆-alkenyl, C₃-C₆-alkynyl, C₁-C₆-haloalkyl or C₃-C₆-haloalkenyl;

R² is cyano, chlorine, fluorine, methyl, trifluormethyl or methoxy;

R³ is hydrogen, cyano, chlorine, fluorine, methyl or methoxy;

R⁴ is cyano, chlorine, bromine, C₁-C₆-alkoxy, C₁-C₆-alkylthio, C₃-C₆-alkenyloxy, phenyloxy or phenylthio and R⁵ is cyano, halogen, C₁-C₆-alkyl, C₁-C₆-haloalkyl, C₁-C₆-alkoxy or phenyl.

In the case of the intermediates IVb' and XI', those meanings of the variables are preferred which have already been specified as preferred in the case of the compounds I.

The novel compounds of the formula I, IVb' and XI' can be obtained during preparation as E/Z isomer mixtures with respect to the C=X bond and the compounds I also with respect to the (R¹O)N=C(R⁴) bond. If desired, the isomer mixtures can be separated into the largely pure isomers in a customary manner, eg. by crystallization or chromatography.

Both the pure isomers and all mixtures of the various isomers are covered by the invention and are utilizable as fungicides or as pesticides.

Particularly preferred compounds I are those in which

—the C=X group has the E configuration, ie. —CO—Y—R⁶ and the radical —OCH₃ or —CH₃ are in the trans-position.

With respect to their biological activity against harmful fungi and/or pests, the following substituted benzoxyphenyl derivatives I are very particularly preferred:

—Compounds of the formula I-1:

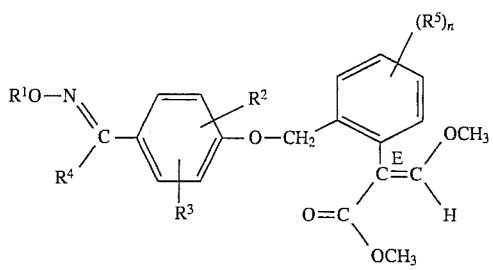

Representatives of this structure type are the compounds No. A.0001 to No. A.1958 listed in Table A.

—Compounds of the formula I-2:

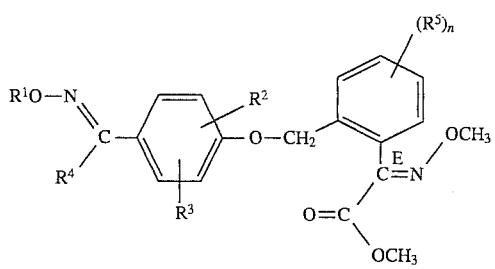

Representatives of this structure type are the compounds No. C.0001 to No. C.1958, which are substituted as the corresponding compounds No. A.0001 to No. A.1958 of Table A.

—Compounds of the formula I-3:

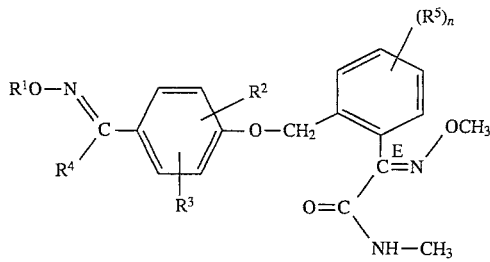

Representatives of this structure type are the compounds No. D.0001 to No. D.1958, which are substituted as the corresponding compounds No. A.0001 to No. A.1958 of Table A.

—Compounds of the formula I-4:

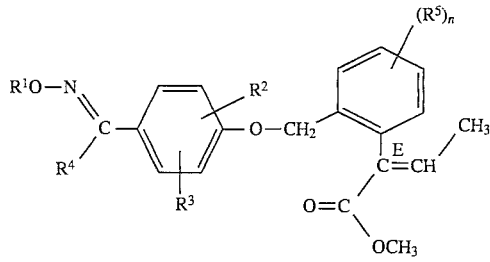

Representatives of this structure type are the compounds No. E.0001 to No. E.1958, which are substituted as the corresponding compounds No. A.0001 to No. A.1958 of Table A.

—Compounds of the formula I-5:

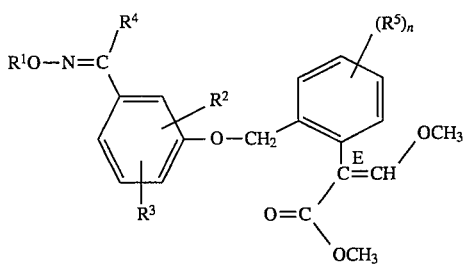

Representatives of this structure type are the compounds No. B.001 to B.544 listed in Table B.

—Compounds of the formula I-6:

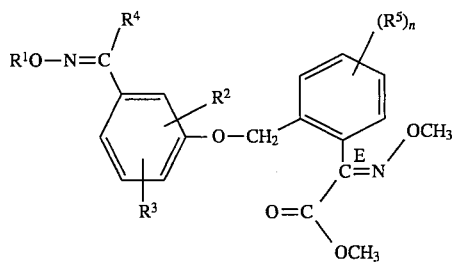

Representatives of this structure type are the compounds No. F.001 to No. F.544, which are substituted as the corresponding compounds No. B.001 to No. B.544 of Table B.

—Compounds of the formula I-7:

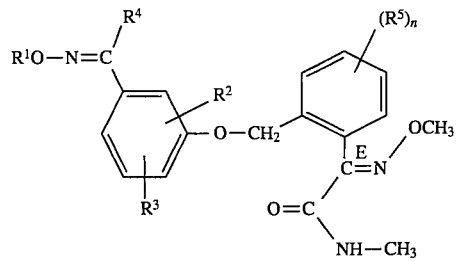

Representatives of this structure type are the compounds No. G.001 to No. G.544, which are substituted as the corresponding compounds No. B.001 to No. B.544 of Table B.

—Compounds of the formula I-8:

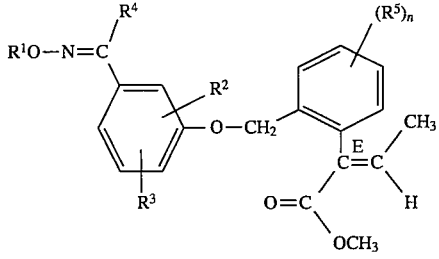

Representatives of this structure type are the compounds No. H.001 to No. H.544, which are substituted as the corresponding compounds No. B.001 to No. B.544 of Table B.

TABLE A

| No. | $R^1$ | $R^2$ | $R^3$ | $R^4$ | $R^5n$ |
|---|---|---|---|---|---|
| A.0001 | Methyl | 2-$CH_3$ | H | $OCH_3$ | H |

TABLE A-continued

| No. | $R^1$ | $R^2$ | $R^3$ | $R^4$ | $R^5n$ |
|---|---|---|---|---|---|
| A.0002 | Methyl | 2-$CH_3$ | H | $OCH_3$ | 3-Cl |
| A.0003 | Methyl | 2-$CH_3$ | H | $OCH_3$ | 4-Cl |
| A.0004 | Methyl | 2-$CH_3$ | H | $OCH_3$ | 6-Cl |
| A.0005 | Methyl | 2-$CH_3$ | H | $OCH_3$ | 3-$CH_3$ |
| A.0006 | Methyl | 2-$CH_3$ | H | $OCH_3$ | 4-$CH_3$ |
| A.0007 | Methyl | 2-$CH_3$ | H | $OCH_3$ | 3-$CF_3$ |
| A.0008 | Methyl | 2-$CH_3$ | H | $OCH_3$ | 6-$CH_3$ |
| A.0009 | Methyl | 2-$CH_3$ | H | $OCH_3$ | 6-$C_6H_5$ |
| A.0010 | Ethyl | 2-$CH_3$ | H | $OCH_3$ | H |
| A.0011 | n-Propyl | 2-$CH_3$ | H | $OCH_3$ | H |
| A.0012 | i-Propyl | 2-$CH_3$ | H | $OCH_3$ | H |
| A.0013 | n-Butyl | 2-$CH_3$ | H | $OCH_3$ | H |
| A.0014 | i-Butyl | 2-$CH_3$ | H | $OCH_3$ | H |
| A.0015 | sec-Butyl | 2-$CH_3$ | H | $OCH_3$ | H |
| A.0016 | tert-Butyl | 2-$CH_3$ | H | $OCH_3$ | H |
| A.0017 | n-Pentyl | 2-$CH_3$ | H | $OCH_3$ | H |
| A.0018 | n-Hexyl | 2-$CH_3$ | H | $OCH_3$ | H |
| A.0019 | 2-Propenyl | 2-$CH_3$ | H | $OCH_3$ | H |
| A.0020 | 2-Propenyl | 2-$CH_3$ | H | $OCH_3$ | 3-Cl |
| A.0021 | 2-Propenyl | 2-$CH_3$ | H | $OCH_3$ | 4-Cl |
| A.0022 | 2-Propenyl | 2-$CH_3$ | H | $OCH_3$ | 6-Cl |
| A.0023 | 2-Propenyl | 2-$CH_3$ | H | $OCH_3$ | 3-$OCH_3$ |
| A.0024 | 2-Propenyl | 2-$CH_3$ | H | $OCH_3$ | 4-$OCH_3$ |
| A.0025 | 2-Propenyl | 2-$CH_3$ | H | $OCH_3$ | 3-$CF_3$ |
| A.0026 | 2-Propenyl | 2-$CH_3$ | H | $OCH_3$ | 6-$CH_3$ |
| A.0027 | 2-Propenyl | 2-$CH_3$ | H | $OCH_3$ | 6-$C_6H_5$ |
| A.0028 | (E)-3-Chloro-2-propenyl | 2-$CH_3$ | H | $OCH_3$ | H |
| A.0029 | 2-Chloro-2-propenyl | 2-$CH_3$ | H | $OCH_3$ | H |
| A.0030 | (E)-2-Butenyl | 2-$CH_3$ | H | $OCH_3$ | H |
| A.0031 | 2-Methyl-2-propenyl | 2-$CH_3$ | H | $OCH_3$ | H |
| A.0032 | (Z)-3-Chloro-2-butenyl | 2-$CH_3$ | H | $OCH_3$ | H |
| A.0033 | 3-Methyl-2-butenyl | 2-$CH_3$ | H | $OCH_3$ | H |
| A.0034 | 2-Propynyl | 2-$CH_3$ | H | $OCH_3$ | H |
| A.0035 | 2-Propynyl | 2-$CH_3$ | H | $OCH_3$ | 3-Cl |
| A.0036 | 2-Propynyl | 2-$CH_3$ | H | $OCH_3$ | 4-Cl |
| A.0037 | 2-Propynyl | 2-$CH_3$ | H | $OCH_3$ | 6-Cl |
| A.0038 | 2-Propynyl | 2-$CH_3$ | H | $OCH_3$ | 3-$CH_3$ |
| A.0039 | 2-Propynyl | 2-$CH_3$ | H | $OCH_3$ | 4-$CH_3$ |
| A.0040 | 2-Propynyl | 2-$CH_3$ | H | $OCH_3$ | 3-$CF_3$ |
| A.0041 | 2-Propynyl | 2-$CH_3$ | H | $OCH_3$ | 6-$CH_3$ |
| A.0042 | 2-Propynyl | 2-$CH_3$ | H | $OCH_3$ | 6-$C_6H_5$ |
| A.0043 | 2-Butynyl | 2-$CH_3$ | H | $OCH_3$ | H |
| A.0044 | 3-Butyn-2-yl | 2-$CH_3$ | H | $OCH_3$ | H |
| A.0045 | Cyanomethyl | 2-$CH_3$ | H | $OCH_3$ | H |
| A.0046 | Methoxycarbonylmethyl | 2-$CH_3$ | H | $OCH_3$ | H |
| A.0047 | tert-Butoxycarbonylmethyl | 2-$CH_3$ | H | $OCH_3$ | H |
| A.0048 | 1-(tert-Butoxycarbonyl)ethyl | 2-$CH_3$ | H | $OCH_3$ | H |
| A.0049 | Cyclopropylmethyl | 2-$CH_3$ | H | $OCH_3$ | H |
| A.0050 | 1-Methylcyclopentyl | 2-$CH_3$ | H | $OCH_3$ | H |
| A.0051 | Cyclohexyl | 2-$CH_3$ | H | $OCH_3$ | H |
| A.0052 | 1-Methoxypropan-2-yl | 2-$CH_3$ | H | $OCH_3$ | H |
| A.0053 | Benzyl | 2-$CH_3$ | H | $OCH_3$ | H |
| A.0054 | Benzyl | 2-$CH_3$ | H | $OCH_3$ | 3-Cl |
| A.0055 | Benzyl | 2-$CH_3$ | H | $OCH_3$ | 4-Cl |
| A.0056 | Benzyl | 2-$CH_3$ | H | $OCH_3$ | 6-Cl |
| A.0057 | Benzyl | 2-$CH_3$ | H | $OCH_3$ | 3-$OCH_3$ |

TABLE A-continued

| No. | R¹ | R² | R³ | R⁴ | R⁵n |
|---|---|---|---|---|---|
| A.0058 | Benzyl | 2-CH₃ | H | OCH₃ | 4-OCH₃ |
| A.0059 | Benzyl | 2-CH₃ | H | OCH₃ | 3-CF₃ |
| A.0060 | Benzyl | 2-CH₃ | H | OCH₃ | 6-CH₃ |
| A.0061 | Benzyl | 2-CH₃ | H | OCH₃ | 6-C₆H₅ |
| A.0062 | 3-Methyl-benzyl | 2-CH₃ | H | OCH₃ | H |
| A.0063 | 2-Fluoro-benzyl | 2-CH₃ | H | OCH₃ | H |
| A.0064 | 3-Fluoro-benzyl | 2-CH₃ | H | OCH₃ | H |
| A.0065 | 4-Chloro-benzyl | 2-CH₃ | H | OCH₃ | H |
| A.0066 | 3,4-Dichloro-benzyl | 2-CH₃ | H | OCH₃ | H |
| A.0067 | 2,6-Difluoro-benzyl | 2-CH₃ | H | OCH₃ | H |
| A.0068 | 3-Trifluoromethyl-benzyl | 2-CH₃ | H | OCH₃ | H |
| A.0069 | 3-Cyano-benzyl | 2-CH₃ | H | OCH₃ | H |
| A.0070 | 4-Methoxy-benzyl | 2-CH₃ | H | OCH₃ | H |
| A.0071 | 4-Methoxycarbonyl-benzyl | 2-CH₃ | H | OCH₃ | H |
| A.0072 | 3-Phenyl-benzyl | 2-CH₃ | H | OCH₃ | H |
| A.0073 | (5-Chloro-3-thienyl)-methyl | 2-CH₃ | H | OCH₃ | H |
| A.0074 | (2,5-Dichloro-3-thienyl)-methyl | 2-CH₃ | H | OCH₃ | H |
| A.0075 | (1,3-Dioxolan-2-yl)methyl | 2-CH₃ | H | OCH₃ | H |
| A.0076 | 1-Phenyl-ethyl | 2-CH₃ | H | OCH₃ | H |
| A.0077 | 1-(4-Methyl-phenyl)-ethyl | 2-CH₃ | H | OCH₃ | H |
| A.0078 | 1-(4-Chloro-phenyl)-ethyl | 2-CH₃ | H | OCH₃ | H |
| A.0079 | 1-(3-Trifluoromethyl-phenyl)-ethyl | 2-CH₃ | H | OCH₃ | H |
| A.0080 | 2-Phenyl-ethyl | 2-CH₃ | H | OCH₃ | H |
| A.0081 | 3-Phenyl-propan-1-yl | 2-CH₃ | H | OCH₃ | H |
| A.0082 | 4-(4-Chloro-phenyl)-2-butenyl | 2-CH₃ | H | OCH₃ | H |
| A.0083 | Methyl | 2-CH₃ | H | OC₂H₅ | H |
| A.0084 | Methyl | 2-CH₃ | H | OC₂H₅ | 3-Cl |
| A.0085 | Methyl | 2-CH₃ | H | OC₂H₅ | 4-Cl |
| A.0086 | Methyl | 2-CH₃ | H | OC₂H₅ | 3-OCH₃ |
| A.0087 | Methyl | 2-CH₃ | H | OC₂H₅ | 4-OCH₃ |
| A.0088 | Methyl | 2-CH₃ | H | OC₂H₅ | 3-CF₃ |
| A.0089 | Methyl | 2-CH₃ | H | OC₂H₅ | 6-CH₃ |
| A.0090 | Methyl | 2-CH₃ | H | OC₂H₅ | 6-C₆H₅ |
| A.0091 | Ethyl | 2-CH₃ | H | OC₂H₅ | H |
| A.0092 | n-Propyl | 2-CH₃ | H | OC₂H₅ | H |
| A.0093 | i-Propyl | 2-CH₃ | H | OC₂H₅ | H |
| A.0094 | n-Butyl | 2-CH₃ | H | OC₂H₅ | H |
| A.0095 | i-Butyl | 2-CH₃ | H | OC₂H₅ | H |
| A.0096 | s-Butyl | 2-CH₃ | H | OC₂H₅ | H |
| A.0097 | t-Butyl | 2-CH₃ | H | OC₂H₅ | H |
| A.0098 | n-Pentyl | 2-CH₃ | H | OC₂H₅ | H |
| A.0099 | n-Hexyl | 2-CH₃ | H | OC₂H₅ | H |
| A.0100 | 2-Propenyl | 2-CH₃ | H | OC₂H₅ | H |
| A.0101 | 2-Propenyl | 2-CH₃ | H | OC₂H₅ | 3-Cl |
| A.0102 | 2-Propenyl | 2-CH₃ | H | OC₂H₅ | 6-Cl |
| A.0103 | 2-Propenyl | 2-CH₃ | H | OC₂H₅ | 6-Cl |
| A.0104 | 2-Propenyl | 2-CH₃ | H | OC₂H₅ | 3-CH₃ |
| A.0105 | 2-Propenyl | 2-CH₃ | H | OC₂H₅ | 4-CH₃ |
| A.0106 | 2-Propenyl | 2-CH₃ | H | OC₂H₅ | 3-CF₃ |
| A.0107 | 2-Propenyl | 2-CH₃ | H | OC₂H₅ | 6-CH₃ |
| A.0108 | 2-Propenyl | 2-CH₃ | H | OC₂H₅ | 6-C₆H₅ |
| A.0109 | (E)-3-Chloro-2-propenyl | 2-CH₃ | H | OC₂H₅ | H |
| A.0110 | 2-Chloro-2-propenyl | 2-CH₃ | H | OC₂H₅ | H |
| A.0111 | (E)-2-Butenyl | 2-CH₃ | H | OC₂H₅ | H |
| A.0112 | 2-Methyl-2-propenyl | 2-CH₃ | H | OC₂H₅ | H |
| A.0113 | (Z)-3-Chloro-2-butenyl | 2-CH₃ | H | OC₂H₅ | H |
| A.0114 | 3-Methyl-2-butenyl | 2-CH₃ | H | OC₂H₅ | H |
| A.0115 | 2-Propynyl | 2-CH₃ | H | OC₂H₅ | H |
| A.0116 | 2-Propynyl | 2-CH₃ | H | OC₂H₅ | 3-Cl |
| A.0117 | 2-Propynyl | 2-CH₃ | H | OC₂H₅ | 4-Cl |
| A.0118 | 2-Propynyl | 2-CH₃ | H | OC₂H₅ | 6-Cl |
| A.0119 | 2-Propynyl | 2-CH₃ | H | OC₂H₅ | 3-CH₃ |
| A.0120 | 2-Propynyl | 2-CH₃ | H | OC₂H₅ | 4-CH₃ |
| A.0121 | 2-Propynyl | 2-CH₃ | H | OC₂H₅ | 3-CF₃ |
| A.0122 | 2-Propynyl | 2-CH₃ | H | OC₂H₅ | 6-CH₃ |
| A.0123 | 2-Propynyl | 2-CH₃ | H | OC₂H₅ | 6-C₆H₅ |
| A.0124 | 2-Butynyl | 2-CH₃ | H | OC₂H₅ | H |
| A.0125 | 3-Butyn-2-yl | 2-CH₃ | H | OC₂H₅ | H |
| A.0126 | Cyano-methyl | 2-CH₃ | H | OC₂H₅ | H |
| A.0127 | Methoxycarbonyl-methyl | 2-CH₃ | H | OC₂H₅ | H |
| A.0128 | tert-Butoxycarbonyl-methyl | 2-CH₃ | H | OC₂H₅ | H |
| A.0129 | 1-(tert-Butoxycarbonyl)-ethyl | 2-CH₃ | H | OC₂H₅ | H |
| A.0130 | Cyclopropyl-methyl | 2-CH₃ | H | OC₂H₅ | H |
| A.0131 | 1-Methyl-cyclopentyl | 2-CH₃ | H | OC₂H₅ | H |
| A.0132 | Cyclohexyl | 2-CH₃ | H | OC₂H₅ | H |
| A.0133 | 1-Methoxy-propan-2-yl | 2-CH₃ | H | OC₂H₅ | H |
| A.0134 | Benzyl | 2-CH₃ | H | OC₂H₅ | H |
| A.0135 | Benzyl | 2-CH₃ | H | OC₂H₅ | 3-Cl |
| A.0136 | Benzyl | 2-CH₃ | H | OC₂H₅ | 4-Cl |
| A.0137 | Benzyl | 2-CH₃ | H | OC₂H₅ | 6-Cl |
| A.0138 | Benzyl | 2-CH₃ | H | OC₂H₅ | 3-CH₃ |
| A.0139 | Benzyl | 2-CH₃ | H | OC₂H₅ | 4-CH₃ |
| A.0140 | Benzyl | 2-CH₃ | H | OC₂H₅ | 3-CF₃ |
| A.0141 | Benzyl | 2-CH₃ | H | OC₂H₅ | 6-CH₃ |
| A.0142 | Benzyl | 2-CH₃ | H | OC₂H₅ | 6-C₆H₅ |
| A.0143 | 3-Methyl-benzyl | 2-CH₃ | H | OC₂H₅ | H |
| A.0144 | 2-Fluoro-benzyl | 2-CH₃ | H | OC₂H₅ | H |
| A.0145 | 3-Fluoro-benzyl | 2-CH₃ | H | OC₂H₅ | H |
| A.0146 | 4-Chloro-benzyl | 2-CH₃ | H | OC₂H₅ | H |

TABLE A-continued

| No. | R¹ | R² | R³ | R⁴ | R⁵n |
|---|---|---|---|---|---|
| A.0148 | 3,4-Dichlorobenzyl | 2-CH₃ | H | OC₂H₅ | H |
| A.0149 | 2,6-Difluorobenzyl | 2-CH₃ | H | OC₂H₅ | H |
| A.0150 | 3-Trifluoromethylbenzyl | 2-CH₃ | H | OC₂H₅ | H |
| A.0151 | 3-Cyanobenzyl | 2-CH₃ | H | OC₂H₅ | H |
| A.0152 | 4-Methoxybenzyl | 2-CH₃ | H | OC₂H₅ | H |
| A.0153 | 4-Methoxycarbonylbenzyl | 2-CH₃ | H | OC₂H₅ | H |
| A.0154 | 3-Phenylbenzyl | 2-CH₃ | H | OC₂H₅ | H |
| A.0155 | (5-Chloro-3-thienyl)methyl | 2-CH₃ | H | OC₂H₅ | H |
| A.0156 | (2,5-Dichloro-3-thienyl)methyl | 2-CH₃ | H | OC₂H₅ | H |
| A.0157 | (1,3-Dioxolan-2-yl)methyl | 2-CH₃ | H | OC₂H₅ | H |
| A.0158 | 1-Phenylethyl | 2-CH₃ | H | OC₂H₅ | H |
| A.0159 | 1-(4-Methylphenyl)ethyl | 2-CH₃ | H | OC₂H₅ | H |
| A.0160 | 1-(4-Chlorophenyl)ethyl | 2-CH₃ | H | OC₂H₅ | H |
| A.0161 | 1-(3-Trifluoromethylphenyl)ethyl | 2-CH₃ | H | OC₂H₅ | H |
| A.0162 | 2-Phenylethyl | 2-CH₃ | H | OC₂H₅ | H |
| A.0163 | 3-Phenylpropan-1-yl | 2-CH₃ | H | OC₂H₅ | H |
| A.0164 | 4-(4-Chlorophenyl)-2-butenyl | 2-CH₃ | H | OC₂H₅ | H |
| A.0165 | Methyl | 2-CH₃ | H | OCH₂CH=CH₂ | H |
| A.0166 | Methyl | 2-CH₃ | H | OCH₂CH=CH₂ | 3-Cl |
| A.0167 | Methyl | 2-CH₃ | H | OCH₂CH=CH₂ | 4-Cl |
| A.0168 | Methyl | 2-CH₃ | H | OCH₂CH=CH₂ | 6-Cl |
| A.0169 | Methyl | 2-CH₃ | H | OCH₂CH=CH₂ | 3-CH₃ |
| A.0170 | Methyl | 2-CH₃ | H | OCH₂CH=CH₂ | 4-CH₃ |
| A.0171 | Methyl | 2-CH₃ | H | OCH₂CH=CH₂ | 3-CF₃ |
| A.0172 | Methyl | 2-CH₃ | H | OCH₂CH=CH₂ | 6-CH₃ |
| A.0173 | Methyl | 2-CH₃ | H | OCH₂CH=CH₂ | 6-C₆H₅ |
| A.0174 | Ethyl | 2-CH₃ | H | OCH₂CH=CH₂ | H |
| A.0175 | n-Propyl | 2-CH₃ | H | OCH₂CH=CH₂ | H |
| A.0176 | Isopropyl | 2-CH₃ | H | OCH₂CH=CH₂ | H |
| A.0177 | n-Butyl | 2-CH₃ | H | OCH₂CH=CH₂ | H |
| A.0178 | i-Butyl | 2-CH₃ | H | OCH₂CH=CH₂ | H |
| A.0179 | sec-Butyl | 2-CH₃ | H | OCH₂CH=CH₂ | H |
| A.0180 | tert-Butyl | 2-CH₃ | H | OCH₂CH=CH₂ | H |
| A.0181 | n-Pentyl | 2-CH₃ | H | OCH₂CH=CH₂ | H |
| A.0182 | n-Hexyl | 2-CH₃ | H | OCH₂CH=CH₂ | H |
| A.0183 | 2-Propenyl | 2-CH₃ | H | OCH₂CH=CH₂ | H |
| A.0184 | 2-Propenyl | 2-CH₃ | H | OCH₂CH=CH₂ | 3-Cl |
| A.0185 | 2-Propenyl | 2-CH₃ | H | OCH₂CH=CH₂ | 4-Cl |
| A.0186 | 2-Propenyl | 2-CH₃ | H | OCH₂CH=CH₂ | 6-Cl |
| A.0187 | 2-Propenyl | 2-CH₃ | H | OCH₂CH=CH₂ | 3-CH₃ |
| A.0188 | 2-Propenyl | 2-CH₃ | H | OCH₂CH=CH₂ | 4-CH₃ |
| A.0189 | 2-Propenyl | 2-CH₃ | H | OCH₂CH=CH₂ | 3-CF₃ |
| A.0190 | 2-Propenyl | 2-CH₃ | H | OCH₂CH=CH₂ | 6-CH₃ |
| A.0191 | 2-Propenyl | 2-CH₃ | H | OCH₂CH=CH₂ | 6-C₆H₅ |
| A.0192 | (E)-3-Chloro-2-propenyl | 2-CH₃ | H | OCH₂CH=CH₂ | H |
| A.0193 | 2-Chloro-2-propenyl | 2-CH₃ | H | OCH₂CH=CH₂ | H |
| A.0194 | (E)-2-Butenyl | 2-CH₃ | H | OCH₂CH=CH₂ | H |
| A.0195 | 2-Methyl-2-propenyl | 2-CH₃ | H | OCH₂CH=CH₂ | H |
| A.0196 | (Z)-3-Chloro-2-butenyl | 2-CH₃ | H | OCH₂CH=CH₂ | H |
| A.0197 | 3-Methyl-2-butenyl | 2-CH₃ | H | OCH₂CH=CH₂ | H |
| A.0198 | 2-Propynyl | 2-CH₃ | H | OCH₂CH=CH₂ | H |
| A.0199 | 2-Propynyl | 2-CH₃ | H | OCH₂CH=CH₂ | 3-Cl |
| A.0200 | 2-Propynyl | 2-CH₃ | H | OCH₂CH=CH₂ | 4-Cl |
| A.0201 | 2-Propynyl | 2-CH₃ | H | OCH₂CH=CH₂ | 6-Cl |
| A.0202 | 2-Propynyl | 2-CH₃ | H | OCH₂CH=CH₂ | 3-CH₃ |
| A.0203 | 2-Propynyl | 2-CH₃ | H | OCH₂CH=CH₂ | 4-CH₃ |
| A.0204 | 2-Propynyl | 2-CH₃ | H | OCH₂CH=CH₂ | 3-CF₃ |
| A.0205 | 2-Propynyl | 2-CH₃ | H | OCH₂CH=CH₂ | 6-CH₃ |
| A.0206 | 2-Propynyl | 2-CH₃ | H | OCH₂CH=CH₂ | 6-C₆H₅ |
| A.0207 | 2-Butynyl | 2-CH₃ | H | OCH₂CH=CH₂ | H |
| A.0208 | 3-Butyn-2-yl | 2-CH₃ | H | OCH₂CH=CH₂ | H |
| A.0209 | cyanomethyl | 2-CH₃ | H | OCH₂CH=CH₂ | H |
| A.0210 | Methoxycarbonylmethyl | 2-CH₃ | H | OCH₂CH=CH₂ | H |
| A.0211 | tert-Butoxycarbonylmethyl | 2-CH₃ | H | OCH₂CH=CH₂ | H |
| A.0212 | 1-(tert-Butoxycarbonyl)ethyl | 2-CH₃ | H | OCH₂CH=CH₂ | H |
| A.0213 | Cyclopropylmethyl | 2-CH₃ | H | OCH₂CH=CH₂ | H |
| A.0214 | 1-Methylcyclopentyl | 2-CH₃ | H | OCH₂CH=CH₂ | H |
| A.0215 | cyclohexyl | 2-CH₃ | H | OCH₂CH=CH₂ | H |
| A.0216 | 1-Methoxypropan-2-yl | 2-CH₃ | H | OCH₂CH=CH₂ | H |
| A.0217 | Benzyl | 2-CH₃ | H | OCH₂CH=CH₂ | H |
| A.0218 | Benzyl | 2-CH₃ | H | OCH₂CH=CH₂ | 3-Cl |
| A.0219 | Benzyl | 2-CH₃ | H | OCH₂CH=CH₂ | 4-Cl |
| A.0220 | Benzyl | 2-CH₃ | H | OCH₂CH=CH₂ | 6-Cl |
| A.0221 | Benzyl | 2-CH₃ | H | OCH₂CH=CH₂ | 3-OCH₃ |
| A.0222 | Benzyl | 2-CH₃ | H | OCH₂CH=CH₂ | 4-CH₃ |
| A.0223 | Benzyl | 2-CH₃ | H | OCH₂CH=CH₂ | 3-CF₃ |
| A.0224 | Benzyl | 2-CH₃ | H | OCH₂CH=CH₂ | 6-CH₃ |
| A.0225 | Benzyl | 2-CH₃ | H | OCH₂CH=CH₂ | 6-C₆H₅ |
| A.0226 | 3-Methylbenzyl | 2-CH₃ | H | OCH₂CH=CH₂ | H |
| A.0227 | 2-Fluorobenzyl | 2-CH₃ | H | OCH₂CH=CH₂ | H |
| A.0228 | 3-Fluorobenzyl | 2-CH₃ | H | OCH₂CH=CH₂ | H |
| A.0229 | 4-Chlorobenzyl | 2-CH₃ | H | OCH₂CH=CH₂ | H |
| A.0230 | 3,4-Dichlorobenzyl | 2-CH₃ | H | OCH₂CH=CH₂ | H |
| A.0231 | 2,6-Difluorobenzyl | 2-CH₃ | H | OCH₂CH=CH₂ | H |
| A.0232 | 3-Trifluoromethylbenzyl | 2-CH₃ | H | OCH₂CH=CH₂ | H |
| A.0233 | 3-Cyanobenzyl | 2-CH₃ | H | OCH₂CH=CH₂ | H |

TABLE A-continued

| No. | R¹ | R² | R³ | R⁴ | R⁵n |
|---|---|---|---|---|---|
| A.0234 | 4-Methoxy-benzyl | 2-CH₃ | H | OCH₂CH=CH₂ | H |
| A.0235 | 4-Methoxy-carbonyl-benzyl | 2-CH₃ | H | OCH₂CH=CH₂ | H |
| A.0236 | 3-Phenyl-benzyl | 2-CH₃ | H | OCH₂CH=CH₂ | H |
| A.0237 | (5-Chloro-3-thienyl)-methyl | 2-CH₃ | H | OCH₂CH=CH₂ | H |
| A.0238 | (2,5-Dichloro-3-thienyl)-methyl | 2-CH₃ | H | OCH₂CH=CH₂ | H |
| A.0239 | (1,3-Dioxolan-2-yl)methyl | 2-CH₃ | H | OCH₂CH=CH₂ | H |
| A.0240 | 1-Phenyl-ethyl | 2-CH₃ | H | OCH₂CH=CH₂ | H |
| A.0241 | 1-(4-Methyl-phenyl)-ethyl | 2-CH₃ | H | OCH₂CH=CH₂ | H |
| A.0242 | 1-(4-Chloro-phenyl)-ethyl | 2-CH₃ | H | OCH₂CH=CH₂ | H |
| A.0243 | 1-(3-Trifluoro-methyl-phenyl)-ethyl | 2-CH₃ | H | OCH₂CH=CH₂ | H |
| A.0244 | 2-Phenyl-ethyl | 2-CH₃ | H | OCH₂CH=CH₂ | H |
| A.0245 | 3-Phenyl-propan-1-yl | 2-CH₃ | H | OCH₂CH=CH₂ | H |
| A.0246 | 4-(4-Chloro-phenyl)-2-butenyl | 2-CH₃ | H | OCH₂CH=CH₂ | H |
| A.0247 | Methyl | 2-CH₃ | H | SCH₃ | H |
| A.0248 | Methyl | 2-CH₃ | H | SCH₃ | 3-Cl |
| A.0249 | Methyl | 2-CH₃ | H | SCH₃ | 4-Cl |
| A.0250 | Methyl | 2-CH₃ | H | SCH₃ | 6-Cl |
| A.0251 | Methyl | 2-CH₃ | H | SCH₃ | 3-CH₃ |
| A.0252 | Methyl | 2-CH₃ | H | SCH₃ | 4-CH₃ |
| A.0253 | Methyl | 2-CH₃ | H | SCH₃ | 3-CF₃ |
| A.0254 | Methyl | 2-CH₃ | H | SCH₃ | 6-CH₃ |
| A.0255 | Methyl | 2-CH₃ | H | SCH₃ | 6-C₆H₅ |
| A.0256 | Ethyl | 2-CH₃ | H | SCH₃ | H |
| A.0257 | n-Propyl | 2-CH₃ | H | SCH₃ | H |
| A.0258 | i-Propyl | 2-CH₃ | H | SCH₃ | H |
| A.0259 | n-Butyl | 2-CH₃ | H | SCH₃ | H |
| A.0260 | i-Butyl | 2-CH₃ | H | SCH₃ | H |
| A.0261 | sec-Butyl | 2-CH₃ | H | SCH₃ | H |
| A.0262 | tert-Butyl | 2-CH₃ | H | SCH₃ | H |
| A.0263 | n-Pentyl | 2-CH₃ | H | SCH₃ | H |
| A.0264 | n-Hexyl | 2-CH₃ | H | SCH₃ | H |
| A.0265 | 2-Propenyl | 2-CH₃ | H | SCH₃ | H |
| A.0266 | 2-Propenyl | 2-CH₃ | H | SCH₃ | 3-Cl |
| A.0267 | 2-Propenyl | 2-CH₃ | H | SCH₃ | 4-Cl |
| A.0268 | 2-Propenyl | 2-CH₃ | H | SCH₃ | 6-Cl |
| A.0269 | 2-Propenyl | 2-CH₃ | H | SCH₃ | 3-OCH₃ |
| A.0270 | 2-Propenyl | 2-CH₃ | H | SCH₃ | 4-OCH₃ |
| A.0271 | 2-Propenyl | 2-CH₃ | H | SCH₃ | 3-CF₃ |
| A.0272 | 2-Propenyl | 2-CH₃ | H | SCH₃ | 6-CH₃ |
| A.0273 | 2-Propenyl | 2-CH₃ | H | SCH₃ | 6-C₆H₅ |
| A.0274 | (E)-3-Chloro-2-propenyl | 2-CH₃ | H | SCH₃ | H |
| A.0275 | 2-Chloro-2-propenyl | 2-CH₃ | H | SCH₃ | H |
| A.0276 | (E)-2-Butenyl | 2-CH₃ | H | SCH₃ | H |
| A.0277 | 2-Methyl-2-propenyl | 2-CH₃ | H | SCH₃ | H |
| A.0278 | (Z)-3-Chloro-2-butenyl | 2-CH₃ | H | SCH₃ | H |
| A.0279 | 3-Methyl-2-butenyl | 2-CH₃ | H | SCH₃ | H |
| A.0280 | 2-Propynyl | 2-CH₃ | H | SCH₃ | H |
| A.0281 | 2-Propynyl | 2-CH₃ | H | SCH₃ | 3-Cl |
| A.0282 | 2-Propynyl | 2-CH₃ | H | SCH₃ | 4-Cl |
| A.0283 | 2-Propynyl | 2-CH₃ | H | SCH₃ | 6-Cl |
| A.0284 | 2-Propynyl | 2-CH₃ | H | SCH₃ | 3-CH₃ |
| A.0285 | 2-Propynyl | 2-CH₃ | H | SCH₃ | 4-MH |
| A.0286 | 2-Propynyl | 2-CH₃ | H | SCH₃ | 3-CF₃ |
| A.0287 | 2-Propynyl | 2-CH₃ | H | SCH₃ | 6-CH₃ |
| A.0288 | 2-Propynyl | 2-CH₃ | H | SCH₃ | 6-C₆H₅ |
| A.0289 | 2-Butynyl | 2-CH₃ | H | SCH₃ | H |
| A.0290 | 3-Butyn-2-yl | 2-CH₃ | H | SCH₃ | H |
| A.0291 | Cyano-methyl | 2-CH₃ | H | SCH₃ | H |
| A.0292 | Methoxy-carbonyl-methyl | 2-CH₃ | H | SCH₃ | H |
| A.0293 | tert-Butoxy-carbonyl-methyl | 2-CH₃ | H | SCH₃ | H |
| A.0294 | 1-(tert-Butoxy-carbonyl)-ethyl | 2-CH₃ | H | SCH₃ | H |
| A.0295 | Cyclo-propyl-methyl | 2-CH₃ | H | SCH₃ | H |
| A.0296 | 1-Methyl-cyclopentyl | 2-CH₃ | H | SCH₃ | H |
| A.0297 | Cyclohexyl | 2-CH₃ | H | SCH₃ | H |
| A.0298 | 1-Methoxy-propan-2-yl | 2-CH₃ | H | SCH₃ | H |
| A.0299 | Benzyl | 2-CH₃ | H | SCH₃ | H |
| A.0300 | Benzyl | 2-CH₃ | H | SCH₃ | 3-Cl |
| A.0301 | Benzyl | 2-CH₃ | H | SCH₃ | 4-Cl |
| A.0302 | Benzyl | 2-CH₃ | H | SCH₃ | 6-Cl |
| A.0303 | Benzyl | 2-CH₃ | H | SCH₃ | 3-OCH₃ |
| A.0304 | Benzyl | 2-CH₃ | H | SCH₃ | 4-OCH₃ |
| A.0305 | Benzyl | 2-CH₃ | H | SCH₃ | 3-CF₃ |
| A.0306 | Benzyl | 2-CH₃ | H | SCH₃ | 6-CH₃ |
| A.0307 | Benzyl | 2-CH₃ | H | SCH₃ | 6-C₆H₅ |
| A.0308 | 3-Methyl-benzyl | 2-CH₃ | H | SCH₃ | H |
| A.0309 | 2-Fluoro-benzyl | 2-CH₃ | H | SCH₃ | H |
| A.0310 | 3-Fluoro-benzyl | 2-CH₃ | H | SCH₃ | H |
| A.0311 | 4-Chloro-benzyl | 2-CH₃ | H | SCH₃ | H |
| A.0312 | 3,4-Dichloro-benzyl | 2-CH₃ | H | SCH₃ | H |
| A.0313 | 2,6-Difluoro-benzyl | 2-CH₃ | H | SCH₃ | H |
| A.0314 | 3-Trifluoro-methyl-benzyl | 2-CH₃ | H | SCH₃ | H |
| A.0315 | 3-Cyano-benzyl | 2-CH₃ | H | SCH₃ | H |
| A.0316 | 4-Methoxy-benzyl | 2-CH₃ | H | SCH₃ | H |
| A.0317 | 4-Methoxy-carbonyl-benzyl | 2-CH₃ | H | SCH₃ | H |
| A.0318 | 3-Phenyl-benzyl | 2-CH₃ | H | SCH₃ | H |
| A.0319 | (5-Chloro-3-thienyl)-methyl | 2-CH₃ | H | SCH₃ | H |
| A.0320 | (2,5-Dichloro-3-thienyl)- | 2-CH₃ | H | SCH₃ | H |

TABLE A-continued

| No. | R¹ | R² | R³ | R⁴ | R⁵n |
|---|---|---|---|---|---|
| A.0321 | methyl (1,3-Dioxolan-2-yl)methyl | 2-CH₃ | H | SCH₃ | H |
| A.0322 | 1-Phenyl-ethyl | 2-CH₃ | H | SCH₃ | H |
| A.0323 | 1-(4-Methyl-phenyl)-ethyl | 2-CH₃ | H | SCH₃ | H |
| A.0324 | 1-(4-Chloro-phenyl)-ethyl | 2-CH₃ | H | SCH₃ | H |
| A.0325 | 1-(3-Tri-fluoro-methyl-phenyl)-ethyl | 2-CH₃ | H | SCH₃ | H |
| A.0326 | 2-Phenyl-ethyl | 2-CH₃ | H | SCH₃ | H |
| A.0327 | 3-Phenyl-propan-1-yl | 2-CH₃ | H | SCH₃ | H |
| A.0328 | 4-(4-Chloro-phenyl)-2-butenyl | 2-CH₃ | H | SCH₃ | H |
| A.0329 | Methyl | 2-CH₃ | H | Cl | H |
| A.0330 | Methyl | 2-CH₃ | H | Cl | 3-Cl |
| A.0331 | Methyl | 2-CH₃ | H | Cl | 4-Cl |
| A.0332 | Methyl | 2-CH₃ | H | Cl | 6-Cl |
| A.0333 | Methyl | 2-CH₃ | H | Cl | 3-OCH₃ |
| A.0334 | Methyl | 2-CH₃ | H | Cl | 4-OCH₃ |
| A.0335 | Methyl | 2-CH₃ | H | Cl | 3-CF₃ |
| A.0336 | Methyl | 2-CH₃ | H | Cl | 6-CH₃ |
| A.0337 | Methyl | 2-CH₃ | H | Cl | 6-C₆H₅ |
| A.0338 | Ethyl | 2-CH₃ | H | Cl | H |
| A.0339 | n-Propyl | 2-CH₃ | H | Cl | H |
| A.0340 | i-Propyl | 2-CH₃ | H | Cl | H |
| A.0341 | n-Butyl | 2-CH₃ | H | Cl | H |
| A.0342 | i-Butyl | 2-CH₃ | H | Cl | H |
| A.0343 | s-Butyl | 2-CH₃ | H | Cl | H |
| A.0344 | t-Butyl | 2-CH₃ | H | Cl | H |
| A.0345 | n-Pentyl | 2-CH₃ | H | Cl | H |
| A.0346 | n-Hexyl | 2-CH₃ | H | Cl | H |
| A.0347 | 2-Propenyl | 2-CH₃ | H | Cl | H |
| A.0348 | 2-Propenyl | 2-CH₃ | H | Cl | 3-Cl |
| A.0349 | 2-Propenyl | 2-CH₃ | H | Cl | 4-Cl |
| A.0350 | 2-Propenyl | 2-CH₃ | H | Cl | 6-Cl |
| A.0351 | 2-Propenyl | 2-CH₃ | H | Cl | 3-OCH₃ |
| A.0352 | 2-Propenyl | 2-CH₃ | H | Cl | 4-OCH₃ |
| A.0353 | 2-Propenyl | 2-CH₃ | H | Cl | 3-CF₃ |
| A.0354 | 2-Propenyl | 2-CH₃ | H | Cl | 6-CH₃ |
| A.0355 | 2-Propenyl | 2-CH₃ | H | Cl | 6-C₆H₅ |
| A.0356 | (E)-3-Chloro-2-propenyl | 2-CH₃ | H | Cl | H |
| A.0357 | 2-Chloro-2-propenyl | 2-CH₃ | H | Cl | H |
| A.0358 | (E)-2-Butenyl | 2-CH₃ | H | Cl | H |
| A.0359 | 2-Methyl-2-propenyl | 2-CH₃ | H | Cl | H |
| A.0360 | (Z)-3-Chloro-2-butenyl | 2-CH₃ | H | Cl | H |
| A.0361 | 3-Methyl-2-butenyl | 2-CH₃ | H | Cl | H |
| A.0362 | 2-Propynyl | 2-CH₃ | H | Cl | H |
| A.0363 | 2-Propynyl | 2-CH₃ | H | Cl | 3-Cl |
| A.0364 | 2-Propynyl | 2-CH₃ | H | Cl | 4-Cl |
| A.0365 | 2-Propynyl | 2-CH₃ | H | Cl | 6-Cl |
| A.0366 | 2-Propynyl | 2-CH₃ | H | Cl | 3-OCH₃ |
| A.0367 | 2-Propynyl | 2-CH₃ | H | Cl | 4-OCH₃ |
| A.0368 | 2-Propynyl | 2-CH₃ | H | Cl | 3-CF₃ |
| A.0369 | 2-Propynyl | 2-CH₃ | H | Cl | 6-CH₃ |
| A.0370 | 2-Propynyl | 2-CH₃ | H | Cl | 6-C₆H₅ |
| A.0371 | 2-Butynyl | 2-CH₃ | H | Cl | H |
| A.0372 | 3-Butyn-2-yl | 2-CH₃ | H | Cl | H |
| A.0373 | Cyano-methyl | 2-CH₃ | H | Cl | H |
| A.0374 | Methoxy-carbonyl-methyl | 2-CH₃ | H | Cl | H |
| A.0375 | t-Butoxy-carbonyl-methyl | 2-CH₃ | H | Cl | H |
| A.0376 | 1-(t-Butoxy-carbonyl)-ethyl | 2-CH₃ | H | Cl | H |
| A.0377 | Cyclo-propyl-methyl | 2-CH₃ | H | Cl | H |
| A.0378 | 1-Methyl-cyclopentyl | 2-CH₃ | H | Cl | H |
| A.0379 | Cyclohexyl | 2-CH₃ | H | Cl | H |
| A.0380 | 1-Methoxy-propan-2-yl | 2-CH₃ | H | Cl | H |
| A.0381 | Benzyl | 2-CH₃ | H | Cl | H |
| A.0382 | Benzyl | 2-CH₃ | H | Cl | 3-Cl |
| A.0383 | Benzyl | 2-CH₃ | H | Cl | 4-Cl |
| A.0384 | Benzyl | 2-CH₃ | H | Cl | 6-Cl |
| A.0385 | Benzyl | 2-CH₃ | H | Cl | 3-OCH₃ |
| A.0386 | Benzyl | 2-CH₃ | H | Cl | 4-OCH₃ |
| A.0387 | Benzyl | 2-CH₃ | H | Cl | 3-CF₃ |
| A.0388 | Benzyl | 2-CH₃ | H | Cl | 6-CH₃ |
| A.0389 | Benzyl | 2-CH₃ | H | Cl | 6-C₆H₅ |
| A.0390 | 3-Methyl-benzyl | 2-CH₃ | H | Cl | H |
| A.0391 | 2-Fluoro-benzyl | 2-CH₃ | H | Cl | H |
| A.0392 | 3-Fluoro-benzyl | 2-CH₃ | H | Cl | H |
| A.0393 | 4-Chloro-benzyl | 2-CH₃ | H | Cl | H |
| A.0394 | 3,4-Di-chloro-benzyl | 2-CH₃ | H | Cl | H |
| A.0395 | 2,6-di-fluoro-benzyl | 2-CH₃ | H | Cl | H |
| A.0396 | 3-Tri-fluoro-methyl-benzyl | 2-CH₃ | H | Cl | H |
| A.0397 | 3-Cyano-benzyl | 2-CH₃ | H | Cl | H |
| A.0398 | 4-Methoxy-benzyl | 2-CH₃ | H | Cl | H |
| A.0399 | 4-Methoxy-carbonyl-benzyl | 2-CH₃ | H | Cl | H |
| A.0400 | 3-Phenyl-benzyl | 2-CH₃ | H | Cl | H |
| A.0401 | (5-Chloro-3-thienyl)-methyl | 2-CH₃ | H | Cl | H |
| A.0402 | (2,5-Di-chloro-3-thienyl)-methyl | 2-CH₃ | H | Cl | H |
| A.0403 | (1,3-Di-oxolan-2-yl)methyl | 2-CH₃ | H | Cl | H |
| A.0404 | 1-Phenyl-ethyl | 2-CH₃ | H | Cl | H |
| A.0405 | 1-(4-Methyl-phenyl)-ethyl | 2-CH₃ | H | Cl | H |
| A.0406 | 1-(4-Chloro- | 2-CH₃ | H | Cl | H |

TABLE A-continued

| No. | R¹ | R² | R³ | R⁴ | R⁵n |
|---|---|---|---|---|---|
| | phenyl)-ethyl | | | | |
| A.0407 | 1-(3-Trifluoromethylphenyl)-ethyl | 2-CH₃ | H | Cl | H |
| A.0408 | 2-Phenyl-ethyl | 2-CH₃ | H | Cl | H |
| A.0409 | 3-Phenyl-propan-1-yl | 2-CH₃ | H | Cl | H |
| A.0410 | 4-(4-Chlorophenyl)-2-butenyl | 2-CH₃ | H | Cl | H |
| A.0411 | Methyl | 2-CH₃ | H | Br | H |
| A.0412 | Methyl | 2-CH₃ | H | Br | 3-Cl |
| A.0413 | Methyl | 2-CH₃ | H | Br | 4-Cl |
| A.0414 | Methyl | 2-CH₃ | H | Br | 6-Cl |
| A.0415 | Methyl | 2-CH₃ | H | Br | 3-OCH₃ |
| A.0416 | Methyl | 2-CH₃ | H | Br | 4-OCH₃ |
| A.0417 | Methyl | 2-CH₃ | H | Br | 3-CF₃ |
| A.0418 | Methyl | 2-CH₃ | H | Br | 6-CH₃ |
| A.0419 | Methyl | 2-CH₃ | H | Br | 6-C₆H₅ |
| A.0420 | Ethyl | 2-CH₃ | H | Br | H |
| A.0421 | n-Propyl | 2-CH₃ | H | Br | H |
| A.0422 | i-Propyl | 2-CH₃ | H | Br | H |
| A.0423 | n-Butyl | 2-CH₃ | H | Br | H |
| A.0424 | i-Butyl | 2-CH₃ | H | Br | H |
| A.0425 | sec-Butyl | 2-CH₃ | H | Br | H |
| A.0426 | tert-Butyl | 2-CH₃ | H | Br | H |
| A.0427 | n-Pentyl | 2-CH₃ | H | Br | H |
| A.0428 | n-Hexyl | 2-CH₃ | H | Br | H |
| A.0429 | 2-Propenyl | 2-CH₃ | H | Br | H |
| A.0430 | 2-Propenyl | 2-CH₃ | H | Br | 3-Cl |
| A.0431 | 2-Propenyl | 2-CH₃ | H | Br | 4-Cl |
| A.0432 | 2-Propenyl | 2-CH₃ | H | Br | 6-Cl |
| A.0433 | 2-Propenyl | 2-CH₃ | H | Br | 3-OCH₃ |
| A.0434 | 2-Propenyl | 2-CH₃ | H | Br | 4-OCH₃ |
| A.0435 | 2-Propenyl | 2-CH₃ | H | Br | 3-CF₃ |
| A.0436 | 2-Propenyl | 2-CH₃ | H | Br | 6-CH₃ |
| A.0437 | 2-Propenyl | 2-CH₃ | H | Br | 6-C₆H₅ |
| A.0438 | (E)-3-Chloro-2-propenyl | 2-CH₃ | H | Br | H |
| A.0439 | 2-Chloro-2-propenyl | 2-CH₃ | H | Br | H |
| A.0440 | (E)-2-Butenyl | 2-CH₃ | H | Br | H |
| A.0441 | 2-Methyl-2-propenyl | 2-CH₃ | H | Br | H |
| A.0442 | (Z)-3-Chloro-2-butenyl | 2-CH₃ | H | Br | H |
| A.0443 | 3-Methyl-2-butenyl | 2-CH₃ | H | Br | H |
| A.0444 | 2-Propynyl | 2-CH₃ | H | Br | H |
| A.0445 | 2-Propynyl | 2-CH₃ | H | Br | 3-Cl |
| A.0446 | 2-Propynyl | 2-CH₃ | H | Br | 4-Cl |
| A.0447 | 2-Propynyl | 2-CH₃ | H | Br | 6-Cl |
| A.0448 | 2-Propynyl | 2-CH₃ | H | Br | 3-OCH₃ |
| A.0449 | 2-Propynyl | 2-CH₃ | H | Br | 4-OCH₃ |
| A.0450 | 2-Propynyl | 2-CH₃ | H | Br | 3-CF₃ |
| A.0451 | 2-Propynyl | 2-CH₃ | H | Br | 6-CH₃ |
| A.0452 | 2-Propynyl | 2-CH₃ | H | Br | 6-C₆H₅ |
| A.0453 | 2-Butynyl | 2-CH₃ | H | Br | H |
| A.0454 | 3-Butyn-2-yl | 2-CH₃ | H | Br | H |
| A.0455 | Cyanomethyl | 2-CH₃ | H | Br | H |
| A.0456 | Methoxycarbonyl-methyl | 2-CH₃ | H | Br | H |
| A.0457 | tert-Butoxycarbonyl-methyl | 2-CH₃ | H | Br | H |
| A.0458 | 1-(tert-Butoxycarbonyl)-ethyl | 2-CH₃ | H | Br | H |
| A.0459 | Cyclopropyl-methyl | 2-CH₃ | H | Br | H |
| A.0460 | 1-Methyl-cyclopentyl | 2-CH₃ | H | Br | H |
| A.0461 | Cyclohexyl | 2-CH₃ | H | Br | H |
| A.0462 | 1-Methoxy-propan-2-yl | 2-CH₃ | H | Br | H |
| A.0463 | Benzyl | 2-CH₃ | H | Br | H |
| A.0464 | Benzyl | 2-CH₃ | H | Br | 3-Cl |
| A.0465 | Benzyl | 2-CH₃ | H | Br | 4-Cl |
| A.0466 | Benzyl | 2-CH₃ | H | H | 6-Cl |
| A.0467 | Benzyl | 2-CH₃ | H | Br | 3-OCH₃ |
| A.0468 | Benzyl | 2-CH₃ | H | Br | 4-OCH₃ |
| A.0469 | Benzyl | 2-CH₃ | H | Br | 3-CF₃ |
| A.0470 | Benzyl | 2-CH₃ | H | Br | 6-CH₃ |
| A.0471 | Benzyl | 2-CH₃ | H | Br | 6-C₆H₅ |
| A.0472 | 3-Methyl-benzyl | 2-CH₃ | H | Br | H |
| A.0473 | 2-Fluoro-benzyl | 2-CH₃ | H | Br | H |
| A.0474 | 3-Fluoro-benzyl | 2-CH₃ | H | Br | H |
| A.0475 | 4-Chloro-benzyl | 2-CH₃ | H | Br | H |
| A.0476 | 3,4-Dichloro-benzyl | 2-CH₃ | H | Br | H |
| A.0477 | 2,6-Difluoro-benzyl | 2-CH₃ | H | Br | H |
| A.0478 | 3-Trifluoromethyl-benzyl | 2-CH₃ | H | Br | H |
| A.0479 | 3-Cyano-benzyl | 2-CH₃ | H | Br | H |
| A.0480 | 4-Methoxy-benzyl | 2-CH₃ | H | Br | H |
| A.0481 | 4-Methoxy-carbonyl-benzyl | 2-CH₃ | H | Br | H |
| A.0482 | 3-Phenyl-benzyl | 2-CH₃ | H | Br | H |
| A.0483 | (5-Chloro-3-thienyl)-methyl | 2-CH₃ | H | Br | H |
| A.0484 | (2,5-Dichloro-3-thienyl)-methyl | 2-CH₃ | H | Br | H |
| A.0485 | (1,3-Dioxolan-2-yl)methyl | 2-CH₃ | H | Br | H |
| A.0486 | 1-Phenyl-ethyl | 2-CH₃ | H | Br | H |
| A.0487 | 1-(4-Methyl-phenyl)-ethyl | 2-CH₃ | H | Br | H |
| A.0488 | 1-(4-Chlorophenyl)-ethyl | 2-CH₃ | H | Br | H |
| A.0489 | 1-(3-Trifluoromethylphenyl)-ethyl | 2-CH₃ | H | Br | H |
| A.0490 | 2-Phenyl-ethyl | 2-CH₃ | H | Br | H |
| A.0491 | 3-Phenyl-propan-1-yl | 2-CH₃ | H | Br | H |
| A.0492 | 4-(4- | 2-CH₃ | H | Br | H |

TABLE A-continued

| No. | R¹ | R² | R³ | R⁴ | R⁵n |
|---|---|---|---|---|---|
| | Chlorophenyl)-2-butenyl | | | | |
| A.0493 | Methyl | 2-CH₃ | H | CN | H |
| A.0494 | Methyl | 2-CH₃ | H | CN | 3-Cl |
| A.0495 | Methyl | 2-CH₃ | H | CN | 4-Cl |
| A.0496 | Methyl | 2-CH₃ | H | CN | 6-Cl |
| A.0497 | Methyl | 2-CH₃ | H | CN | 3-OCH₃ |
| A.0498 | Methyl | 2-CH₃ | H | CN | 4-OCH₃ |
| A.0499 | Methyl | 2-CH₃ | H | CN | 3-CF₃ |
| A.0500 | Methyl | 2-CH₃ | H | CN | 6-CH₃ |
| A.0501 | Methyl | 2-CH₃ | H | CN | 6-C₆H₅ |
| A.0502 | Ethyl | 2-CH₃ | H | CN | H |
| A.0503 | n-Propyl | 2-CH₃ | H | CN | H |
| A.0504 | i-Propyl | 2-CH₃ | H | CN | H |
| A.0505 | n-Butyl | 2-CH₃ | H | CN | H |
| A.0506 | i-Butyl | 2-CH₃ | H | CN | H |
| A.0507 | sec-Butyl | 2-CH₃ | H | CN | H |
| A.0508 | tert-Butyl | 2-CH₃ | H | CN | H |
| A.0509 | n-Pentyl | 2-CH₃ | H | CN | H |
| A.0510 | n-Hexyl | 2-CH₃ | H | CN | H |
| A.0511 | 2-Propenyl | 2-CH₃ | H | CN | H |
| A.0512 | 2-Propenyl | 2-CH₃ | H | CN | 3-Cl |
| A.0513 | 2-Propenyl | 2-CH₃ | H | CN | 4-Cl |
| A.0514 | 2-Propenyl | 2-CH₃ | H | CN | 6-Cl |
| A.0515 | 2-Propenyl | 2-CH₃ | H | CN | 3-OCH₃ |
| A.0516 | 2-Propenyl | 2-CH₃ | H | CN | 4-OCH₃ |
| A.0517 | 2-Propenyl | 2-CH₃ | H | CN | 3-CF₃ |
| A.0518 | 2-Propenyl | 2-CH₃ | H | CN | 6-CH₃ |
| A.0519 | 2-Propenyl | 2-CH₃ | H | CN | 6-C₆H₅ |
| A.0520 | (E)-3-Chloro-2-propenyl | 2-CH₃ | H | CN | H |
| A.0521 | 2-Chloro-2-propenyl | 2-CH₃ | H | CN | H |
| A.0522 | (E)-2-Butenyl | 2-CH₃ | H | CN | H |
| A.0523 | 2-Methyl-2-propenyl | 2-CH₃ | H | CN | H |
| A.0524 | (Z)-3-Chloro-2-butenyl | 2-CH₃ | H | CN | H |
| A.0525 | 3-Methyl-2-butenyl | 2-CH₃ | H | CN | H |
| A.0526 | 2-Propynyl | 2-CH₃ | H | CN | H |
| A.0527 | 2-Propynyl | 2-CH₃ | H | CN | 3-Cl |
| A.0528 | 2-Propynyl | 2-CH₃ | H | CN | 4-Cl |
| A.0529 | 2-Propynyl | 2-CH₃ | H | CN | 6-Cl |
| A.0530 | 2-Propynyl | 2-CH₃ | H | CN | 3-OCH₃ |
| A.0531 | 2-Propynyl | 2-CH₃ | H | CN | 4-OCH₃ |
| A.0532 | 2-Propynyl | 2-CH₃ | H | CN | 3-CF₃ |
| A.0533 | 2-Propynyl | 2-CH₃ | H | CN | 6-CH₃ |
| A.0534 | 2-Propynyl | 2-CH₃ | H | CN | 6-C₆H₅ |
| A.0535 | 2-Butynyl | 2-CH₃ | H | CN | H |
| A.0536 | 3-Butyn-2-yl | 2-CH₃ | H | CN | H |
| A.0537 | Cyanomethyl | 2-CH₃ | H | CN | H |
| A.0538 | Methoxycarbonylmethyl | 2-CH₃ | H | CN | H |
| A.0539 | tert-Butoxycarbonylmethyl | 2-CH₃ | H | CN | H |
| A.0540 | 1-(tert-Butoxycarbonyl)ethyl | 2-CH₃ | H | CN | H |
| A.0541 | Cyclopropylmethyl | 2-CH₃ | H | CN | H |
| A.0542 | 1-Methylcyclopentyl | 2-CH₃ | H | CN | H |
| A.0543 | cyclohexyl | 2-CH₃ | H | CN | H |
| A.0544 | 1-Methoxypropan-2-yl | 2-CH₃ | H | CN | H |
| A.0545 | Benzyl | 2-CH₃ | H | CN | H |
| A.0546 | Benzyl | 2-CH₃ | H | CN | 3-Cl |
| A.0547 | Benzyl | 2-CH₃ | H | CN | 4-Cl |
| A.0548 | Benzyl | 2-CH₃ | H | CN | 6-Cl |
| A.0549 | Benzyl | 2-CH₃ | H | CN | 3-OCH₃ |
| A.0550 | Benzyl | 2-CH₃ | H | CN | 4-OCH₃ |
| A.0551 | Benzyl | 2-CH₃ | H | CN | 3-CF₃ |
| A.0552 | Benzyl | 2-CH₃ | H | CN | 6-CH₃ |
| A.0553 | Benzyl | 2-CH₃ | H | CN | 6-C₆H₅ |
| A.0554 | 3-Methylbenzyl | 2-CH₃ | H | CN | H |
| A.0555 | 2-Fluorobenzyl | 2-CH₃ | H | CN | H |
| A.0556 | 3-Fluorobenzyl | 2-CH₃ | H | CN | H |
| A.0557 | 4-Chlorobenzyl | 2-CH₃ | H | CN | H |
| A.0558 | 3,4-Dichlorobenzyl | 2-CH₃ | H | CN | H |
| A.0559 | 2,6-Difluorobenzyl | 2-CH₃ | H | CN | H |
| A.0560 | 3-Trifluoromethylbenzyl | 2-CH₃ | H | CN | H |
| A.0561 | 3-Cyanobenzyl | 2-CH₃ | H | CN | H |
| A.0562 | 4-Methoxybenzyl | 2-CH₃ | H | CN | H |
| A.0563 | 4-Methoxycarbonylbenzyl | 2-CH₃ | H | CN | H |
| A.0564 | 3-Phenylbenzyl | 2-CH₃ | H | CN | H |
| A.0565 | (5-Chloro-3-thienyl)methyl | 2-CH₃ | H | CN | H |
| A.0566 | (2,5-Dichloro-3-thienyl)methyl | 2-CH₃ | H | CN | H |
| A.0567 | (1,3-Dioxolan-2-yl)methyl | 2-CH₃ | H | CN | H |
| A.0568 | 1-Phenylethyl | 2-CH₃ | H | CN | H |
| A.0569 | 1-(4-Methylphenyl)ethyl | 2-CH₃ | H | CN | H |
| A.0570 | 1-(4-Chlorophenyl)ethyl | 2-CH₃ | H | CN | H |
| A.0571 | 1-(3-Trifluoromethylphenyl)ethyl | 2-CH₃ | H | CN | H |
| A.0572 | 2-Phenylethyl | 2-CH₃ | H | CN | H |
| A.0573 | 3-Phenylpropan-1-yl | 2-CH₃ | H | CN | H |
| A.0574 | 4-(4-Chlorophenyl)-2-butenyl | 2-CH₃ | H | CN | H |
| A.0575 | Methyl | 2-CH₃ | H | OCH₂C≡CH | H |
| A.0576 | Ethyl | 2-CH₃ | H | OCH₂C≡CH | H |
| A.0577 | 2-Propenyl | 2-CH₃ | H | OCH₂C≡CH | H |
| A.0578 | 2-Propynyl | 2-CH₃ | H | OCH₂C≡CH | H |
| A.0579 | 1-(t-Butoxycarbonyl)ethyl | 2-CH₃ | H | OCH₂C≡CH | H |

TABLE A-continued

| No. | R¹ | R² | R³ | R⁴ | R⁵n |
|---|---|---|---|---|---|
| A.0580 | 3-Methyl-benzyl | 2-CH₃ | H | OCH₂C≡CH | H |
| A.0581 | 1-Phenyl-ethyl | 2-CH₃ | H | OCH₂C≡CH | H |
| A.0582 | Methyl | 2-CH₃ | H | OCH₂CH₂C₆H₅ | H |
| A.0583 | Ethyl | 2-CH₃ | H | OCH₂CH₂C₆H₅ | H |
| A.0584 | 2-Propenyl | 2-CH₃ | H | OCH₂CH₂C₆H₅ | H |
| A.0585 | 2-Propynyl | 2-CH₃ | H | OCH₂CH₂C₆H₅ | H |
| A.0586 | 1-(tert-Butoxy-carbonyl)-ethyl | 2-CH₃ | H | OCH₂CH₂C₆H₅ | H |
| A.0587 | 3-Methyl-benzyl | 2-CH₃ | H | OCH₂CH₂C₆H₅ | H |
| A.0588 | 1-Phenyl-ethyl | 2-CH₃ | H | OCH₂CH₂C₆H₅ | H |
| A.0589 | Methyl | 2-CH₃ | H | SCH₂CH₃ | H |
| A.0590 | Ethyl | 2-CH₃ | H | SCH₂CH₃ | H |
| A.0591 | 2-Propenyl | 2-CH₃ | H | SCH₂CH₃ | H |
| A.0592 | 2-Propynyl | 2-CH₃ | H | SCH₂CH₃ | H |
| A.0593 | 1-(tert-Butoxy-carbonyl)-ethyl | 2-CH₃ | H | SCH₂CH₃ | H |
| A.0594 | 3-Methyl-benzyl | 2-CH₃ | H | SCH₂CH₃ | H |
| A.0595 | 1-Phenyl-ethyl | 2-CH₃ | H | SCH₂CH₃ | H |
| A.0596 | Methyl | 2-CH₃ | H | NHCH₃ | H |
| A.0597 | Ethyl | 2-CH₃ | H | NHCH₃ | H |
| A.0598 | 2-Propenyl | 2-CH₃ | H | NHCH₃ | H |
| A.0599 | 2-Propynyl | 2-CH₃ | H | NHCH₃ | H |
| A.0600 | 1-(tert-Butoxy-carbonyl)-ethyl | 2-CH₃ | H | NHCH₃ | H |
| A.0601 | 3-Methyl-benzyl | 2-CH₃ | H | NHCH₃ | H |
| A.0602 | 1-Phenyl-ethyl | 2-CH₃ | H | NHCH₃ | H |
| A.0603 | Methyl | 2-CH₃ | H | N(CH₃)₂ | H |
| A.0604 | Ethyl | 2-CH₃ | H | N(CH₃)₂ | H |
| A.0605 | 2-Propenyl | 2-CH₃ | H | N(CH₃)₂ | H |
| A.0606 | 2-Propynyl | 2-CH₃ | H | N(CH₃)₂ | H |
| A.0607 | 1-(tert-Butoxy-carbonyl)-ethyl | 2-CH₃ | H | N(CH₃)₂ | H |
| A.0608 | 3-Methyl-benzyl | 2-CH₃ | H | N(CH₃)₂ | H |
| A.0609 | 1-Phenyl-ethyl | 2-CH₃ | H | N(CH₃)₂ | H |
| A.0610 | Methyl | 2-CH₃ | H | OC₆H₅ | H |
| A.0611 | Ethyl | 2-CH₃ | H | OC₆H₅ | H |
| A.0612 | 2-Propenyl | 2-CH₃ | H | OC₆H₅ | H |
| A.0613 | 2-Propynyl | 2-CH₃ | H | OC₆H₅ | H |
| A.0614 | 1-(tert-Butoxy-carbonyl)-ethyl | 2-CH₃ | H | OC₆H₅ | H |
| A.0615 | 3-Methyl-butyl | 2-CH₃ | H | OC₆H₅ | H |
| A.0616 | 1-Phenethyl | 2-CH₃ | H | OC₆H₅ | H |
| A.0617 | Methyl | 2-CH₃ | H | SC₆H₅ | H |
| A.0618 | Ethyl | 2-CH₃ | H | SC₆H₅ | H |
| A.0619 | 2-Propenyl | 2-CH₃ | H | SC₆H₅ | H |
| A.0620 | 2-Propynyl | 2-CH₃ | H | SC₆H₅ | H |
| A.0621 | 1-(tert-Butoxy-carbonyl)-ethyl | 2-CH₃ | H | SC₆H₅ | H |
| A.0622 | 3-Methyl-benzyl | 2-CH₃ | H | SC₆H₅ | H |
| A.0623 | 1-Phenyl-ethyl | 2-CH₃ | H | SC₆H₅ | H |
| A.0624 | Methyl | 2-CH₃ | 5-CH₃ | OCH₃ | H |
| A.0625 | Methyl | 2-CH₃ | 5-CH₃ | OCH₃ | 3-Cl |
| A.0626 | Methyl | 2-CH₃ | 5-CH₃ | OCH₃ | 4-Cl |
| A.0627 | Methyl | 2-CH₃ | 5-CH₃ | OCH₃ | 6-Cl |
| A.0628 | Methyl | 2-CH₃ | 5-CH₃ | OCH₃ | 2-OCH₃ |
| A.0629 | Methyl | 2-CH₃ | 5-CH₃ | OCH₃ | 4-OCH₃ |
| A.0630 | Methyl | 2-CH₃ | 5-CH₃ | OCH₃ | 3-CF₃ |
| A.0631 | Methyl | 2-CH₃ | 5-CH₃ | OCH₃ | 6-CH₃ |
| A.0632 | Methyl | 2-CH₃ | 5-CH₃ | OCH₃ | 6-C₆H₅ |
| A.0633 | Ethyl | 2-CH₃ | 5-CH₃ | OCH₃ | H |
| A.0634 | n-Propyl | 2-CH₃ | 5-CH₃ | OCH₃ | H |
| A.0635 | i-Propyl | 2-CH₃ | 5-CH₃ | OCH₃ | H |
| A.0636 | n-Butyl | 2-CH₃ | 5-CH₃ | OCH₃ | H |
| A.0637 | i-Butyl | 2-CH₃ | 5-CH₃ | OCH₃ | H |
| A.0638 | sec-Butyl | 2-CH₃ | 5-CH₃ | OCH₃ | H |
| A.0639 | tert-Butyl | 2-CH₃ | 5-CH₃ | OCH₃ | H |
| A.0640 | n-Pentyl | 2-CH₃ | 5-CH₃ | OCH₃ | H |
| A.0641 | n-Hexyl | 2-CH₃ | 5-CH₃ | OCH₃ | H |
| A.0642 | 2-Propenyl | 2-CH₃ | 5-CH₃ | OCH₃ | H |
| A.0643 | 2-Propenyl | 2-CH₃ | 5-CH₃ | OCH₃ | 3-Cl |
| A.0644 | 2-Propenyl | 2-CH₃ | 5-CH₃ | OCH₃ | 4-Cl |
| A.0645 | 2-Propenyl | 2-CH₃ | 5-CH₃ | OCH₃ | 6-Cl |
| A.0646 | 2-Propenyl | 2-CH₃ | 5-CH₃ | OCH₃ | 3-OCH₃ |
| A.0647 | 2-Propenyl | 2-CH₃ | 5-CH₃ | OCH₃ | 4-OCH₃ |
| A.0648 | 2-Propenyl | 2-CH₃ | 5-CH₃ | OCH₃ | 3-CF₃ |
| A.0649 | 2-Propenyl | 2-CH₃ | 5-CH₃ | OCH₃ | 6-CH₃ |
| A.0650 | 2-Propenyl | 2-CH₃ | 5-CH₃ | OCH₃ | 6-C₆H₅ |
| A.0651 | (E)-3-Chloro-2-propenyl | 2-CH₃ | 5-CH₃ | OCH₃ | H |
| A.0652 | 2-Chloro-2-propenyl | 2-CH₃ | 5-CH₃ | OCH₃ | H |
| A.0653 | (E)-2-Butenyl | 2-CH₃ | 5-CH₃ | OCH₃ | H |
| A.0654 | 2-Methyl-2-propenyl | 2-CH₃ | 5-CH₃ | OCH₃ | H |
| A.0655 | (Z)-3-Chloro-2-butenyl | 2-CH₃ | 5-CH₃ | OCH₃ | H |
| A.0656 | 3-Methyl-2-butenyl | 2-CH₃ | 5-CH₃ | OCH₃ | H |
| A.0657 | 2-Propynyl | 2-CH₃ | 5-CH₃ | OCH₃ | H |
| A.0658 | 2-Propynyl | 2-CH₃ | 5-CH₃ | OCH₃ | 3-Cl |
| A.0659 | 2-Propynyl | 2-CH₃ | 5-CH₃ | OCH₃ | 4-Cl |
| A.0660 | 2-Propynyl | 2-CH₃ | 5-CH₃ | OCH₃ | 6-Cl |
| A.0661 | 2-Propynyl | 2-CH₃ | 5-CH₃ | OCH₃ | 3-OCH₃ |
| A.0662 | 2-Propynyl | 2-CH₃ | 5-CH₃ | OCH₃ | 4-OCH₃ |
| A.0663 | 2-Propynyl | 2-CH₃ | 5-CH₃ | OCH₃ | 3-CF₃ |
| A.0664 | 2-Propynyl | 2-CH₃ | 5-CH₃ | OCH₃ | 6-CH₃ |
| A.0665 | 2-Propynyl | 2-CH₃ | 5-CH₃ | OCH₃ | 6-C₆H₅ |
| A.0666 | 2-Butynyl | 2-CH₃ | 5-CH₃ | OCH₃ | H |
| A.0667 | 3-Butyn-2-yl | 2-CH₃ | 5-CH₃ | OCH₃ | H |
| A.0668 | Cyano-methyl | 2-CH₃ | 5-CH₃ | OCH₃ | H |
| A.0669 | Methoxy-carbonyl-methyl | 2-CH₃ | 5-CH₃ | OCH₃ | H |
| A.0670 | tert-Butoxy-carbonyl-methyl | 2-CH₃ | 5-CH₃ | OCH₃ | H |
| A.0671 | 1-(tert-Butoxy-carbonyl)-ethyl | 2-CH₃ | 5-CH₃ | OCH₃ | H |
| A.0672 | Cyclo-propyl-methyl | 2-CH₃ | 5-CH₃ | OCH₃ | H |
| A.0673 | 1-Methyl-cyclopentyl | 2-CH₃ | 5-CH₃ | OCH₃ | H |
| A.0674 | Cyclohexyl | 2-CH₃ | 5-CH₃ | OCH₃ | H |
| A.0675 | 1-Methoxy-propan-2-yl | 2-CH₃ | CH₃ | OCH₃ | H |
| A.0676 | Benzyl | 2-CH₃ | 5-CH₃ | OCH₃ | H |
| A.0677 | Benzyl | 2-CH₃ | 5-CH₃ | OCH₃ | 3-Cl |
| A.0678 | Benzyl | 2-CH₃ | 5-CH₃ | OCH₃ | 4-Cl |
| A.0679 | Benzyl | 2-CH₃ | 5-CH₃ | OCH₃ | 6-Cl |
| A.0680 | Benzyl | 2-CH₃ | 5-CH₃ | OCH₃ | 3-OCH₃ |

TABLE A-continued

| No. | R¹ | R² | R³ | R⁴ | R⁵n |
|---|---|---|---|---|---|
| A.0681 | Benzyl | 2-CH₃ | 5-CH₃ | OCH₃ | 4-OCH₃ |
| A.0682 | Benzyl | 2-CH₃ | 5-CH₃ | OCH₃ | 3-CF₃ |
| A.0683 | Benzyl | 2-CH₃ | 5-CH₃ | OCH₃ | 6-CH₃ |
| A.0684 | Benzyl | 2-CH₃ | 5-CH₃ | OCH₃ | 6-C₆H₅ |
| A.0685 | 3-Methyl-benzyl | 2-CH₃ | 5-CH₃ | OCH₃ | H |
| A.0686 | 2-Fluoro-benzyl | 2-CH₃ | 5-CH₃ | OCH₃ | H |
| A.0687 | 3-Fluoro-benzyl | 2-CH₃ | 5-CH₃ | OCH₃ | H |
| A.0688 | 4-Chloro-benzyl | 2-CH₃ | 5-CH₃ | OCH₃ | H |
| A.0689 | 3,4-Di-chloro-benzyl | 2-CH₃ | 5-CH₃ | OCH₃ | H |
| A.0690 | 2,6-Di-fluoro-benzyl | 2-CH₃ | 5-CH₃ | OCH₃ | H |
| A.0691 | 3-Tri-fluoro-methyl-benzyl | 2-CH₃ | 5-CH₃ | OCH₃ | H |
| A.0692 | 3-Cyano-benzyl | 2-CH₃ | 5-CH₃ | OCH₃ | H |
| A.0693 | 4-Methoxy-benzyl | 2-CH₃ | 5-CH₃ | OCH₃ | H |
| A.0694 | 4-Methoxy-carbonyl-benzyl | 2-CH₃ | 5-CH₃ | OCH₃ | H |
| A.0695 | 3-Phenyl-benzyl | 2-CH₃ | 5-CH₃ | OCH₃ | H |
| A.0696 | (5-Chloro-3-thienyl)-methyl | 2-CH₃ | 5-CH₃ | OCH₃ | H |
| A.0697 | (2,5-Di-chloro-3-thienyl)-methyl | 2-CH₃ | 5-CH₃ | OCH₃ | H |
| A.0698 | (1,3-Di-oxolan-2-yl)methyl | 2-CH₃ | 5-CH₃ | OCH₃ | H |
| A.0699 | 1-Phenyl-ethyl | 2-CH₃ | 5-CH₃ | OCH₃ | H |
| A.0700 | 1-(4-Methyl-phenyl)-ethyl | 2-CH₃ | 5-CH₃ | OCH₃ | H |
| A.0701 | 1-(4-Chloro-phenyl)-ethyl | 2-CH₃ | 5-CH₃ | OCH₃ | H |
| A.0702 | 1-(3-Tri-fluoro-methyl-phenyl)-ethyl | 2-CH₃ | 5-CH₃ | OCH₃ | H |
| A.0703 | 2-Phenyl-ethyl | 2-CH₃ | 5-CH₃ | OCH₃ | H |
| A.0704 | 3-Phenyl-propan-1-yl | 2-CH₃ | 5-CH₃ | OCH₃ | H |
| A.0705 | 4-(4-Chloro-phenyl)-2-butenyl | 2-CH₃ | 5-CH₃ | OCH₃ | H |
| A.0706 | Methyl | 2-CH₃ | 5-CH₃ | OC₂H₅ | H |
| A.0707 | Methyl | 2-CH₃ | 5-CH₃ | OC₂H₅ | 3-Cl |
| A.0708 | Methyl | 2-CH₃ | 5-CH₃ | OC₂H₅ | 4-Cl |
| A.0709 | Methyl | 2-CH₃ | 5-CH₃ | OC₂H₅ | 6-Cl |
| A.0710 | Methyl | 2-CH₃ | 5-CH₃ | OC₂H₅ | 3-OCH₃ |
| A.0711 | Methyl | 2-CH₃ | 5-CH₃ | OC₂H₅ | 4-OCH₃ |
| A.0712 | Methyl | 2-CH₃ | 5-CH₃ | OC₂H₅ | 3-CF₃ |
| A.0713 | Methyl | 2-CH₃ | 5-CH₃ | OC₂H₅ | 6-CH₃ |
| A.0714 | Methyl | 2-CH₃ | 5-CH₃ | OC₂H₅ | 6-C₆H₅ |
| A.0715 | Ethyl | 2-CH₃ | 5-CH₃ | OC₂H₅ | H |
| A.0716 | n-Propyl | 2-CH₃ | 5-CH₃ | OC₂H₅ | H |
| A.0717 | i-Propyl | 2-CH₃ | 5-CH₃ | OC₂H₅ | H |
| A.0718 | n-Butyl | 2-CH₃ | 5-CH₃ | OC₂H₅ | H |
| A.0719 | i-Butyl | 2-CH₃ | 5-CH₃ | OC₂H₅ | H |
| A.0720 | sec-Butyl | 2-CH₃ | 5-CH₃ | OC₂H₅ | H |
| A.0721 | tert-Butyl | 2-CH₃ | 5-CH₃ | OC₂H₅ | H |
| A.0722 | s-Pentyl | 2-CH₃ | 5-CH₃ | OC₂H₅ | H |
| A.0723 | n-Hexyl | 2-CH₃ | 5-CH₃ | OC₂H₅ | H |
| A.0724 | 2-Propenyl | 2-CH₃ | 5-CH₃ | OC₂H₅ | H |
| A.0725 | 2-Propenyl | 2-CH₃ | 5-CH₃ | OC₂H₅ | 3-Cl |
| A.0726 | 2-Propenyl | 2-CH₃ | 5-CH₃ | OC₂H₅ | 4-Cl |
| A.0727 | 2-Propenyl | 2-CH₃ | 5-CH₃ | OC₂H₅ | 6-Cl |
| A.0728 | 2-Propenyl | 2-CH₃ | 5-CH₃ | OC₂H₅ | 3-OCH₃ |
| A.0729 | 2-Propenyl | 2-CH₃ | 5-CH₃ | OC₂H₅ | 4-OCH₃ |
| A.0730 | 2-Propenyl | 2-CH₃ | 5-CH₃ | OC₂H₅ | 3-CF₃ |
| A.0731 | 2-Propenyl | 2-CH₃ | 5-CH₃ | OC₂H₅ | 6-CH₃ |
| A.0732 | 2-Propenyl | 2-CH₃ | 5-CH₃ | OC₂H₅ | 6-C₆H₅ |
| A.0733 | (E)-3-Chloro-2-propenyl | 2-CH₃ | 5-CH₃ | OC₂H₅ | H |
| A.0734 | 2-Chloro-2-propenyl | 2-CH₃ | 5-CH₃ | OC₂H₅ | H |
| A.0735 | (E)-2-Butenyl | 2-CH₃ | 5-CH₃ | OC₂H₅ | H |
| A.0736 | 2-Methyl-2-propenyl | 2-CH₃ | 5-CH₃ | OC₂H₅ | H |
| A.0737 | (Z)-3-Chloro-2-butenyl | 2-CH₃ | 5-CH₃ | OC₂H₅ | H |
| A.0738 | 3-Methyl-2-butenyl | 2-CH₃ | 5-CH₃ | OC₂H₅ | H |
| A.0739 | 2-Propynyl | 2-CH₃ | 5-CH₃ | OC₂H₅ | H |
| A.0740 | 2-Propynyl | 2-CH₃ | 5-CH₃ | OC₂H₅ | 3-Cl |
| A.0741 | 2-Propynyl | 2-CH₃ | 5-CH₃ | OC₂H₅ | 4-Cl |
| A.0742 | 2-Propynyl | 2-CH₃ | 5-CH₃ | OC₂H₅ | 6-Cl |
| A.0743 | 2-Propynyl | 2-CH₃ | 5-CH₃ | OC₂H₅ | 3-OCH₃ |
| A.0744 | 2-Propynyl | 2-CH₃ | 5-CH₃ | OC₂H₅ | 4-OCH₃ |
| A.0745 | 2-Propynyl | 2-CH₃ | 5-CH₃ | OC₂H₅ | 3-CF₃ |
| A.0746 | 2-Propynyl | 2-CH₃ | 5-CH₃ | OC₂H₅ | 6-CH₃ |
| A.0747 | 2-Propynyl | 2-CH₃ | 5-CH₃ | OC₂H₅ | 6-C₆H₅ |
| A.0748 | 2-Butynyl | 2-CH₃ | 5-CH₃ | OC₂H₅ | H |
| A.0749 | 3-Butyn-2-yl | 2-CH₃ | 5-CH₃ | OC₂H₅ | H |
| A.0750 | Cyano-methyl | 2-CH₃ | 5-CH₃ | OC₂H₅ | H |
| A.0751 | Methoxy-carbonyl-methyl | 2-CH₃ | 5-CH₃ | OC₂H₅ | H |
| A.0752 | tert-Butoxy-carbonyl-methyl | 2-CH₃ | 5-CH₃ | OC₂H₅ | H |
| A.0753 | 1-(tert-Butoxy-carbonyl)-ethyl | 2-CH₃ | 5-CH₃ | OC₂H₅ | H |
| A.0754 | Cyclo-propyl-methyl | 2-CH₃ | 5-CH₃ | OC₂H₅ | H |
| A.0755 | 1-Methyl-cyclopentyl | 2-CH₃ | 5-CH₃ | OC₂H₅ | H |
| A.0756 | Cyclohexyl | 2-CH₃ | 5-CH₃ | OC₂H₅ | H |
| A.0757 | 1-Methoxy-propan-2-yl | 2-CH₃ | 5-CH₃ | OC₂H₅ | H |
| A.0758 | Benzyl | 2-CH₃ | 5-CH₃ | OC₂H₅ | H |
| A.0759 | Benzyl | 2-CH₃ | 5-CH₃ | OC₂H₅ | 3-Cl |
| A.0760 | Benzyl | 2-CH₃ | 5-CH₃ | OC₂H₅ | 4-Cl |
| A.0761 | Benzyl | 2-CH₃ | 5-CH₃ | OC₂H₅ | 6-Cl |
| A.0762 | Benzyl | 2-CH₃ | 5-CH₃ | OC₂H₅ | 3-OCH₃ |
| A.0763 | Benzyl | 2-CH₃ | 5-CH₃ | OC₂H₅ | 4-OCH₃ |
| A.0764 | Benzyl | 2-CH₃ | 5-CH₃ | OC₂H₅ | 3-CF₃ |
| A.0765 | Benzyl | 2-CH₃ | 5-CH₃ | OC₂H₅ | 6-CH₃ |
| A.0766 | Benzyl | 2-CH₃ | 5-CH₃ | OC₂H₅ | 6-C₆H₅ |
| A.0767 | Benzyl | 2-CH₃ | 5-CH₃ | OC₂H₅ | 5-Cl |
| A.0768 | 3-Methyl-benzyl | CH₃ | CH₃ | OC₂H₅ | H |
| A.0769 | 2-Fluoro-benzyl | CH₃ | CH₃ | OC₂H₅ | H |
| A.0770 | 3-Fluoro-benzyl | CH₃ | CH₃ | OC₂H₅ | H |

TABLE A-continued

| No. | R¹ | R² | R³ | R⁴ | R⁵n |
|---|---|---|---|---|---|
| A.0771 | 4-Chlorobenzyl | CH₃ | CH₃ | OC₂H₅ | H |
| A.0772 | 3,4-Dichlorobenzyl | CH₃ | CH₃ | OC₂H₅ | H |
| A.0773 | 2,6-Difluorobenzyl | CH₃ | CH₃ | OC₂H₅ | H |
| A.0774 | 3-Trifluoromethylbenzyl | CH₃ | CH₃ | OC₂H₅ | H |
| A.0775 | 3-Cyanobenzyl | CH₃ | CH₃ | OC₂H₅ | H |
| A.0776 | 4-Methoxybenzyl | CH₃ | CH₃ | OC₂H₅ | H |
| A.0777 | 4-Methoxycarbonylbenzyl | CH₃ | CH₃ | OC₂H₅ | H |
| A.0778 | 3-Phenylbenzyl | CH₃ | CH₃ | OC₂H₅ | H |
| A.0779 | (5-Chloro-3-thienyl)methyl | CH₃ | CH₃ | OC₂H₅ | H |
| A.0780 | (2,5-Dichloro-3-thienyl)methyl | CH₃ | CH₃ | OC₂H₅ | H |
| A.0781 | (1,3-Dioxolan-2-yl)methyl | CH₃ | CH₃ | OC₂H₅ | H |
| A.0782 | 1-Phenylethyl | CH₃ | CH₃ | OC₂H₅ | H |
| A.0783 | 1-(4-Methylphenyl)ethyl | CH₃ | CH₃ | OC₂H₅ | H |
| A.0784 | 1-(4-Chlorophenyl)ethyl | CH₃ | CH₃ | OC₂H₅ | H |
| A.0785 | 1-(3-Trifluoromethylphenyl)ethyl | CH₃ | CH₃ | OC₂H₅ | H |
| A.0786 | 2-Phenylethyl | CH₃ | CH₃ | OC₂H₅ | H |
| A.0787 | 3-Phenylpropan-1-yl | CH₃ | CH₃ | OC₂H₅ | H |
| A.0788 | 4-(4-Chlorophenyl)-2-butenyl | CH₃ | CH₃ | OC₂H₅ | H |
| A.0789 | Methyl | CH₃ | CH₃ | OCH₂CH=CH₂ | H |
| A.0790 | Methyl | CH₃ | CH₃ | OCH₂CH=CH₂ | H |
| A.0791 | Methyl | CH₃ | CH₃ | OCH₂CH=CH₂ | 4-Cl |
| A.0792 | Methyl | CH₃ | CH₃ | OCH₂CH=CH₂ | 6-Cl |
| A.0793 | Methyl | CH₃ | CH₃ | OCH₂CH=CH₂ | 3-OCH₃ |
| A.0794 | Methyl | CH₃ | CH₃ | OCH₂CH=CH₂ | 4-OCH₃ |
| A.0795 | Methyl | CH₃ | CH₃ | OCH₂CH=CH₂ | 3-CF₃ |
| A.0796 | Methyl | CH₃ | CH₃ | OCH₂CH=CH₂ | 6-CH₃ |
| A.0797 | Methyl | CH₃ | CH₃ | OCH₂CH=CH₂ | 6-C₆H₅ |
| A.0798 | Ethyl | CH₃ | CH₃ | OCH₂CH=CH₂ | H |
| A.0799 | n-Propyl | CH₃ | CH₃ | OCH₂CH=CH₂ | H |
| A.0800 | i-Propyl | CH₃ | CH₃ | OCH₂CH=CH₂ | H |
| A.0801 | n-Butyl | CH₃ | CH₃ | OCH₂CH=CH₂ | H |
| A.0802 | i-Butyl | CH₃ | CH₃ | OCH₂CH=CH₂ | H |
| A.0803 | sec-Butyl | CH₃ | CH₃ | OCH₂CH=CH₂ | H |
| A.0804 | tert-Butyl | CH₃ | CH₃ | OCH₂CH=CH₂ | H |
| A.0805 | n-Pentyl | CH₃ | CH₃ | OCH₂CH=CH₂ | H |
| A.0806 | n-Hexyl | CH₃ | CH₃ | OCH₂CH=CH₂ | H |
| A.0807 | 2-Propenyl | CH₃ | CH₃ | OCH₂CH=CH₂ | H |
| A.0808 | 2-Propenyl | CH₃ | CH₃ | OCH₂CH=CH₂ | 3-Cl |
| A.0809 | 2-Propenyl | CH₃ | CH₃ | OCH₂CH=CH₂ | 4-Cl |
| A.0810 | 2-Propenyl | CH₃ | CH₃ | OCH₂CH=CH₂ | 6-Cl |
| A.0811 | 2-Propenyl | CH₃ | CH₃ | OCH₂CH=CH₂ | 3-OCH₃ |
| A.0812 | 2-Propenyl | CH₃ | CH₃ | OCH₂CH=CH₂ | 4-OCH₃ |
| A.0813 | 2-Propenyl | CH₃ | CH₃ | OCH₂CH=CH₂ | 3-CF₃ |
| A.0814 | 2-Propenyl | CH₃ | CH₃ | OCH₂CH=CH₂ | 6-CH₃ |
| A.0815 | 2-Propenyl | CH₃ | CH₃ | OCH₂CH=CH₂ | 6-C₆H₅ |
| A.0816 | (E)-3-Chloro-2-propenyl | CH₃ | CH₃ | OCH₂CH=CH₂ | H |
| A.0817 | 2-Chloro-2-propenyl | CH₃ | CH₃ | OCH₂CH=CH₂ | H |
| A.0818 | (E)-2-Butenyl | CH₃ | CH₃ | OCH₂CH=CH₂ | H |
| A.0819 | 2-Methyl-2-propenyl | CH₃ | CH₃ | OCH₂CH=CH₂ | H |
| A.0820 | (Z)-3-Chloro-2-butenyl | CH₃ | CH₃ | OCH₂CH=CH₂ | H |
| A.0821 | 3-Methyl-2-butenyl | CH₃ | CH₃ | OCH₂CH=CH₂ | H |
| A.0822 | 2-Propynyl | CH₃ | CH₃ | OCH₂CH=CH₂ | H |
| A.0823 | 2-Propynyl | CH₃ | CH₃ | OCH₂CH=CH₂ | 3-Cl |
| A.0824 | 2-Propynyl | CH₃ | CH₃ | OCH₂CH=CH₂ | 4-Cl |
| A.0825 | 2-Propynyl | CH₃ | CH₃ | OCH₂CH=CH₂ | 6-Cl |
| A.0826 | 2-Propynyl | CH₃ | CH₃ | OCH₂CH=CH₂ | 3-OCH₃ |
| A.0827 | 2-Propynyl | CH₃ | CH₃ | OCH₂CH=CH₂ | 4-OCH₃ |
| A.0828 | 2-Propynyl | CH₃ | CH₃ | OCH₂CH=CH₂ | 3-CF₃ |
| A.0829 | 2-Propynyl | CH₃ | CH₃ | OCH₂CH=CH₂ | 6-CH₃ |
| A.0830 | 2-Propynyl | CH₃ | CH₃ | OCH₂CH=CH₂ | 6-C₆H₅ |
| A.0831 | 2-Butynyl | CH₃ | CH₃ | OCH₂CH=CH₂ | H |
| A.0832 | 3-Butyn-2-yl | CH₃ | CH₃ | OCH₂CH=CH₂ | H |
| A.0833 | Cyanomethyl | CH₃ | CH₃ | OCH₂CH=CH₂ | H |
| A.0834 | Methoxycarbonylmethyl | CH₃ | CH₃ | OCH₂CH=CH₂ | H |
| A.0835 | t-Butoxycarbonylmethyl | CH₃ | CH₃ | OCH₂CH=CH₂ | H |
| A.0836 | 1-(t-Butoxycarbonyl)ethyl | CH₃ | CH₃ | OCH₂CH=CH₂ | H |
| A.0837 | Cyclopropylmethyl | CH₃ | CH₃ | OCH₂CH=CH₂ | H |
| A.0838 | 1-Methylcyclopentyl | CH₃ | CH₃ | OCH₂CH=CH₂ | H |
| A.0839 | Cyclohexyl | CH₃ | CH₃ | OCH₂CH=CH₂ | H |
| A.0840 | 1-methoxypropan-2-yl | CH₃ | CH₃ | OCH₂CH=CH₂ | H |
| A.0841 | Benzyl | CH₃ | CH₃ | OCH₂CH=CH₂ | H |
| A.0842 | Benzyl | CH₃ | CH₃ | OCH₂CH=CH₂ | 3-Cl |
| A.0843 | Benzyl | CH₃ | CH₃ | OCH₂CH=CH₂ | 4-Cl |
| A.0844 | Benzyl | CH₃ | CH₃ | OCH₂CH=CH₂ | 6-Cl |
| A.0845 | Benzyl | CH₃ | CH₃ | OCH₂CH=CH₂ | 3-OCH₃ |
| A.0846 | Benzyl | CH₃ | CH₃ | OCH₂CH=CH₂ | 4-OCH₃ |
| A.0847 | Benzyl | CH₃ | CH₃ | OCH₂CH=CH₂ | 3-CF₃ |
| A.0848 | Benzyl | CH₃ | CH₃ | OCH₂CH=CH₂ | 6-CH₃ |
| A.0849 | Benzyl | CH₃ | CH₃ | OCH₂CH=CH₂ | 6-C₆H₅ |
| A.0850 | 3-Methylbenzyl | CH₃ | CH₃ | OCH₂CH=CH₂ | H |
| A.0851 | 2-Fluorobenzyl | CH₃ | CH₃ | OCH₂CH=CH₂ | H |
| A.0852 | 3-Fluorobenzyl | CH₃ | CH₃ | OCH₂CH=CH₂ | H |
| A.0853 | 4-Chlorobenzyl | CH₃ | CH₃ | OCH₂CH=CH₂ | H |
| A.0954 | 3,4-Dichlorobenzyl | CH₃ | CH₃ | OCH₂CH=CH₂ | H |
| A.0855 | 2,6-Difluorobenzyl | CH₃ | CH₃ | OCH₂CH=CH₂ | H |
| A.0856 | 3-Trifluoromethylbenzyl | CH₃ | CH₃ | OCH₂CH=CH₂ | H |

TABLE A-continued

| No. | R¹ | R² | R³ | R⁴ | R⁵n |
|---|---|---|---|---|---|
| A.0857 | 3-Cyanobenzyl | CH₃ | CH₃ | OCH₂CH=CH₂ | H |
| A.0858 | 4-Methoxybenzyl | CH₃ | CH₃ | OCH₂CH=CH₂ | H |
| A.0859 | 4-Methoxycarbonylbenzyl | CH₃ | CH₃ | OCH₂CH=CH₂ | H |
| A.0860 | 3-phenylbenzyl | CH₃ | CH₃ | OCH₂CH=CH₂ | H |
| A.0861 | (5-Chloro-3-thienyl)methyl | CH₃ | CH₃ | OCH₂CH=CH₂ | H |
| A.0862 | (2,5-Dichloro-3-thienyl)methyl | CH₃ | CH₃ | OCH₂CH=CH₂ | H |
| A.0863 | (1,3-Dioxolan-2-yl)methyl | CH₃ | CH₃ | OCH₂CH=CH₂ | H |
| A.0864 | 1-Phenylethyl | CH₃ | CH₃ | OCH₂CH=CH₂ | H |
| A.0865 | 1-(4-Methylphenyl)ethyl | CH₃ | CH₃ | OCH₂CH=CH₂ | H |
| A.0866 | 1-(4-Chlorophenyl)ethyl | CH₃ | CH₃ | OCH₂CH=CH₂ | H |
| A.0867 | 1-(3-Trifluoromethylphenyl)ethyl | CH₃ | CH₃ | OCH₂CH=CH₂ | H |
| A.0868 | 2-Phenylethyl | CH₃ | CH₃ | OCH₂CH=CH₂ | H |
| A.0869 | 3-Phenylpropan-1-yl | CH₃ | CH₃ | OCH₂CH=CH₂ | H |
| A.0870 | 4-(4-Chlorophenyl)-2-butenyl | CH₃ | CH₃ | OCH₂CH=CH₂ | H |
| A.0871 | Methyl | CH₃ | CH₃ | SCH₃ | H |
| A.0872 | Methyl | CH₃ | CH₃ | SCH₃ | 3-Cl₃ |
| A.0873 | Methyl | CH₃ | CH₃ | SCH₃ | 4-Cl |
| A.0874 | Methyl | CH₃ | CH₃ | SCH₃ | 6-Cl |
| A.0875 | Methyl | CH₃ | CH₃ | SCH₃ | 3-OCH₃ |
| A.0876 | Methyl | CH₃ | CH₃ | SCH₃ | 4-OCH₃ |
| A.0877 | Methyl | CH₃ | CH₃ | SCH₃ | 3-CF₃ |
| A.0878 | Methyl | CH₃ | CH₃ | SCH₃ | 6-CH₃ |
| A.0879 | Methyl | CH₃ | CH₃ | SCH₃ | 6-C₆H₅ |
| A.0880 | Ethyl | CH₃ | CH₃ | SCH₃ | H |
| A.0881 | n-Propyl | CH₃ | CH₃ | SCH₃ | H |
| A.0882 | i-Propyl | CH₃ | CH₃ | SCH₃ | H |
| A.0883 | n-Butyl | CH₃ | CH₃ | SCH₃ | H |
| A.0884 | i-Butyl | CH₃ | CH₃ | SCH₃ | H |
| A.0885 | s-Butyl | CH₃ | CH₃ | SCH₃ | H |
| A.0886 | t-Butyl | CH₃ | CH₃ | SCH₃ | H |
| A.0887 | n-Pentyl | CH₃ | CH₃ | SCH₃ | H |
| A.0888 | n-Hexyl | CH₃ | CH₃ | SCH₃ | H |
| A.0889 | 2-Propenyl | CH₃ | CH₃ | SCH₃ | H |
| A.0890 | 2-Propenyl | CH₃ | CH₃ | SCH₃ | 3-Cl |
| A.0891 | 2-Propenyl | CH₃ | CH₃ | SCH₃ | 4-Cl |
| A.0892 | 2-Propenyl | CH₃ | CH₃ | SCH₃ | 6-Cl |
| A.0893 | 2-Propenyl | CH₃ | CH₃ | SCH₃ | 3-OCH₃ |
| A.0894 | 2-Propenyl | CH₃ | CH₃ | SCH₃ | 4-OCH₃ |
| A.0895 | 2-Propenyl | CH₃ | CH₃ | SCH₃ | 3-CF₃ |
| A.0896 | 2-Propenyl | CH₃ | CH₃ | SCH₃ | 6-CH₃ |
| A.0897 | 2-Propenyl | CH₃ | CH₃ | SCH₃ | 6-C₆H₅ |
| A.0898 | (E)-3-Chloro-2-propenyl | CH₃ | CH₃ | SCH₃ | H |
| A.0899 | 2-Chloro-2-propenyl | CH₃ | CH₃ | SCH₃ | H |
| A.0900 | (E)-2-Butenyl | CH₃ | CH₃ | SCH₃ | H |
| A.0901 | 2-Methyl-2-propenyl | CH₃ | CH₃ | SCH₃ | H |
| A.0902 | (Z)-3-Chloro-2-butenyl | CH₃ | CH₃ | SCH₃ | H |
| A.0903 | 3-Methyl-2-butenyl | CH₃ | CH₃ | SCH₃ | H |
| A.0904 | 2-Propynyl | CH₃ | CH₃ | SCH₃ | H |
| A.0905 | 2-Propynyl | CH₃ | CH₃ | SCH₃ | 3-Cl |
| A.0906 | 2-Propynyl | CH₃ | CH₃ | SCH₃ | 4-Cl |
| A.0907 | 2-Propynyl | CH₃ | CH₃ | SCH₃ | 6-Cl |
| A.0908 | 2-Propynyl | CH₃ | CH₃ | SCH₃ | 3-OCH₃ |
| A.0909 | 2-Propynyl | CH₃ | CH₃ | SCH₃ | 4-OCH₃ |
| A.0910 | 2-Propynyl | CH₃ | CH₃ | SCH₃ | 3-CF₃ |
| A.0911 | 2-Propynyl | CH₃ | CH₃ | SCH₃ | 6-CH₃ |
| A.0912 | 2-Propynyl | CH₃ | CH₃ | SCH₃ | 6-C₆H₅ |
| A.0913 | 2-Butynyl | CH₃ | CH₃ | SCH₃ | H |
| A.0914 | 3-Butyn-2-yl | CH₃ | CH₃ | SCH₃ | H |
| A.0915 | Cyanomethyl | CH₃ | CH₃ | SCH₃ | H |
| A.0916 | Methoxycarbonylmethyl | CH₃ | CH₃ | SCH₃ | H |
| A.0917 | t-Butoxycarbonylmethyl | CH₃ | CH₃ | SCH₃ | H |
| A.0918 | 1-(t-Butoxycarbonyl)ethyl | CH₃ | CH₃ | SCH₃ | H |
| A.0919 | Cyclopropylmethyl | CH₃ | CH₃ | SCH₃ | H |
| A.0920 | 1-Methylcyclopentyl | CH₃ | CH₃ | SCH₃ | H |
| A.0921 | Cyclohexyl | CH₃ | CH₃ | SCH₃ | H |
| A.0922 | 1-Methoxypropan-2-yl | CH₃ | CH₃ | SCH₃ | H |
| A.0923 | Benzyl | CH₃ | CH₃ | SCH₃ | H |
| A.0924 | Benzyl | CH₃ | CH₃ | SCH₃ | 3-Cl |
| A.0925 | Benzyl | CH₃ | CH₃ | SCH₃ | 4-Cl |
| A.0926 | Benzyl | CH₃ | CH₃ | SCH₃ | 6-Cl |
| A.0927 | Benzyl | CH₃ | CH₃ | SCH₃ | 3-OCH₃ |
| A.0928 | Benzyl | CH₃ | CH₃ | SCH₃ | 4-OCH₃ |
| A.0929 | Benzyl | CH₃ | CH₃ | SCH₃ | 3-CF₃ |
| A.0930 | Benzyl | CH₃ | CH₃ | SCH₃ | 6-CH₃ |
| A.0931 | Benzyl | CH₃ | CH₃ | SCH₃ | 6-C₆H₅ |
| A.0932 | 3-Methylbenzyl | CH₃ | CH₃ | SCH₃ | H |
| A.0933 | 2-Fluorobenzyl | CH₃ | CH₃ | SCH₃ | H |
| A.0934 | 3-Fluorobenzyl | CH₃ | CH₃ | SCH₃ | H |
| A.0935 | 4-Chlorobenzyl | CH₃ | CH₃ | SCH₃ | H |
| A.0936 | 3,4-Dichlorobenzyl | CH₃ | CH₃ | SCH₃ | H |
| A.0937 | 2,6-Difluorobenzyl | CH₃ | CH₃ | SCH₃ | H |
| A.0938 | 3-Trifluoromethylbenzyl | CH₃ | CH₃ | SCH₃ | H |
| A.0939 | 3-Cyanobenzyl | CH₃ | CH₃ | SCH₃ | H |
| A.0940 | 4-Methoxybenzyl | CH₃ | CH₃ | SCH₃ | H |
| A.0941 | 4-Methoxycarbonylbenzyl | CH₃ | CH₃ | SCH₃ | H |
| A.0942 | 3-Phenylbenzyl | CH₃ | CH₃ | SCH₃ | H |
| A.0943 | (5-Chloro-3-thienyl)methyl | CH₃ | CH₃ | SCH₃ | H |

TABLE A-continued

| No. | R¹ | R² | R³ | R⁴ | R⁵n |
|---|---|---|---|---|---|
| A.0944 | (2,5-Dichloro-3-thienyl)-methyl | CH₃ | CH₃ | SCH₃ | H |
| A.0945 | (1,3-Dioxolan-2-yl)methyl | CH₃ | CH₃ | SCH₃ | H |
| A.0946 | 1-Phenylethyl | CH₃ | CH₃ | SCH₃ | H |
| A.0947 | 1-(4-Methylphenyl)-ethyl | CH₃ | CH₃ | SCH₃ | H |
| A.0948 | 1-(4-Chlorophenyl)-ethyl | CH₃ | CH₃ | SCH₃ | H |
| A.0949 | 1-(3-Trifluoromethylphenyl)-ethyl | CH₃ | CH₃ | SCH₃ | H |
| A.0950 | 2-Phenylethyl | CH₃ | CH₃ | SCH₃ | H |
| A.0951 | 3-Phenyl-propan-1-yl | CH₃ | CH₃ | SCH₃ | H |
| A.0952 | 4-(4-Chlorophenyl)-2-butenyl | CH₃ | CH₃ | SCH₃ | H |
| A.0953 | Methyl | CH₃ | CH₃ | Cl | H₃ |
| A.0954 | Methyl | CH₃ | CH₃ | Cl | 3-Cl |
| A.0955 | Methyl | CH₃ | CH₃ | Cl | 4-Cl |
| A.0956 | Methyl | CH₃ | CH₃ | Cl | 6-Cl |
| A.0957 | Methyl | CH₃ | CH₃ | Cl | 3-OCH₃ |
| A.0958 | Methyl | CH₃ | CH₃ | Cl | 4-OCH₃ |
| A.0959 | Methyl | CH₃ | CH₃ | Cl | 3-CF₃ |
| A.0960 | Methyl | CH₃ | CH₃ | Cl | 6-CH₃ |
| A.0961 | Methyl | CH₃ | CH₃ | Cl | 6-C₆H₅ |
| A.0962 | Ethyl | CH₃ | CH₃ | Cl | H |
| A.0963 | n-Propyl | CH₃ | CH₃ | Cl | H |
| A.0964 | i-Propyl | CH₃ | CH₃ | Cl | H |
| A.0965 | n-Butyl | CH₃ | CH₃ | Cl | H |
| A.0966 | i-Butyl | CH₃ | CH₃ | Cl | H |
| A.0967 | s-Butyl | CH₃ | CH₃ | Cl | H |
| A.0968 | t-Butyl | CH₃ | CH₃ | Cl | H |
| A.0969 | n-Pentyl | CH₃ | CH₃ | Cl | H |
| A.0970 | n-Hexyl | CH₃ | CH₃ | Cl | H |
| A.0971 | 2-Propenyl | CH₃ | CH₃ | Cl | H |
| A.0972 | 2-Propenyl | CH₃ | CH₃ | Cl | 3-Cl |
| A.0973 | 2-Propenyl | CH₃ | CH₃ | Cl | 4-Cl |
| A.0974 | 2-Propenyl | CH₃ | CH₃ | Cl | 6-Cl |
| A.0975 | 2-Propenyl | CH₃ | CH₃ | Cl | 3-OCH₃ |
| A.0976 | 2-Propenyl | CH₃ | CH₃ | Cl | 4-OCH₃ |
| A.0977 | 2-Propenyl | CH₃ | CH₃ | Cl | 3-CF₃ |
| A.0978 | 2-Propenyl | CH₃ | CH₃ | Cl | 6-CH₃ |
| A.0979 | 2-Propenyl | CH₃ | CH₃ | Cl | 6-C₆H₅ |
| A.0980 | (E)-3-Chloro-2-propenyl | CH₃ | CH₃ | Cl | H |
| A.0981 | 2-Chloro-2-propenyl | CH₃ | CH₃ | Cl | H |
| A.0982 | (E)-2-Butenyl | CH₃ | CH₃ | Cl | H |
| A.0983 | 2-Methyl-2-propenyl | CH₃ | CH₃ | Cl | H |
| A.0984 | (Z)-3-Chloro-2-butenyl | CH₃ | CH₃ | Cl | H |
| A.0985 | 3-Methyl-2-butenyl | CH₃ | CH₃ | Cl | H |
| A.0986 | 2-Propynyl | CH₃ | CH₃ | Cl | H |
| A.0987 | 2-Propynyl | CH₃ | CH₃ | Cl | 3-Cl |
| A.0988 | 2-Propynyl | CH₃ | CH₃ | Cl | 4-Cl |
| A.0989 | 2-Propynyl | CH₃ | CH₃ | Cl | 6-Cl |
| A.0990 | 2-Propynyl | CH₃ | CH₃ | Cl | 3-CH₃ |
| A.0991 | 2-Propynyl | CH₃ | CH₃ | Cl | 4-CH₃ |
| A.0992 | 2-Propynyl | CH₃ | CH₃ | Cl | 3-CF₃ |
| A.0993 | 2-Propynyl | CH₃ | CH₃ | Cl | 6-CH₃ |
| A.0994 | 2-Propynyl | CH₃ | CH₃ | Cl | 6-C₆H₅ |
| A.0995 | 2-Butynyl | CH₃ | CH₃ | Cl | H |
| A.0996 | 3-Butyn-2-yl | CH₃ | CH₃ | Cl | H |
| A.0997 | Cyanomethyl | CH₃ | CH₃ | Cl | H |
| A.0998 | Methoxycarbonylmethyl | CH₃ | CH₃ | Cl | H |
| A.0999 | tert-Butoxycarbonylmethyl | CH₃ | CH₃ | Cl | H |
| A.1000 | 1-(tert-Butoxycarbonyl)ethyl | CH₃ | CH₃ | Cl | H |
| A.1001 | Cyclopropylmethyl | CH₃ | CH₃ | Cl | H |
| A.1002 | 1-Methylcyclopentyl | CH₃ | CH₃ | Cl | H |
| A.1003 | Cyclohexyl | CH₃ | CH₃ | Cl | H |
| A.1004 | 1-Methoxypropan-2-yl | CH₃ | CH₃ | Cl | H |
| A.1005 | Benzyl | CH₃ | CH₃ | Cl | H |
| A.1006 | Benzyl | CH₃ | CH₃ | Cl | 3-Cl |
| A.1007 | Benzyl | CH₃ | CH₃ | Cl | 4-Cl |
| A.1008 | Benzyl | CH₃ | CH₃ | Cl | 6-Cl |
| A.1009 | Benzyl | CH₃ | CH₃ | Cl | 3-OCH₃ |
| A.1010 | Benzyl | CH₃ | CH₃ | Cl | 4-OCH₃ |
| A.1011 | Benzyl | CH₃ | CH₃ | Cl | 3-CF₃ |
| A.1012 | Benzyl | CH₃ | CH₃ | Cl | 6-CH₃ |
| A.1013 | Benzyl | CH₃ | CH₃ | Cl | 6-C₆H₅ |
| A.1014 | 3-Methylbenzyl | CH₃ | CH₃ | Cl | H |
| A.1015 | 2-Fluorobenzyl | CH₃ | CH₃ | Cl | H |
| A.1016 | 3-Fluorobenzyl | CH₃ | CH₃ | Cl | H |
| A.1017 | 4-Chlorobenzyl | CH₃ | CH₃ | Cl | H |
| A.1018 | 3,4-Dichlorobenzyl | CH₃ | CH₃ | Cl | H |
| A.1019 | 2,6-Difluorobenzyl | CH₃ | CH₃ | Cl | H |
| A.1020 | 3-Trifluoromethylbenzyl | CH₃ | CH₃ | Cl | H |
| A.1021 | 3-Cyanobenzyl | CH₃ | CH₃ | Cl | H |
| A.1022 | 4-Methoxybenzyl | CH₃ | CH₃ | Cl | H |
| A.1023 | 4-Methoxycarbonylbenzyl | CH₃ | CH₃ | Cl | H |
| A.1024 | 3-Phenylbenzyl | CH₃ | CH₃ | Cl | H |
| A.1025 | (5-Chloro-3-thienyl)-methyl | CH₃ | CH₃ | Cl | H |
| A.1026 | (2,5-Dichloro-3-thienyl)-methyl | CH₃ | CH₃ | Cl | H |
| A.1027 | (1,3-Dioxolan-2-yl)methyl | CH₃ | CH₃ | Cl | H |
| A.1028 | 1-Phenylethyl | CH₃ | CH₃ | Cl | H |
| A.1029 | 1-(4-Methylphenyl)- | CH₃ | CH₃ | Cl | H |

TABLE A-continued

| No. | R¹ | R² | R³ | R⁴ | R⁵n |
|---|---|---|---|---|---|
| A.1030 | 1-(4-Chlorophenyl)-ethyl | $CH_3$ | $CH_3$ | Cl | H |
| A.1031 | 1-(3-Trifluoromethyl-phenyl)-ethyl | $CH_3$ | $CH_3$ | Cl | H |
| A.1032 | 2-Phenyl-ethyl | $CH_3$ | $CH_3$ | Cl | H |
| A.1033 | 3-Phenyl-propan-1-yl | $CH_3$ | $CH_3$ | Cl | H |
| A.1034 | 4-(4-Chlorophenyl)-2-butenyl | $CH_3$ | $CH_3$ | Cl | H |
| A.1035 | Methyl | $CH_3$ | $CH_3$ | Br | H |
| A.1036 | Methyl | $CH_3$ | $CH_3$ | Br | 3-Cl |
| A.1037 | Methyl | $CH_3$ | $CH_3$ | Br | 4-Cl |
| A.1038 | Methyl | $CH_3$ | $CH_3$ | Br | 6-Cl |
| A.1039 | Methyl | $CH_3$ | $CH_3$ | Br | 3-$OCH_3$ |
| A.1040 | Methyl | $CH_3$ | $CH_3$ | Br | 4-$OCH_3$ |
| A.1041 | Methyl | $CH_3$ | $CH_3$ | Br | 3-$CF_3$ |
| A.1042 | Methyl | $CH_3$ | $CH_3$ | Br | 6-$CH_3$ |
| A.1043 | Methyl | $CH_3$ | $CH_3$ | Br | 6-$C_6H_5$ |
| A.1044 | Ethyl | $CH_3$ | $CH_3$ | Br | H |
| A.1045 | n-Propyl | $CH_3$ | $CH_3$ | Br | H |
| A.1046 | i-Propyl | $CH_3$ | $CH_3$ | Br | H |
| A.1047 | n-Butyl | $CH_3$ | $CH_3$ | Br | H |
| A.1048 | i-Butyl | $CH_3$ | $CH_3$ | Br | H |
| A.1049 | s-Butyl | $CH_3$ | $CH_3$ | Br | H |
| A.1050 | t-Butyl | $CH_3$ | $CH_3$ | Br | H |
| A.1051 | n-Pentyl | $CH_3$ | $CH_3$ | Br | H |
| A.1052 | n-Hexyl | $CH_3$ | $CH_3$ | Br | H |
| A.1053 | 2-Propenyl | $CH_3$ | $CH_3$ | Br | H |
| A.1054 | 2-Propenyl | $CH_3$ | $CH_3$ | Br | 3-Cl |
| A.1055 | 2-Propenyl | $CH_3$ | $CH_3$ | Br | 4-Cl |
| A.1056 | 2-Propenyl | $CH_3$ | $CH_3$ | Br | 6-Cl |
| A.1057 | 2-Propenyl | $CH_3$ | $CH_3$ | Br | 3-$OCH_3$ |
| A.1058 | 2-Propenyl | $CH_3$ | $CH_3$ | Br | 4-$OCH_3$ |
| A.1059 | 2-Propenyl | $CH_3$ | $CH_3$ | Br | 3-$CF_3$ |
| A.1060 | 2-Propenyl | $CH_3$ | $CH_3$ | Br | 6-$CH_3$ |
| A.1061 | 2-Propenyl | $CH_3$ | $CH_3$ | Br | 6-$C_6H_5$ |
| A.1062 | (E)-3-Chloro-2-propenyl | $CH_3$ | $CH_3$ | Br | H |
| A.1063 | 2-Chloro-2-propenyl | $CH_3$ | $CH_3$ | Br | H |
| A.1064 | (E)-2-Butenyl | $CH_3$ | $CH_3$ | Br | H |
| A.1065 | 2-Methyl-2-propenyl | $CH_3$ | $CH_3$ | Br | H |
| A.1066 | (Z)-3-Chloro-2-butenyl | $CH_3$ | $CH_3$ | Br | H |
| A.1067 | 3-Methyl-2-butenyl | $CH_3$ | $CH_3$ | Br | H |
| A.1068 | 2-Propynyl | $CH_3$ | $CH_3$ | Br | H |
| A.1069 | 2-Propynyl | $CH_3$ | $CH_3$ | Br | 3-Cl |
| A.1070 | 2-Propynyl | $CH_3$ | $CH_3$ | Br | 4-Cl |
| A.1071 | 2-Propynyl | $CH_3$ | $CH_3$ | Br | 6-Cl |
| A.1072 | 2-Propynyl | $CH_3$ | $CH_3$ | Br | 3-$OCH_3$ |
| A.1073 | 2-Propynyl | $CH_3$ | $CH_3$ | Br | 4-$OCH_3$ |
| A.1074 | 2-Propynyl | $CH_3$ | $CH_3$ | Br | 3-$CF_3$ |
| A.1075 | 2-Propynyl | $CH_3$ | $CH_3$ | Br | 6-$CH_3$ |
| A.1076 | 2-Propynyl | $CH_3$ | $CH_3$ | Br | 6-$C_6H_5$ |
| A.1077 | 2-Butynyl | $CH_3$ | $CH_3$ | Br | H |
| A.1078 | 3-Butyn-2-yl | $CH_3$ | $CH_3$ | Br | H |
| A.1079 | Cyanomethyl | $CH_3$ | $CH_3$ | Br | H |
| A.1080 | Methoxycarbonyl-methyl | $CH_3$ | $CH_3$ | Br | H |
| A.1081 | tert-Butoxycarbonyl-methyl | $CH_3$ | $CH_3$ | Br | H |
| A.1082 | 1-(tert-Butoxycarbonyl)-ethyl | $CH_3$ | $CH_3$ | Br | H |
| A.1083 | Cyclopropyl-methyl | $CH_3$ | $CH_3$ | Br | H |
| A.1084 | 1-Methyl-cyclopentyl | $CH_3$ | $CH_3$ | Br | H |
| A.1085 | Cyclohexyl | $CH_3$ | $CH_3$ | Br | H |
| A.1086 | 1-Methoxy-propan-2-yl | $CH_3$ | $CH_3$ | Br | H |
| A.1087 | Benzyl | $CH_3$ | $CH_3$ | Br | H |
| A.1088 | Benzyl | $CH_3$ | $CH_3$ | Br | 3-Cl |
| A.1089 | Benzyl | $CH_3$ | $CH_3$ | Br | 4-Cl |
| A.1090 | Benzyl | $CH_3$ | $CH_3$ | Br | 6-Cl |
| A.1091 | Benzyl | $CH_3$ | $CH_3$ | Br | 3-$OCH_3$ |
| A.1092 | Benzyl | $CH_3$ | $CH_3$ | Br | 4-$OCH_3$ |
| A.1093 | Benzyl | $CH_3$ | $CH_3$ | Br | 3-$CF_3$ |
| A.1094 | Benzyl | $CH_3$ | $CH_3$ | Br | 6-$CH_3$ |
| A.1095 | Benzyl | $CH_3$ | $CH_3$ | Br | 6-$C_6H_5$ |
| A.1096 | 3-Methyl-benzyl | $CH_3$ | $CH_3$ | Br | H |
| A.1097 | 2-Fluoro-benzyl | $CH_3$ | $CH_3$ | Br | H |
| A.1098 | 3-Fluoro-benzyl | $CH_3$ | $CH_3$ | Br | H |
| A.1099 | 4-Chloro-benzyl | $CH_3$ | $CH_3$ | Br | H |
| A.1100 | 3,4-Dichloro-benzyl | $CH_3$ | $CH_3$ | Br | H |
| A.1101 | 2,6-Difluoro-benzyl | $CH_3$ | $CH_3$ | Br | H |
| A.1102 | 3-Trifluoromethyl-benzyl | $CH_3$ | $CH_3$ | Br | H |
| A.1103 | 3-Cyano-benzyl | $CH_3$ | $CH_3$ | Br | H |
| A.1104 | 4-Methoxy-benzyl | $CH_3$ | $CH_3$ | Br | H |
| A.1105 | 4-Methoxy-carbonyl-benzyl | $CH_3$ | $CH_3$ | Br | H |
| A.1106 | 3-phenyl-benzyl | $CH_3$ | $CH_3$ | Br | H |
| A.1107 | (5-Chloro-3-thienyl)-methyl | $CH_3$ | $CH_3$ | Br | H |
| A.1108 | (2,5-Dichloro-3-thienyl)-methyl | $CH_3$ | $CH_3$ | Br | H |
| A.1109 | (1,3-Dioxolan-2-yl)methyl | $CH_3$ | $CH_3$ | Br | H |
| A.1110 | 1-Phenyl-ethyl | $CH_3$ | $CH_3$ | Br | H |
| A.1111 | 1-(4-Methyl-phenyl)-ethyl | $CH_3$ | $CH_3$ | Br | H |
| A.1112 | 1-(4-Chlorophenyl)-ethyl | $CH_3$ | $CH_3$ | Br | H |
| A.1113 | 1-(3-Trifluoromethyl-phenyl)-ethyl | $CH_3$ | $CH_3$ | Br | H |
| A.1114 | 2-Phenyl- | $CH_3$ | $CH_3$ | Br | H |

TABLE A-continued

| No. | R¹ | R² | R³ | R⁴ | R⁵n |
|---|---|---|---|---|---|
| A.1115 | 3-Phenyl-propan-1-yl | CH₃ | CH₃ | Br | H |
| A.1116 | 4-(4-Chloro-phenyl)-2-butenyl | CH₃ | CH₃ | Br | H |
| A.1117 | Methyl | CH₃ | CH₃ | CN | H |
| A.1118 | Methyl | CH₃ | CH₃ | CN | 3-Cl |
| A.1119 | Methyl | CH₃ | CH₃ | CN | 4-Cl |
| A.1120 | Methyl | CH₃ | CH₃ | CN | 6-Cl |
| A.1121 | Methyl | CH₃ | CH₃ | CN | 3-OCH₃ |
| A.1122 | Methyl | CH₃ | CH₃ | CN | 4-OCH₃ |
| A.1123 | Methyl | CH₃ | CH₃ | CN | 3-CF₃ |
| A.1124 | Methyl | CH₃ | CH₃ | CN | 6-CH₃ |
| A.1125 | Methyl | CH₃ | CH₃ | CN | 6-C₆H₅ |
| A.1126 | Ethyl | CH₃ | CH₃ | CN | H |
| A.1127 | n-Propyl | CH₃ | CH₃ | CN | H |
| A.1128 | i-Propyl | CH₃ | CH₃ | CN | H |
| A.1129 | n-Butyl | CH₃ | CH₃ | CN | H |
| A.1130 | i-Butyl | CH₃ | CH₃ | CN | H |
| A.1131 | s-Butyl | CH₃ | CH₃ | CN | H |
| A.1132 | t-Butyl | CH₃ | CH₃ | CN | H |
| A.1133 | n-Pentyl | CH₃ | CH₃ | CN | H |
| A.1134 | n-Hexyl | CH₃ | CH₃ | CN | H |
| A.1135 | 2-Propenyl | CH₃ | CH₃ | CN | H |
| A.1136 | 2-Propenyl | CH₃ | CH₃ | CN | 3-Cl |
| A.1137 | 2-Propenyl | CH₃ | CH₃ | CN | 4-Cl |
| A.1138 | 2-Propenyl | CH₃ | CH₃ | CN | 6-Cl |
| A.1139 | 2-Propenyl | CH₃ | CH₃ | CN | 3-OCH₃ |
| A.1140 | 2-Propenyl | CH₃ | CH₃ | CN | 4-OCH₃ |
| A.1141 | 2-Propenyl | CH₃ | CH₃ | CN | 3-CF₃ |
| A.1142 | 2-Propenyl | CH₃ | CH₃ | CN | 6-CH₃ |
| A.1143 | 2-Propenyl | CH₃ | CH₃ | CN | 6-C₆H₅ |
| A.1144 | (E)-3-Chloro-2-propenyl | CH₃ | CH₃ | CN | H |
| A.1145 | 2-Chloro-2-propenyl | CH₃ | CH₃ | CN | H |
| A.1146 | (E)-2-Butenyl | CH₃ | CH₃ | CN | H |
| A.1147 | 2-Methyl-2-propenyl | CH₃ | CH₃ | CN | H |
| A.1148 | (Z)-3-Chloro-2-butenyl | CH₃ | CH₃ | CN | H |
| A.1149 | 3-Methyl-2-butenyl | CH₃ | CH₃ | CN | H |
| A.1150 | 2-Propynyl | CH₃ | CH₃ | CN | H |
| A.1151 | 2-Propynyl | CH₃ | CH₃ | CN | 3-Cl |
| A.1152 | 2-Propynyl | CH₃ | CH₃ | CN | 4-Cl |
| A.1153 | 2-Propynyl | CH₃ | CH₃ | CN | 6-Cl |
| A.1154 | 2-Propynyl | CH₃ | CH₃ | CN | 3-OCH₃ |
| A.1155 | 2-Propynyl | CH₃ | CH₃ | CN | 4-OCH₃ |
| A.1156 | 2-Propynyl | CH₃ | CH₃ | CN | 6-CF₃ |
| A.1157 | 2-Propynyl | CH₃ | CH₃ | CN | 6-CH₃ |
| A.1158 | 2-Propynyl | CH₃ | CH₃ | CN | 6-C₆H₅ |
| A.1159 | 2-Butynyl | CH₃ | CH₃ | CN | H |
| A.1160 | 3-Butyn-2-yl | CH₃ | CH₃ | CN | H |
| A.1161 | Cyano-methyl | CH₃ | CH₃ | CN | H |
| A.1162 | Methoxy-carbonyl-methyl | CH₃ | CH₃ | CN | H |
| A.1163 | tert-Butoxy-carbonyl-methyl | CH₃ | CH₃ | CN | H |
| A.1164 | 1-(tert-Butoxy-carbonyl)-ethyl | CH₃ | CH₃ | CN | H |
| A.1165 | Cyclo-propyl-methyl | CH₃ | CH₃ | CN | H |
| A.1166 | 1-Methyl-cyclopentyl | CH₃ | CH₃ | CN | H |
| A.1167 | Cyclohexyl | CH₃ | CH₃ | CN | H |
| A.1168 | 1-Methoxy-propan-2-yl | CH₃ | CH₃ | CN | H |
| A.1169 | Benzyl | CH₃ | CH₃ | CN | H |
| A.1170 | Benzyl | CH₃ | CH₃ | CN | 3-Cl |
| A.1171 | Benzyl | CH₃ | CH₃ | CN | 4-Cl |
| A.1172 | Benzyl | CH₃ | CH₃ | CN | 6-Cl |
| A.1173 | Benzyl | CH₃ | CH₃ | CN | 3-OCH₃ |
| A.1174 | Benzyl | CH₃ | CH₃ | CN | 4-OCH₃ |
| A.1175 | Benzyl | CH₃ | CH₃ | CN | 3-CF₃ |
| A.1176 | Benzyl | CH₃ | CH₃ | CN | 6-CH₃ |
| A.1177 | Benzyl | CH₃ | CH₃ | CN | 6-C₆H₅ |
| A.1178 | 3-Methyl-benzyl | CH₃ | CH₃ | CN | H |
| A.1179 | 2-Fluoro-benzyl | CH₃ | CH₃ | CN | H |
| A.1180 | 3-Fluoro-benzyl | CH₃ | CH₃ | CN | H |
| A.1181 | 4-Chloro-benzyl | CH₃ | CH₃ | CN | H |
| A.1182 | 3,4-Di-chloro-benzyl | CH₃ | CH₃ | CN | H |
| A.1183 | 2,6-Di-fluoro-benzyl | CH₃ | CH₃ | CN | H |
| A.1184 | 3-Trifluoro-methyl-benzyl | CH₃ | CH₃ | CN | H |
| A.1185 | 3-Cyano-benzyl | CH₃ | CH₃ | CN | H |
| A.1186 | 4-Methyl-benzyl | CH₃ | CH₃ | CN | H |
| A.1187 | 4-Methoxy-carbonyl-benzyl | CH₃ | CH₃ | CN | H |
| A.1188 | 3-Phenyl-benzyl | CH₃ | CH₃ | CN | H |
| A.1189 | (5-Chloro-3-thienyl)-methyl | CH₃ | CH₃ | CN | H |
| A.1190 | (2,5-Di-chloro-3-thienyl)-methyl | CH₃ | CH₃ | CN | H |
| A.1191 | (1,3-Di-oxolan-2-yl)methyl | CH₃ | CH₃ | CN | H |
| A.1192 | 1-Phenyl-ethyl | CH₃ | CH₃ | CN | H |
| A.1193 | 1-(4-Methyl-phenyl)-ethyl | CH₃ | CH₃ | CN | H |
| A.1194 | 1-(4-Chloro-phenyl)-ethyl | CH₃ | CH₃ | CN | H |
| A.1195 | 1-(3-Tri-fluoro-methyl-phenyl)-ethyl | CH₃ | CH₃ | CN | H |
| A.1196 | 2-Phenyl-ethyl | CH₃ | CH₃ | CN | H |
| A.1197 | 3-Phenyl-propan-1-yl | CH₃ | CH₃ | CN | H |
| A.1198 | 4-(4-Chloro-phenyl)-2-butenyl | CH₃ | CH₃ | CN | H |
| A.1199 | Methyl | CH₃ | CH₃ | OCH₂C≡CH | H |
| A.1200 | Ethyl | CH₃ | CH₃ | OCH₂C≡CH | H |
| A.1201 | 2-Propenyl | CH₃ | CH₃ | OCH₂C≡CH | H |
| A.1202 | 2-Propynyl | CH₃ | CH₃ | OCH₂C≡CH | H |
| A.1203 | 1-(tert- | CH₃ | CH₃ | OCH₂C≡CH | H |

TABLE A-continued

| No. | R¹ | R² | R³ | R⁴ | R⁵n |
|---|---|---|---|---|---|
| A.1204 | Butoxy-carbonyl)-ethyl 3-Methyl-benzyl | CH₃ | CH₃ | OCH₂C≡CH | H |
| A.1205 | 1-Phenyl-ethyl | CH₃ | CH₃ | OCH₂C≡CH | H |
| A.1206 | Methyl | CH₃ | CH₃ | OCH₂CH₂C₆H₅ | H |
| A.1207 | Ethyl | CH₃ | CH₃ | OCH₂CH₂C₆H₅ | H |
| A.1208 | 2-Propenyl | CH₃ | CH₃ | OCH₂CH₂C₆H₅ | H |
| A.1209 | 2-Propynyl | CH₃ | CH₃ | OCH₂CH₂C₆H₅ | H |
| A.1210 | 1-(tert-Butoxy-carbonyl)-ethyl | CH₃ | CH₃ | OCH₂CH₂C₆H₅ | H |
| A.1211 | 3-Methyl-benzyl | CH₃ | CH₃ | OCH₂CH₂C₆H₅ | H |
| A.1212 | 1-Phenyl-ethyl | CH₃ | CH₃ | OCH₂CH₂C₆H₅ | H |
| A.1213 | Methyl | CH₃ | CH₃ | SCH₂CH₃ | H |
| A.1214 | Ethyl | CH₃ | CH₃ | SCH₂CH₃ | H |
| A.1215 | 2-Propenyl | CH₃ | CH₃ | SCH₂CH₃ | H |
| A.1216 | 2-Propynyl | CH₃ | CH₃ | SCH₂CH₃ | H |
| A.1217 | 1-(tert-Butoxy-carbonyl)-ethyl | CH₃ | CH₃ | SCH₂CH₃ | H |
| A.1218 | 3-Methyl-benzyl | CH₃ | CH₃ | SCH₂CH₃ | H |
| A.1219 | 1-Phenyl-ethyl | CH₃ | CH₃ | SCH₂CH₃ | H |
| A.1220 | Methyl | CH₃ | CH₃ | NH—CH₃ | H |
| A.1221 | Ethyl | CH₃ | CH₃ | NH—CH₃ | H |
| A.1222 | 2-Propenyl | CH₃ | CH₃ | NH—CH₃ | H |
| A.1223 | 2-Propynyl | CH₃ | CH₃ | NH—CH₃ | H |
| A.1224 | 1-(tert-Butoxy-carbonyl)-ethyl | CH₃ | CH₃ | NH—CH₃ | H |
| A.1225 | 3-Methyl-benzyl | CH₃ | CH₃ | NH—CH₃ | H |
| A.1226 | 1-Phenyl-ethyl | CH₃ | CH₃ | NH—CH₃ | H |
| A.1227 | Methyl | CH₃ | CH₃ | N(CH₃)₂ | H |
| A.1228 | Ethyl | CH₃ | CH₃ | N(CH₃)₂ | H |
| A.1229 | 2-Propenyl | CH₃ | CH₃ | N(CH₃)₂ | H |
| A.1230 | 2-Propynyl | CH₃ | CH₃ | N(CH₃)₂ | H |
| A.1231 | 1-(tert-Butoxy-carbonyl)-ethyl | CH₃ | CH₃ | N(CH₃)₂ | H |
| A.1232 | 3-Methyl-benzyl | CH₃ | CH₃ | N(CH₃)₂ | H |
| A.1233 | 1-Phenyl-ethyl | CH₃ | CH₃ | N(CH₃)₂ | H |
| A.1234 | Methyl | CH₃ | CH₃ | OC₆H₅ | H |
| A.1235 | Ethyl | CH₃ | CH₃ | OC₆H₅ | H |
| A.1236 | 2-Propenyl | CH₃ | CH₃ | OC₆H₅ | H |
| A.1237 | 2-Propynyl | CH₃ | CH₃ | OC₆H₅ | H |
| A.1238 | 1-(tert-Butoxy-carbonyl)-ethyl | CH₃ | CH₃ | OC₆H₅ | H |
| A.1239 | 3-Methyl-butyl | CH₃ | CH₃ | OC₆H₅ | H |
| A.1240 | 1-Phenethyl | CH₃ | CH₃ | OC₆H₅ | H |
| A.1241 | Methyl | CH₃ | CH₃ | SC₆H₅ | H |
| A.1242 | Ethyl | CH₃ | CH₃ | SC₆H₅ | H |
| A.1243 | 2-Propenyl | CH₃ | CH₃ | SC₆H₅ | H |
| A.1244 | 2-Propynyl | CH₃ | CH₃ | SC₆H₅ | H |
| A.1245 | 1-(tert-Butoxy-carbonyl)-ethyl | CH₃ | CH₃ | SC₆H₅ | H |
| A.1246 | 3-Methyl-benzyl | CH₃ | CH₃ | SC₆H₅ | H |
| A.1247 | 1-Phenyl-ethyl | CH₃ | CH₃ | SC₆H₅ | H |
| A.1248 | Methyl | 2-Cl | H | OCH₃ | H |
| A.1249 | Methyl | 2-Cl | H | OCH₃ | 3-Cl |
| A.1250 | Methyl | 2-Cl | H | OCH₃ | 4-Cl |
| A.1251 | Methyl | 2-Cl | H | OCH₃ | 6-Cl |
| A.1252 | Methyl | 2-Cl | H | OCH₃ | 3-OCH₃ |
| A.1253 | Methyl | 2-Cl | H | OCH₃ | 4-OCH₃ |
| A.1254 | Methyl | 2-Cl | H | OCH₃ | 3-CF₃ |
| A.1255 | Methyl | 2-Cl | H | OCH₃ | 6-CH₃ |
| A.1256 | Methyl | 2-Cl | H | OCH₃ | 6-C₆H₅ |
| A.1257 | Ethyl | 2-Cl | H | OCH₃ | H |
| A.1258 | n-Propyl | 2-Cl | H | OCH₃ | H |
| A.1259 | i-Propyl | 2-Cl | H | OCH₃ | H |
| A.1260 | n-Butyl | 2-Cl | H | OCH₃ | H |
| A.1261 | i-Butyl | 2-Cl | H | OCH₃ | H |
| A.1262 | s-Butyl | 2-Cl | H | OCH₃ | H |
| A.1263 | t-Butyl | 2-Cl | H | OCH₃ | H |
| A.1264 | n-Pentyl | 2-Cl | H | OCH₃ | H |
| A.1265 | n-Hexyl | 2-Cl | H | OCH₃ | H |
| A.1266 | 2-Propenyl | 2-Cl | H | OCH₃ | H |
| A.1267 | 2-Propenyl | 2-Cl | H | OCH₃ | 3-Cl |
| A.1268 | 2-Propenyl | 2-Cl | H | OCH₃ | 4-Cl |
| A.1269 | 2-Propenyl | 2-Cl | H | OCH₃ | 6-Cl |
| A.1270 | 2-Propenyl | 2-Cl | H | OCH₃ | 3-OCH₃ |
| A.1271 | 2-Propenyl | 2-Cl | H | OCH₃ | 4-OCH₃ |
| A.1272 | 2-Propenyl | 2-Cl | H | OCH₃ | 3-CF₃ |
| A.1273 | 2-Propenyl | 2-Cl | H | OCH₃ | 6-CH₃ |
| A.1274 | 2-Propenyl | 2-Cl | H | OCH₃ | 6-C₆H₅ |
| A.1275 | (E)-3-Chloro-2-propenyl | 2-Cl | H | OCH₃ | H |
| A.1276 | 2-Chloro-2-propenyl | 2-Cl | H | OCH₃ | H |
| A.1277 | (E)-2-Butenyl | 2-Cl | H | OCH₃ | H |
| A.1278 | 2-Methyl-2-propenyl | 2-Cl | H | OCH₃ | H |
| A.1279 | (Z)-3-Chloro-2-butenyl | 2-Cl | H | OCH₃ | H |
| A.1280 | 3-Methyl-2-butenyl | 2-Cl | H | OCH₃ | H |
| A.1281 | 2-Propynyl | 2-Cl | H | OCH₃ | H |
| A.1282 | 2-Propynyl | 2-Cl | H | OCH₃ | 3-Cl |
| A.1283 | 2-Propynyl | 2-Cl | H | OCH₃ | 4-Cl |
| A.1284 | 2-Propynyl | 2-Cl | H | OCH₃ | 6-Cl |
| A.1285 | 2-Propynyl | 2-Cl | H | OCH₃ | 3-OCH₃ |
| A.1286 | 2-Propynyl | 2-Cl | H | OCH₃ | 4-OCH₃ |
| A.1287 | 2-Propynyl | 2-Cl | H | OCH₃ | 3-CF₃ |
| A.1288 | 2-Propynyl | 2-Cl | H | OCH₃ | 6-CH₃ |
| A.1289 | 2-Propynyl | 2-Cl | H | OCH₃ | 6-C₆H₅ |
| A.1290 | 2-Butynyl | 2-Cl | H | OCH₃ | H |
| A.1291 | 3-Butyn-2-yl | 2-Cl | H | OCH₃ | H |
| A.1292 | Cyano-methyl | 2-Cl | H | OCH₃ | H |
| A.1293 | Methoxy-carbonyl-methyl | 2-Cl | H | OCH₃ | H |
| A.1294 | tert-Butoxy-carbonyl-methyl | 2-Cl | H | OCH₃ | H |
| A.1295 | 1-(tert-Butoxy-carbonyl)-ethyl | 2-Cl | H | OCH₃ | H |
| A.1296 | Cyclo-propyl-methyl | 2-Cl | H | OCH₃ | H |
| A.1297 | 1-Methyl-cyclopentyl | 2-Cl | H | OCH₃ | H |
| A.1298 | Cyclohexyl | 2-Cl | H | OCH₃ | H |
| A.1299 | 1-Methoxy-propan-2-yl | 2-Cl | H | OCH₃ | H |
| A.1300 | Benzyl | 2-Cl | H | OCH₃ | H |
| A.1301 | Benzyl | 2-Cl | H | OCH₃ | 3-Cl |

TABLE A-continued

| No. | R¹ | R² | R³ | R⁴ | R⁵n |
|---|---|---|---|---|---|
| A.1302 | Benzyl | 2-Cl | H | OCH₃ | 4-Cl |
| A.1303 | Benzyl | 2-Cl | H | OCH₃ | 6-Cl |
| A.1304 | Benzyl | 2-Cl | H | OCH₃ | 3-OCH₃ |
| A.1305 | Benzyl | 2-Cl | H | OCH₃ | 4-OCH₃ |
| A.1306 | Benzyl | 2-Cl | H | OCH₃ | 3-CF₃ |
| A.1307 | Benzyl | 2-Cl | H | OCH₃ | 6-CH₃ |
| A.1308 | Benzyl | 2-Cl | H | OCH₃ | 6-C₆H₅ |
| A.1309 | 3-Methyl-benzyl | 2-Cl | H | OCH₃ | H |
| A.1310 | 2-Fluoro-benzyl | 2-Cl | H | OCH₃ | H |
| A.1311 | 3-Fluoro-benzyl | 2-Cl | H | OCH₃ | H |
| A.1312 | 4-Chloro-benzyl | 2-Cl | H | OCH₃ | H |
| A.1313 | 3,4-Di-chloro-benzyl | 2-Cl | H | OCH₃ | H |
| A.1314 | 2,6-Di-fluoro-benzyl | 2-Cl | H | OCH₃ | H |
| A.1315 | 3-Trifluoro-methyl-benzyl | 2-Cl | H | OCH₃ | H |
| A.1316 | 3-Cyano-benzyl | 2-Cl | H | OCH₃ | H |
| A.1317 | 4-Methyl-benzyl | 2-Cl | H | OCH₃ | H |
| A.1318 | 4-Methoxy-carbonyl-benzyl | 2-Cl | H | OCH₃ | H |
| A.1319 | 3-Phenyl-benzyl | 2-Cl | H | OCH₃ | H |
| A.1320 | (5-Chloro-3-thienyl)-methyl | 2-Cl | H | OCH₃ | H |
| A.1321 | (2,5-Di-chloro-3-thienyl)-methyl | 2-Cl | H | OCH₃ | H |
| A.1322 | (1,3-Di-oxolan-2-yl)methyl | 2-Cl | H | OCH₃ | H |
| A.1323 | 1-Phenyl-ethyl | 2-Cl | H | OCH₃ | H |
| A.1324 | 1-(4-Methyl-phenyl)-ethyl | 2-Cl | H | OCH₃ | H |
| A.1325 | 1-(4-Chloro-phenyl)-ethyl | 2-Cl | H | OCH₃ | H |
| A.1326 | 1-(3-Tri-fluoro-methyl-phenyl)-ethyl | 2-Cl | H | OCH₃ | H |
| A.1327 | 2-Phenyl-ethyl | 2-Cl | H | OCH₃ | H |
| A.1328 | 3-Phenyl-propan-1-yl | 2-Cl | H | OCH₃ | H |
| A.1329 | 4-(4-Chloro-phenyl)-2-butenyl | 2-Cl | H | OCH₃ | H |
| A.1330 | Methyl | 2-Cl | H | OC₂H₅ | H |
| A.1331 | Methyl | 2-Cl | H | OC₂H₅ | 3-Cl |
| A.1332 | Methyl | 2-Cl | H | OC₂H₅ | 4-Cl |
| A.1333 | Methyl | 2-Cl | H | OC₂H₅ | 6-Cl |
| A.1334 | Methyl | 2-Cl | H | OC₂H₅ | 3-OCH₃ |
| A.1335 | Methyl | 2-Cl | H | OC₂H₅ | 4-OCH₃ |
| A.1336 | Methyl | 2-Cl | H | OC₂H₅ | 3-CF₃ |
| A.1337 | Methyl | 2-Cl | H | OC₂H₅ | 6-CH₃ |
| A.1338 | Methyl | 2-Cl | H | OC₂H₅ | 6-C₆H₅ |
| A.1339 | Ethyl | 2-Cl | H | OC₂H₅ | H |
| A.1340 | n-Propyl | 2-Cl | H | OC₂H₅ | H |
| A.1341 | i-Propyl | 2-Cl | H | OC₂H₅ | H |
| A.1342 | n-Butyl | 2-Cl | H | OC₂H₅ | H |
| A.1343 | i-Butyl | 2-Cl | H | OC₂H₅ | H |
| A.1344 | s-Butyl | 2-Cl | H | OC₂H₅ | H |
| A.1345 | t-Butyl | 2-Cl | H | OC₂H₅ | H |
| A.1346 | n-Pentyl | 2-Cl | H | OC₂H₅ | H |
| A.1347 | n-Hexyl | 2-Cl | H | OC₂H₅ | H |
| A.1348 | 2-Propenyl | 2-Cl | H | OC₂H₅ | H |
| A.1349 | 2-Propenyl | 2-Cl | H | OC₂H₅ | 3-Cl |
| A.1350 | 2-Propenyl | 2-Cl | H | OC₂H₅ | 6-Cl |
| A.1351 | 2-Propenyl | 2-Cl | H | OC₂H₅ | 6-Cl |
| A.1352 | 2-Propenyl | 2-Cl | H | OC₂H₅ | 3-OCH₃ |
| A.1353 | 2-Propenyl | 2-Cl | H | OC₂H₅ | 4-OCH₃ |
| A.1354 | 2-Propenyl | 2-Cl | H | OC₂H₅ | 3-CF₃ |
| A.1355 | 2-Propenyl | 2-Cl | H | OC₂H₅ | 6-CH₃ |
| A.1356 | 2-Propenyl | 2-Cl | H | OC₂H₅ | 6-C₆H₅ |
| A.1357 | (E)-3-Chloro-2-propenyl | 2-Cl | H | OC₂H₅ | H |
| A.1358 | 2-Chloro-2-propenyl | 2-Cl | H | OC₂H₅ | H |
| A.1359 | (E)-2-Butenyl | 2-Cl | H | OC₂H₅ | H |
| A.1360 | 2-Methyl-2-propenyl | 2-Cl | H | OC₂H₅ | H |
| A.1361 | (Z)-3-Chloro-2-butenyl | 2-Cl | H | OC₂H₅ | H |
| A.1362 | 3-Methyl-2-butenyl | 2-Cl | H | OC₂H₅ | H |
| A.1363 | 2-Propynyl | 2-Cl | H | OC₂H₅ | H |
| A.1364 | 2-Propynyl | 2-Cl | H | OC₂H₅ | 3-Cl |
| A.1365 | 2-Propynyl | 2-Cl | H | OC₂H₅ | 4-Cl |
| A.1366 | 2-Propynyl | 2-Cl | H | OC₂H₅ | 6-Cl |
| A.1367 | 2-Propynyl | 2-Cl | H | OC₂H₅ | 3-OCH₃ |
| A.1368 | 2-Propynyl | 2-Cl | H | OC₂H₅ | 4-OCH₃ |
| A.1369 | 2-Propynyl | 2-Cl | H | OC₂H₅ | 3-CF₃ |
| A.1370 | 2-Propynyl | 2-Cl | H | OC₂H₅ | 6-CH₃ |
| A.1371 | 2-Propynyl | 2-Cl | H | OC₂H₅ | 6-C₆H₅ |
| A.1372 | 2-Butynyl | 2-Cl | H | OC₂H₅ | H |
| A.1373 | 3-Butyn-2-yl | 2-Cl | H | OC₂H₅ | H |
| A.1374 | Cyano-methyl | 2-Cl | H | OC₂H₅ | H |
| A.1375 | Methoxy-carbonyl-methyl | 2-Cl | H | OC₂H₅ | H |
| A.1376 | tert-Butoxy-carbonyl-methyl | 2-Cl | H | OC₂H₅ | H |
| A.1377 | 1-(tert-Butoxy-carbonyl)-ethyl | 2-Cl | H | OC₂H₅ | H |
| A.1378 | Cyclo-propyl-methyl | 2-Cl | H | OC₂H₅ | H |
| A.1379 | 1-Methyl-cyclopentyl | 2-Cl | H | OC₂H₅ | H |
| A.1380 | Cyclohexyl | 2-Cl | H | OC₂H₅ | H |
| A.1381 | 1-Methoxy-propan-2-yl | 2-Cl | H | OC₂H₅ | H |
| A.1382 | Benzyl | 2-Cl | H | OC₂H₅ | H |
| A.1383 | Benzyl | 2-Cl | H | OC₂H₅ | 3-Cl |
| A.1384 | Benzyl | 2-Cl | H | OC₂H₅ | 4-Cl |
| A.1385 | Benzyl | 2-Cl | H | OC₂H₅ | 6-Cl |
| A.1386 | Benzyl | 2-Cl | H | OC₂H₅ | 3-OCH₃ |
| A.1387 | Benzyl | 2-Cl | H | OC₂H₅ | 4-OCH₃ |
| A.1388 | Benzyl | 2-Cl | H | OC₂H₅ | 3-CF₃ |
| A.1389 | Benzyl | 2-Cl | H | OC₂H₅ | 6-CH₃ |
| A.1390 | Benzyl | 2-Cl | H | OC₂H₅ | 6-C₆H₅ |
| A.1391 | 3-Methyl-benzyl | 2-Cl | H | OC₂H₅ | H |
| A.1392 | 2-Fluoro-benzyl | 2-Cl | H | OC₂H₅ | H |
| A.1393 | 3-Fluoro- | 2-Cl | H | OC₂H₅ | H |

TABLE A-continued

| No. | R¹ | R² | R³ | R⁴ | R⁵n |
|---|---|---|---|---|---|
| A.1394 | 4-Chloro-benzyl | 2-Cl | H | OC₂H₅ | H |
| A.1395 | 3,4-Dichloro-benzyl | 2-Cl | H | OC₂H₅ | H |
| A.1396 | 2,6-Difluoro-benzyl | 2-Cl | H | OC₂H₅ | H |
| A.1397 | 3-Trifluoromethyl-benzyl | 2-Cl | H | OC₂H₅ | H |
| A.1398 | 3-Cyano-benzyl | 2-Cl | H | OC₂H₅ | H |
| A.1399 | 4-Methyl-benzyl | 2-Cl | H | OC₂H₅ | H |
| A.1400 | 4-Methoxycarbonyl-benzyl | 2-Cl | H | OC₂H₅ | H |
| A.1401 | 3-Phenyl-benzyl | 2-Cl | H | OC₂H₅ | H |
| A.1402 | (5-Chloro-3-thienyl)-methyl | 2-Cl | H | OC₂H₅ | H |
| A.1403 | (2,5-Dichloro-3-thienyl)-methyl | 2-Cl | H | OC₂H₅ | H |
| A.1404 | (1,3-Dioxolan-2-yl)methyl | 2-Cl | H | OC₂H₅ | H |
| A.1405 | 1-Phenyl-ethyl | 2-Cl | H | OC₂H₅ | H |
| A.1406 | 1-(4-Methylphenyl)-ethyl | 2-Cl | H | OC₂H₅ | H |
| A.1407 | 1-(4-Chlorophenyl)-ethyl | 2-Cl | H | OC₂H₅ | H |
| A.1408 | 1-(3-Trifluoromethylphenyl)-ethyl | 2-Cl | H | OC₂H₅ | H |
| A.1409 | 2-Phenyl-ethyl | 2-Cl | H | OC₂H₅ | H |
| A.1410 | 3-Phenyl-propan-1-yl | 2-Cl | H | OC₂H₅ | H |
| A.1411 | 4-(4-Chlorophenyl)-2-butenyl | 2-Cl | H | OC₂H₅ | H |
| A.1412 | Methyl | 2-Cl | H | CH₂CH=CH₂ | H |
| A.1413 | Methyl | 2-Cl | H | OCH₂CH=CH₂ | 3-Cl |
| A.1414 | Methyl | 2-Cl | H | OCH₂CH=CH₂ | 4-Cl |
| A.1415 | Methyl | 2-Cl | H | OCH₂CH=CH₂ | 6-Cl |
| A.1416 | Methyl | 2-Cl | H | OCH₂CH=CH₂ | 3-OCH₃ |
| A.1417 | Methyl | 2-Cl | H | OCH₂CH=CH₂ | 4-OCH₃ |
| A.1418 | Methyl | 2-Cl | H | OCH₂CH=CH₂ | 3-CF₃ |
| A.1419 | Methyl | 2-Cl | H | OCH₂CH=CH₂ | 6-CH₃ |
| A.1420 | Methyl | 2-Cl | H | OCH₂CH=CH₂ | 6-C₆H₅ |
| A.1421 | Ethyl | 2-Cl | H | OCH₂CH=CH₂ | H |
| A.1422 | n-Propyl | 2-Cl | H | OCH₂CH=CH₂ | H |
| A.1423 | i-Propyl | 2-Cl | H | OCH₂CH=CH₂ | H |
| A.1424 | n-Butyl | 2-Cl | H | OCH₂CH=CH₂ | H |
| A.1425 | i-Butyl | 2-Cl | H | OCH₂CH=CH₂ | H |
| A.1426 | s-Butyl | 2-Cl | H | OCH₂CH=CH₂ | H |
| A.1427 | t-Butyl | 2-Cl | H | OCH₂CH=CH₂ | H |
| A.1428 | n-Pentyl | 2-Cl | H | OCH₂CH=CH₂ | H |
| A.1429 | n-Hexyl | 2-Cl | H | OCH₂CH=CH₂ | H |
| A.1430 | 2-Propenyl | 2-Cl | H | OCH₂CH=CH₂ | H |
| A.1431 | 2-Propenyl | 2-Cl | H | OCH₂CH=CH₂ | 3-Cl |
| A.1432 | 2-Propenyl | 2-Cl | H | OCH₂CH=CH₂ | 4-Cl |
| A.1433 | 2-Propenyl | 2-Cl | H | OCH₂CH=CH₂ | 6-Cl |
| A.1434 | 2-Propenyl | 2-Cl | H | OCH₂CH=CH₂ | 3-OCH₃ |
| A.1435 | 2-Propenyl | 2-Cl | H | OCH₂CH=CH₂ | 4-OCH₃ |
| A.1436 | 2-Propenyl | 2-Cl | H | OCH₂CH=CH₂ | 3-CF₃ |
| A.1437 | 2-Propenyl | 2-Cl | H | OCH₂CH=CH₂ | 6-CH₃ |
| A.1438 | 2-Propenyl | 2-Cl | H | OCH₂CH=CH₂ | 6-C₆H₅ |
| A.1439 | (E)-3-Chloro-2-propenyl | 2-Cl | H | OCH₂CH=CH₂ | H |
| A.1440 | 2-Chloro-2-propenyl | 2-Cl | H | OCH₂CH=CH₂ | H |
| A.1441 | (E)-2-Butenyl | 2-Cl | H | OCH₂CH=CH₂ | H |
| A.1442 | 2-Methyl-2-propenyl | 2-Cl | H | OCH₂CH=CH₂ | H |
| A.1443 | (Z)-3-Chloro-2-butenyl | 2-Cl | H | OCH₂CH=CH₂ | H |
| A.1444 | 3-Methyl-2-butenyl | 2-Cl | H | OCH₂CH=CH₂ | H |
| A.1445 | 2-Propynyl | 2-Cl | H | OCH₂CH=CH₂ | H |
| A.1446 | 2-Propynyl | 2-Cl | H | OCH₂CH=CH₂ | H |
| A.1447 | 2-Propynyl | 2-Cl | H | OCH₂CH=CH₂ | 4-Cl |
| A.1448 | 2-Propynyl | 2-Cl | H | OCH₂CH=CH₂ | 6-Cl |
| A.1449 | 2-Propynyl | 2-Cl | H | OCH₂CH=CH₂ | 3-OCH₃ |
| A.1450 | 2-Propynyl | 2-Cl | H | OCH₂CH=CH₂ | 4-OCH₃ |
| A.1451 | 2-Propynyl | 2-Cl | H | OCH₂CH=CH₂ | 3-CF₃ |
| A.1452 | 2-Propynyl | 2-Cl | H | OCH₂CH=CH₂ | 6-CH₃ |
| A.1453 | 2-Propynyl | 2-Cl | H | OCH₂CH=CH₂ | 6-C₆H₅ |
| A.1454 | 2-Butynyl | 2-Cl | H | OCH₂CH=CH₂ | H |
| A.1455 | 3-Butyn-2-yl | 2-Cl | H | OCH₂CH=CH₂ | H |
| A.1456 | Cyanomethyl | 2-Cl | H | OCH₂CH=CH₂ | H |
| A.1457 | Methoxycarbonyl-methyl | 2-Cl | H | OCH₂CH=CH₂ | H |
| A.1458 | tert-Butoxycarbonyl-methyl | 2-Cl | H | OCH₂CH=CH₂ | H |
| A.1459 | 1-(tert-Butoxycarbonyl)-ethyl | 2-Cl | H | OCH₂CH=CH₂ | H |
| A.1460 | Cyclopropyl-methyl | 2-Cl | H | OCH₂CH=CH₂ | H |
| A.1461 | 1-Methyl-cyclopentyl | 2-Cl | H | OCH₂CH=CH₂ | H |
| A.1462 | Cyclohexyl | 2-Cl | H | OCH₂CH=CH₂ | H |
| A.1463 | 1-Methoxy-propan-2-yl | 2-Cl | H | OCH₂CH=CH₂ | H |
| A.1464 | Benzyl | 2-Cl | H | OCH₂CH=CH₂ | H |
| A.1465 | Benzyl | 2-Cl | H | OCH₂CH=CH₂ | 3-Cl |
| A.1466 | Benzyl | 2-Cl | H | OCH₂CH=CH₂ | 4-Cl |
| A.1467 | Benzyl | 2-Cl | H | OCH₂CH=CH₂ | 6-Cl |
| A.1468 | Benzyl | 2-Cl | H | OCH₂CH=CH₂ | 3-OCH₃ |
| A.1469 | Benzyl | 2-Cl | H | OCH₂CH=CH₂ | 4-OCH₃ |
| A.1470 | Benzyl | 2-Cl | H | OCH₂CH=CH₂ | 3-CF₃ |
| A.1471 | Benzyl | 2-Cl | H | OCH₂CH=CH₂ | 6-CH₃ |
| A.1472 | Benzyl | 2-Cl | H | OCH₂CH=CH₂ | 6-C₆H₅ |
| A.1473 | 3-Methyl-benzyl | 2-Cl | H | OCH₂CH=CH₂ | H |
| A.1474 | 2-Fluoro-benzyl | 2-Cl | H | OCH₂CH=CH₂ | H |
| A.1475 | 3-Fluoro-benzyl | 2-Cl | H | OCH₂CH=CH₂ | H |
| A.1476 | 4-Chloro-benzyl | 2-Cl | H | OCH₂CH=CH₂ | H |
| A.1477 | 3,4-Dichloro-benzyl | 2-Cl | H | OCH₂CH=CH₂ | H |
| A.1478 | 2,6-Difluoro-benzyl | 2-Cl | H | OCH₂CH=CH₂ | H |
| A.1479 | 3-Trifluoromethyl- | | | | |

TABLE A-continued

| No. | R¹ | R² | R³ | R⁴ | R⁵n |
|---|---|---|---|---|---|
| A.1480 | 3-Cyano-benzyl | 2-Cl | H | OCH$_2$CH=CH$_2$ | H |
| A.1481 | 4-Methyl-benzyl | 2-Cl | H | OCH$_2$CH=CH$_2$ | H |
| A.1482 | 4-Methoxy-carbonyl-benzyl | 2-Cl | H | OCH$_2$CH=CH$_2$ | H |
| A.1483 | 3-Phenyl-benzyl | 2-Cl | H | OCH$_2$CH=CH$_2$ | H |
| A.1484 | (5-Chloro-3-thienyl)-methyl | 2-Cl | H | OCH$_2$CH=CH$_2$ | H |
| A.1485 | (2,5-Di-chloro-3-thienyl)-methyl | 2-Cl | H | OCH$_2$CH=CH$_2$ | H |
| A.1486 | (1,3-Di-oxolan-2-yl)methyl | 2-Cl | H | OCH$_2$CH=CH$_2$ | H |
| A.1487 | 1-Phenyl-ethyl | 2-Cl | H | OCH$_2$CH=CH$_2$ | H |
| A.1488 | 1-(4-Methyl-phenyl)-ethyl | 2-Cl | H | OCH$_2$CH=CH$_2$ | H |
| A.1489 | 1-(4-Chloro-phenyl)-ethyl | 2-Cl | H | OCH$_2$CH=CH$_2$ | H |
| A.1490 | 1-(3-Tri-fluoro-methyl-phenyl)-ethyl | 2-Cl | H | OCH$_2$CH=CH$_2$ | H |
| A.1491 | 2-Phenyl-ethyl | 2-Cl | H | OCH$_2$CH=CH$_2$ | H |
| A.1492 | 3-Phenyl-propan-1-yl | 2-Cl | H | OCH$_2$CH=CH$_2$ | H |
| A.1493 | 4-(4-Chloro-phenyl)-2-butenyl | 2-Cl | H | OCH$_2$CH=CH$_2$ | H |
| A.1494 | Methyl | 2-Cl | H | SCH$_3$ | H |
| A.1495 | Methyl | 2-Cl | H | SCH$_3$ | 3-Cl |
| A.1496 | Methyl | 2-Cl | H | SCH$_3$ | 4-Cl |
| A.1497 | Methyl | 2-Cl | H | SCH$_3$ | 6-Cl |
| A.1498 | Methyl | 2-Cl | H | SCH$_3$ | 3-OCH$_3$ |
| A.1499 | Methyl | 2-Cl | H | SCH$_3$ | 4-OCH$_3$ |
| A.1500 | Methyl | 2-Cl | H | SCH$_3$ | 3-CF$_3$ |
| A.1501 | Methyl | 2-Cl | H | SCH$_3$ | 6-CH$_3$ |
| A.1502 | Methyl | 2-Cl | H | SCH$_3$ | 6-C$_6$H$_5$ |
| A.1503 | Ethyl | 2-Cl | H | SCH$_3$ | H |
| A.1504 | n-Propyl | 2-Cl | H | SCH$_3$ | H |
| A.1505 | i-Propyl | 2-Cl | H | SCH$_3$ | H |
| A.1506 | n-Butyl | 2-Cl | H | SCH$_3$ | H |
| A.1507 | i-Butyl | 2-Cl | H | SCH$_3$ | H |
| A.1508 | sec-Butyl | 2-Cl | H | SCH$_3$ | H |
| A.1509 | tert-Butyl | 2-Cl | H | SCH$_3$ | H |
| A.1510 | n-Pentyl | 2-Cl | H | SCH$_3$ | H |
| A.1511 | n-Hexyl | 2-Cl | H | SCH$_3$ | H |
| A.1512 | 2-Propenyl | 2-Cl | H | SCH$_3$ | H |
| A.1513 | 2-Propenyl | 2-Cl | H | SCH$_3$ | 3-Cl |
| A.1514 | 2-Propenyl | 2-Cl | H | SCH$_3$ | 4-Cl |
| A.1515 | 2-Propenyl | 2-Cl | H | SCH$_3$ | 6-Cl |
| A.1516 | 2-Propenyl | 2-Cl | H | SCH$_3$ | 3-OCH$_3$ |
| A.1517 | 2-Propenyl | 2-Cl | H | SCH$_3$ | 4-OCH$_3$ |
| A.1518 | 2-Propenyl | 2-Cl | H | SCH$_3$ | 3-CF$_3$ |
| A.1519 | 2-Propenyl | 2-Cl | H | SCH$_3$ | 6-CH$_3$ |
| A.1520 | 2-Propenyl | 2-Cl | H | SCH$_3$ | 6-C$_6$H$_5$ |
| A.1521 | (E)-3-Chloro-2-propenyl | 2-Cl | H | SCH$_3$ | H |
| A.1522 | 2-Chloro-2-propenyl | 2-Cl | H | SCH$_3$ | H |
| A.1523 | (E)-2-Butenyl | 2-Cl | H | SCH$_3$ | H |
| A.1524 | 2-Methyl-2-propenyl | 2-Cl | H | SCH$_3$ | H |
| A.1525 | (Z)-3-Chloro-2-butenyl | 2-Cl | H | SCH$_3$ | H |
| A.1526 | 3-Methyl-2-butenyl | 2-Cl | H | SCH$_3$ | H |
| A.1527 | 2-Propynyl | 2-Cl | H | SCH$_3$ | H |
| A.1528 | 2-Propynyl | 2-Cl | H | SCH$_3$ | 3-Cl |
| A.1529 | 2-Propynyl | 2-Cl | H | SCH$_3$ | 4-Cl |
| A.1530 | 2-Propynyl | 2-Cl | H | SCH$_3$ | 6-Cl |
| A.1531 | 2-Propynyl | 2-Cl | H | SCH$_3$ | 3-OCH$_3$ |
| A.1532 | 2-Propynyl | 2-Cl | H | SCH$_3$ | 4-OCH$_3$ |
| A.1533 | 2-Propynyl | 2-Cl | H | SCH$_3$ | 3-CF$_3$ |
| A.1534 | 2-Propynyl | 2-Cl | H | SCH$_3$ | 6-CH$_3$ |
| A.1535 | 2-Propynyl | 2-Cl | H | SCH$_3$ | 6-C$_6$H$_5$ |
| A.1536 | 2-Butynyl | 2-Cl | H | SCH$_3$ | H |
| A.1537 | 3-Butyn-2-yl | 2-Cl | H | SCH$_3$ | H |
| A.1538 | Cyano-methyl | 2-Cl | H | SCH$_3$ | H |
| A.1539 | Methoxy-carbonyl-methyl | 2-Cl | H | SCH$_3$ | H |
| A.1540 | tert-Butoxy-carbonyl-methyl | 2-Cl | H | SCH$_3$ | H |
| A.1541 | 1-(tert-Butoxy-carbonyl)-ethyl | 2-Cl | H | SCH$_3$ | H |
| A.1542 | Cyclo-propyl-methyl | 2-Cl | H | SCH$_3$ | H |
| A.1543 | 1-Methyl-cyclopentyl | 2-Cl | H | SCH$_3$ | H |
| A.1544 | Cyclohexyl | 2-Cl | H | SCH$_3$ | H |
| A.1545 | 1-Methoxy-propan-2-yl | 2-Cl | H | SCH$_3$ | H |
| A.1546 | Benzyl | 2-Cl | H | SCH$_3$ | H |
| A.1547 | Benzyl | 2-Cl | H | SCH$_3$ | 3-Cl |
| A.1548 | Benzyl | 2-Cl | H | SCH$_3$ | 4-Cl |
| A.1549 | Benzyl | 2-Cl | H | SCH$_3$ | 6-Cl |
| A.1550 | Benzyl | 2-Cl | H | SCH$_3$ | 3-OCH$_3$ |
| A.1551 | Benzyl | 2-Cl | H | SCH$_3$ | 4-OCH$_3$ |
| A.1552 | Benzyl | 2-Cl | H | SCH$_3$ | 3-CF$_3$ |
| A.1553 | Benzyl | 2-Cl | H | SCH$_3$ | 6-CH$_3$ |
| A.1554 | Benzyl | 2-Cl | H | SCH$_3$ | 6-C$_6$H$_5$ |
| A.1555 | 3-Methyl-benzyl | 2-Cl | H | SCH$_3$ | H |
| A.1556 | 2-Fluoro-benzyl | 2-Cl | H | SCH$_3$ | H |
| A.1557 | 3-Fluoro-benzyl | 2-Cl | H | SCH$_3$ | H |
| A.1558 | 4-Chloro-benzyl | 2-Cl | H | SCH$_3$ | H |
| A.1559 | 3,4-Di-chloro-benzyl | 2-Cl | H | SCH$_3$ | H |
| A.1560 | 2,6-Di-fluoro-benzyl | 2-Cl | H | SCH$_3$ | H |
| A.1561 | 3-Tri-fluoro-methyl-benzyl | 2-Cl | H | SCH$_3$ | H |
| A.1562 | 3-Cyano-benzyl | 2-Cl | H | SCH$_3$ | H |
| A.1563 | 4-Methyl-benzyl | 2-Cl | H | SCH$_3$ | H |
| A.1564 | 4-Methoxy-carbonyl-benzyl | 2-Cl | H | SCH$_3$ | H |
| A.1565 | 3-Phenyl-benzyl | 2-Cl | H | SCH$_3$ | H |
| A.1566 | (5-Chloro- | 2-Cl | H | SCH$_3$ | H |

TABLE A-continued

| No. | R¹ | R² | R³ | R⁴ | R⁵n |
|---|---|---|---|---|---|
| A.1567 | (2,5-Dichloro-3-thienyl)-methyl | 2-Cl | H | SCH₃ | H |
| A.1568 | (1,3-Dioxolan-2-yl)methyl | 2-Cl | H | SCH₃ | H |
| A.1569 | 1-Phenyl-ethyl | 2-Cl | H | SCH₃ | H |
| A.1570 | 1-(4-Methyl-phenyl)-ethyl | 2-Cl | H | SCH₃ | H |
| A.1571 | 1-(4-Chloro-phenyl)-ethyl | 2-Cl | H | SCH₃ | H |
| A.1572 | 1-(3-Trifluoro-methyl-phenyl)-ethyl | 2-Cl | H | SCH₃ | H |
| A.1573 | 2-Phenyl-ethyl | 2-Cl | H | SCH₃ | H |
| A.1574 | 3-Phenyl-propan-1-yl | 2-Cl | H | SCH₃ | H |
| A.1575 | 4-(4-Chloro-phenyl)-2-butenyl | 2-Cl | H | SCH₃ | H |
| A.1576 | Methyl | 2-Cl | H | Cl | H |
| A.1577 | Methyl | 2-Cl | H | Cl | 3-Cl |
| A.1578 | Methyl | 2-Cl | H | Cl | 4-Cl |
| A.1579 | Methyl | 2-Cl | H | Cl | 6-Cl |
| A.1580 | Methyl | 2-Cl | H | Cl | 3-OCH₃ |
| A.1581 | Methyl | 2-Cl | H | Cl | 4-OCH₃ |
| A.1582 | Methyl | 2-Cl | H | Cl | 3-CF₃ |
| A.1583 | Methyl | 2-Cl | H | Cl | 6-CH₃ |
| A.1584 | Methyl | 2-Cl | H | Cl | 6-C₆H₅ |
| A.1585 | Ethyl | 2-Cl | H | Cl | H |
| A.1586 | n-Propyl | 2-Cl | H | Cl | H |
| A.1587 | i-Propyl | 2-Cl | H | Cl | H |
| A.1588 | n-Butyl | 2-Cl | H | Cl | H |
| A.1589 | i-Butyl | 2-Cl | H | Cl | H |
| A.1590 | sec-Butyl | 2-Cl | H | Cl | H |
| A.1591 | tert-Butyl | 2-Cl | H | Cl | H |
| A.1592 | n-Pentyl | 2-Cl | H | Cl | H |
| A.1593 | n-Hexyl | 2-Cl | H | Cl | H |
| A.1594 | 2-Propenyl | 2-Cl | H | Cl | H |
| A.1595 | 2-Propenyl | 2-Cl | H | Cl | 3-Cl |
| A.1596 | 2-Propenyl | 2-Cl | H | Cl | 4-Cl |
| A.1597 | 2-Propenyl | 2-Cl | H | Cl | 6-Cl |
| A.1598 | 2-Propenyl | 2-Cl | H | Cl | 3-OCH₃ |
| A.1599 | 2-Propenyl | 2-Cl | H | Cl | 4-OCH₃ |
| A.1600 | 2-Propenyl | 2-Cl | H | Cl | 3-CF₃ |
| A.1601 | 2-Propenyl | 2-Cl | H | Cl | 6-CH₃ |
| A.1602 | 2-Propenyl | 2-Cl | H | Cl | 6-C₆H₅ |
| A.1603 | (E)-3-Chloro-2-propenyl | 2-Cl | H | Cl | H |
| A.1604 | 2-Chloro-2-propenyl | 2-Cl | H | Cl | H |
| A.1605 | (E)-2-Butenyl | 2-Cl | H | Cl | H |
| A.1606 | 2-Methyl-2-propenyl | 2-Cl | H | Cl | H |
| A.1607 | (Z)-3-Chloro-2-butenyl | 2-Cl | H | Cl | H |
| A.1608 | 3-Methyl-2-butenyl | 2-Cl | H | Cl | H |
| A.1609 | 2-Propynyl | 2-Cl | H | Cl | H |
| A.1610 | 2-Propynyl | 2-Cl | H | Cl | 3-Cl |
| A.1611 | 2-Propynyl | 2-Cl | H | Cl | 4-Cl |
| A.1612 | 2-Propynyl | 2-Cl | H | Cl | 6-Cl |
| A.1613 | 2-Propynyl | 2-Cl | H | Cl | —OCH₃ |
| A.1614 | 2-Propynyl | 2-Cl | H | Cl | 4-OCH₃ |
| A.1615 | 2-Propynyl | 2-Cl | H | Cl | 3-CF₃ |
| A.1616 | 2-Propynyl | 2-Cl | H | Cl | 6-CH₃ |
| A.1617 | 2-Propynyl | 2-Cl | H | Cl | 6-C₆H₅ |
| A.1618 | 2-Butynyl | 2-Cl | H | Cl | H |
| A.1619 | 3-Butyn-2-yl | 2-Cl | H | Cl | H |
| A.1620 | Cyano-methyl | 2-Cl | H | Cl | H |
| A.1621 | Methoxy-carbonyl-methyl | 2-Cl | H | Cl | H |
| A.1622 | tert-Butoxy-carbonyl-methyl | 2-Cl | H | Cl | H |
| A.1623 | 1-(tert-Butoxy-carbonyl)-ethyl | 2-Cl | H | Cl | H |
| A.1624 | Cyclopropyl-methyl | 2-Cl | H | Cl | H |
| A.1625 | 1-Methyl-cyclopentyl | 2-Cl | H | Cl | H |
| A.1626 | Cyclohexyl | 2-Cl | H | Cl | H |
| A.1627 | 1-Methoxy-propan-2-yl | 2-Cl | H | Cl | H |
| A.1628 | Benzyl | 2-Cl | H | Cl | H |
| A.1629 | Benzyl | 2-Cl | H | Cl | 3-Cl |
| A.1630 | Benzyl | 2-Cl | H | Cl | 4-Cl |
| A.1631 | Benzyl | 2-Cl | H | Cl | 6-Cl |
| A.1632 | Benzyl | 2-Cl | H | Cl | 3-OCH₃ |
| A.1633 | Benzyl | 2-Cl | H | Cl | 4-OCH₃ |
| A.1634 | Benzyl | 2-Cl | H | Cl | 3-CF₃ |
| A.1635 | Benzyl | 2-Cl | H | Cl | 6-CH₃ |
| A.1636 | Benzyl | 2-Cl | H | Cl | 6-C₆H₅ |
| A.1637 | 3-Methyl-benzyl | 2-Cl | H | Cl | H |
| A.1638 | 2-Fluoro-benzyl | 2-Cl | H | Cl | H |
| A.1639 | 3-Fluoro-benzyl | 2-Cl | H | Cl | H |
| A.1640 | 4-Chloro-benzyl | 2-Cl | H | Cl | H |
| A.1641 | 3,4-Dichloro-benzyl | 2-Cl | H | Cl | H |
| A.1642 | 2,6-Difluoro-benzyl | 2-Cl | H | Cl | H |
| A.1643 | 3-Trifluoro-methyl-benzyl | 2-Cl | H | Cl | H |
| A.1644 | 3-Cyano-benzyl | 2-Cl | H | Cl | H |
| A.1645 | 4-Methyl-benzyl | 2-Cl | H | Cl | H |
| A.1646 | 4-Methoxy-carbonyl-benzyl | 2-Cl | H | Cl | H |
| A.1647 | 3-Phenyl-benzyl | 2-Cl | H | Cl | H |
| A.1648 | (5-Chloro-3-thienyl)-methyl | 2-Cl | H | Cl | H |
| A.1649 | (2,5-Dichloro-3-thienyl)-methyl | 2-Cl | H | Cl | H |
| A.1650 | (1,3-Dioxolan-2-yl)methyl | 2-Cl | H | Cl | H |
| A.1651 | 1-Phenyl-ethyl | 2-Cl | H | Cl | H |
| A.1652 | 1-(4- | 2-Cl | H | Cl | H |

TABLE A-continued

| No. | R¹ | R² | R³ | R⁴ | R⁵n |
|---|---|---|---|---|---|
| | Methyl-phenyl)-ethyl | | | | |
| A.1653 | 1-(4-Chloro-phenyl)-ethyl | 2-Cl | H | Cl | H |
| A.1654 | 1-(3-Tri-fluoro-methyl-phenyl)-ethyl | 2-Cl | H | Cl | H |
| A.1655 | 2-Phenyl-ethyl | 2-Cl | H | Cl | H |
| A.1656 | 3-Phenyl-propan-1-yl | 2-Cl | H | Cl | H |
| A.1657 | 4-(4-Chloro-phenyl)-2-butenyl | 2-Cl | H | Cl | H |
| A.1658 | Methyl | 2-Cl | H | Br | H |
| A.1659 | Methyl | 2-Cl | H | Br | 3-Cl |
| A.1660 | Methyl | 2-Cl | H | Br | 4-Cl |
| A.1661 | Methyl | 2-Cl | H | Br | 6-Cl |
| A.1662 | Methyl | 2-Cl | H | Br | 3-OCH₃ |
| A.1663 | Methyl | 2-Cl | H | Br | 4-OCH₃ |
| A.1664 | Methyl | 2-Cl | H | Br | 3-CF₃ |
| A.1665 | Methyl | 2-Cl | H | Br | 6-CH₃ |
| A.1666 | Methyl | 2-Cl | H | Br | 6-C₆H₅ |
| A.1667 | Ethyl | 2-Cl | H | Br | H |
| A.1668 | n-Propyl | 2-Cl | H | Br | H |
| A.1669 | i-Propyl | 2-Cl | H | Br | H |
| A.1670 | n-Butyl | 2-Cl | H | Br | H |
| A.1671 | i-Butyl | 2-Cl | H | Br | H |
| A.1672 | sec-Butyl | 2-Cl | H | Br | H |
| A.1673 | tert-Butyl | 2-Cl | H | Br | H |
| A.1674 | n-Pentyl | 2-Cl | H | Br | H |
| A.1675 | n-Hexyl | 2-Cl | H | Br | H |
| A.1676 | 2-Propenyl | 2-Cl | H | Br | H |
| A.1677 | 2-Propenyl | 2-Cl | H | Br | 3-Cl |
| A.1678 | 2-Propenyl | 2-Cl | H | Br | 4-Cl |
| A.1679 | 2-Propenyl | 2-Cl | H | Br | 6-Cl |
| A.1680 | 2-Propenyl | 2-Cl | H | Br | 3-OCH₃ |
| A.1661 | 2-Propenyl | 2-Cl | H | Br | 4-OCH₃ |
| A.1682 | 2-Propenyl | 2-Cl | H | Br | 3-CF₃ |
| A.1683 | 2-Propenyl | 2-Cl | H | Br | 6-CH₃ |
| A.1684 | 2-Propenyl | 2-Cl | H | Br | 6-C₆H₅ |
| A.1685 | (E)-3-Chloro-2-propenyl | 2-Cl | H | Br | H |
| A.1686 | 2-Chloro-2-propenyl | 2-Cl | H | Br | H |
| A.1687 | (E)-2-Butenyl | 2-Cl | H | Br | H |
| A.1688 | 2-Methyl-2-propenyl | 2-Cl | H | Br | H |
| A.1689 | (Z)-3-Chloro-2-butenyl | 2-Cl | H | Br | H |
| A.1690 | 3-Methyl-2-butenyl | 2-Cl | H | Br | H |
| A.1691 | 2-Propynyl | 2-Cl | H | Br | H |
| A.1692 | 2-Propynyl | 2-Cl | H | Br | 3-Cl |
| A.1693 | 2-Propynyl | 2-Cl | H | Br | 4-Cl |
| A.1694 | 2-Propynyl | 2-Cl | H | Br | 6-Cl |
| A.1695 | 2-Propynyl | 2-Cl | H | Br | 3-OCH₃ |
| A.1696 | 2-Propynyl | 2-Cl | H | Br | 4-OCH₃ |
| A.1697 | 2-Propynyl | 2-Cl | H | Br | 3-CF₃ |
| A.1698 | 2-Propynyl | 2-Cl | H | Br | 6-CH₃ |
| A.1699 | 2-Propynyl | 2-Cl | H | Br | 6-C₆H₅ |
| A.1700 | 2-Butynyl | 2-Cl | H | Br | H |
| A.1701 | 3-Butyn-2-yl | 2-Cl | H | Br | H |
| A.1702 | Cyano-methyl | 2-Cl | H | Br | H |
| A.1703 | Methoxy-carbonyl-methyl | 2-Cl | H | Br | H |
| A.1704 | t-Butoxy-carbonyl-methyl | 2-Cl | H | Br | H |
| A.1705 | 1-(tert-Butoxy-carbonyl)-ethyl | 2-Cl | H | Br | H |
| A.1706 | Cyclo-propyl-methyl | 2-Cl | H | Br | H |
| A.1707 | 1-Methyl-cyclopentyl | 2-Cl | H | Br | H |
| A.1708 | Cyclohexyl | 2-Cl | H | Br | H |
| A.1709 | 1-Methoxy-propan-2-yl | 2-Cl | H | Br | H |
| A.1710 | Benzyl | 2-Cl | H | Br | H |
| A.1711 | Benzyl | 2-Cl | H | Br | 3-Cl |
| A.1712 | Benzyl | 2-Cl | H | Br | 4-Cl |
| A.1713 | Benzyl | 2-Cl | H | Br | 6-Cl |
| A.1714 | Benzyl | 2-Cl | H | Br | 3-OCH₃ |
| A.1715 | Benzyl | 2-Cl | H | Br | 4-OCH₃ |
| A.1716 | Benzyl | 2-Cl | H | Br | 3-CF₃ |
| A.1717 | Benzyl | 2-Cl | H | Br | 6-CH₃ |
| A.1718 | Benzyl | 2-Cl | H | Br | 6-C₆H₅ |
| A.1719 | 3-Methyl-benzyl | 2-Cl | H | Br | H |
| A.1720 | 2-Fluoro-benzyl | 2-Cl | H | Br | H |
| A.1721 | 3-Fluoro-benzyl | 2-Cl | H | Br | H |
| A.1722 | 4-Chloro-benzyl | 2-Cl | H | Br | H |
| A.1723 | 3,4-Di-chloro-benzyl | 2-Cl | H | Br | H |
| A.1724 | 2,6-Di-fluoro-benzyl | 2-Cl | H | Br | H |
| A.1725 | 3-Tri-fluoro-methyl-benzyl | 2-Cl | H | Br | H |
| A.1726 | 3-Cyano-benzyl | 2-Cl | H | Br | H |
| A.1727 | 4-Methyl-benzyl | 2-Cl | H | Br | H |
| A.1728 | 4-Methoxy-carbonyl-benzyl | 2-Cl | H | Br | H |
| A.1729 | 3-Phenyl-benzyl | 2-Cl | H | Br | H |
| A.1730 | (5-Chloro-3-thienyl)-methyl | 2-Cl | H | Br | H |
| A.1731 | (2,5-Di-chloro-3-thienyl)-methyl | 2-Cl | H | Br | H |
| A.1732 | (1,3-Di-oxolan-2-yl)methyl | 2-Cl | H | Br | H |
| A.1733 | 1-Phenyl-ethyl | 2-Cl | H | Br | H |
| A.1734 | 1-(4-Methyl-phenyl)-ethyl | 2-Cl | H | Br | H |
| A.1735 | 1-(4-Chloro-phenyl)-ethyl | 2-Cl | H | Br | H |
| A.1736 | 1-(3-Tri-fluoro-methyl-phenyl)-ethyl | 2-Cl | H | Br | H |
| A.1737 | 2-Phenyl- | 2-Cl | H | Br | H |

TABLE A-continued

| No. | R¹ | R² | R³ | R⁴ | R⁵n |
|---|---|---|---|---|---|
| A.1738 | 3-Phenyl-propan-1-yl | 2-Cl | H | Br | H |
| A.1739 | 4-(4-Chloro-phenyl)-2-butenyl | 2-Cl | H | Br | H |
| A.1740 | Methyl | 2-Cl | H | CN | H |
| A.1741 | Methyl | 2-Cl | H | CN | 3-Cl |
| A.1742 | Methyl | 2-Cl | H | CN | 4-Cl |
| A.1743 | Methyl | 2-Cl | H | CN | 6-Cl |
| A.1744 | Methyl | 2-Cl | H | CN | 3-OCH₃ |
| A.1745 | Methyl | 2-Cl | H | CN | 4-OCH₃ |
| A.1746 | Methyl | 2-Cl | H | CN | 3-CF₃ |
| A.1747 | Methyl | 2-Cl | H | CN | 6-CH₃ |
| A.1748 | Methyl | 2-Cl | H | CN | 6-C₆H₅ |
| A.1749 | Ethyl | 2-Cl | H | CN | H |
| A.1750 | n-Propyl | 2-Cl | H | CN | H |
| A.1751 | i-Propyl | 2-Cl | H | CN | H |
| A.1752 | n-Butyl | 2-Cl | H | CN | H |
| A.1753 | i-Butyl | 2-Cl | H | CN | H |
| A.1754 | sec-Butyl | 2-Cl | H | CN | H |
| A.1755 | tert-Butyl | 2-Cl | H | CN | H |
| A.1756 | n-Pentyl | 2-Cl | H | CN | H |
| A.1757 | n-Hexyl | 2-Cl | H | CN | H |
| A.1758 | 2-Propenyl | 2-Cl | H | CN | H |
| A.1759 | 2-Propenyl | 2-Cl | H | CN | 3-Cl |
| A.1760 | 2-Propenyl | 2-Cl | H | CN | 4-Cl |
| A.1761 | 2-Propenyl | 2-Cl | H | CN | 6-Cl |
| A.1762 | 2-Propenyl | 2-Cl | H | CN | 3-OCH₃ |
| A.1763 | 2-Propenyl | 2-Cl | H | CN | 4-OCH₃ |
| A.1764 | 2-Propenyl | 2-Cl | H | CN | 3-CF₃ |
| A.1765 | 2-Propenyl | 2-Cl | H | CN | 6-CH₃ |
| A.1766 | 2-Propenyl | 2-Cl | H | CN | 6-C₆H₅ |
| A.1767 | (E)-3-chloro-2-propenyl | 2-Cl | H | CN | H |
| A.1768 | 2-chloro-2-propenyl | 2-Cl | H | CN | H |
| A.1769 | (E)-2-Butenyl | 2-Cl | H | CN | H |
| A.1770 | 2-Methyl-2-propenyl | 2-Cl | H | CN | H |
| A.1771 | (Z)-3-Chloro-2-butenyl | 2-Cl | H | CN | H |
| A.1772 | 3-Methyl-2-butenyl | 2-Cl | H | CN | H |
| A.1773 | 2-Propynyl | 2-Cl | H | CN | H |
| A.1774 | 2-Propynyl | 2-Cl | H | CN | 3-Cl |
| A.1775 | 2-Propynyl | 2-Cl | H | CN | 4-Cl |
| A.1776 | 2-Propynyl | 2-Cl | H | CN | 6-Cl |
| A.1777 | 2-Propynyl | 2-Cl | H | CN | 3-OCH₃ |
| A.1778 | 2-Propynyl | 2-Cl | H | CN | 4-OCH₃ |
| A.1779 | 2-Propynyl | 2-Cl | H | CN | 3-CF₃ |
| A.1780 | 2-Propynyl | 2-Cl | H | CN | 6-4CH₃ |
| A.1781 | 2-Propynyl | 2-Cl | H | CN | 6-C₆H₅ |
| A.1782 | 2-Butynyl | 2-Cl | H | CN | H |
| A.1783 | 3-Butyn-2-yl | 2-Cl | H | CN | H |
| A.1784 | Cyano-methyl | 2-Cl | H | CN | H |
| A.1785 | Methoxy-carbonyl-methyl | 2-Cl | H | CN | H |
| A.1786 | tert-Butoxy-carbonyl-methyl | 2-Cl | H | CN | H |
| A.1787 | 1-(tert-Butoxy-carbonyl)-ethyl | 2-Cl | H | CN | H |
| A.1788 | Cyclopropyl-methyl | 2-Cl | H | CN | H |
| A.1789 | 1-Methyl-cyclopentyl | 2-Cl | H | CN | H |
| A.1790 | Cyclohexyl | 2-Cl | H | CN | H |
| A.1791 | 1-Methoxy-propan-2-yl | 2-Cl | H | CN | H |
| A.1792 | Benzyl | 2-Cl | H | CN | H |
| A.1793 | Benzyl | 2-Cl | H | CN | 3-Cl |
| A.1794 | Benzyl | 2-Cl | H | CN | 4-Cl |
| A.1795 | Benzyl | 2-Cl | H | CN | 6-Cl |
| A.1796 | Benzyl | 2-Cl | H | CN | 3-OCH₃ |
| A.1797 | Benzyl | 2-Cl | H | CN | 4-OCH₃ |
| A.1798 | Benzyl | 2-Cl | H | CN | 3-CF₃ |
| A.1799 | Benzyl | 2-Cl | H | CN | 6-CH₃ |
| A.1800 | Benzyl | 2-Cl | H | CN | 6-C₆H₅ |
| A.1801 | 3-Methyl-benzyl | 2-Cl | H | CN | H |
| A.1802 | 2-Fluoro-benzyl | 2-Cl | H | CN | H |
| A.1803 | 3-Fluoro-benzyl | 2-Cl | H | CN | H |
| A.1804 | 4-Chloro-benzyl | 2-Cl | H | CN | H |
| A.1805 | 3,4-Di-chloro-benzyl | 2-Cl | H | CN | H |
| A.1806 | 2,6-Di-fluoro-benzyl | 2-Cl | H | CN | H |
| A.1807 | 3-Tri-fluoro-methyl-benzyl | 2-Cl | H | CN | H |
| A.1808 | 3-Cyano-benzyl | 2-Cl | H | CN | H |
| A.1809 | 4-Methyl-benzyl | 2-Cl | H | CN | H |
| A.1810 | 4-Methoxy-carbonyl-benzyl | 2-Cl | H | CN | H |
| A.1811 | 3-Phenyl-benzyl | 2-Cl | H | CN | H |
| A.1812 | (5-Chloro-3-thienyl)-methyl | 2-Cl | H | CN | H |
| A.1813 | (2,5-Di-chloro-3-thienyl)-methyl | 2-Cl | H | CN | H |
| A.1814 | (1,3-Di-oxolan-2-yl)methyl | 2-Cl | H | CN | H |
| A.1815 | 1-Phenyl-ethyl | 2-Cl | H | CN | H |
| A.1816 | 1-(4-Methyl-phenyl)-ethyl | 2-Cl | H | CN | H |
| A.1817 | 1-(4-Chloro-phenyl)-ethyl | 2-Cl | H | CN | H |
| A.1818 | 1-(3-Tri-fluoro-methyl-phenyl)-ethyl | 2-Cl | H | CN | H |
| A.1819 | 2-Phenyl-ethyl | 2-Cl | H | CN | H |
| A.1820 | 3-Phenyl-propan-1-yl | 2-Cl | H | CN | H |
| A.1821 | 4-(4-Chloro-phenyl)-2-butenyl | 2-Cl | H | CN | H |
| A.1822 | Methyl | 2-Cl | H | OCH₂C≡CH | H |
| A.1823 | Ethyl | 2-Cl | H | OCH₂C≡CH | H |
| A.1824 | 2-Propenyl | 2-Cl | H | OCH₂C≡CH | H |
| A.1825 | 2-Propynyl | 2-Cl | H | OCH₂C≡CH | H |

TABLE A-continued

| No. | R¹ | R² | R³ | R⁴ | R⁵n |
|---|---|---|---|---|---|
| A.1826 | 1-(tert-Butoxycarbonyl)-ethyl | 2-Cl | H | OCH$_2$C≡CH | H |
| A.1827 | 3-Methylbenzyl | 2-Cl | H | OCH$_2$C≡CH | H |
| A.1828 | 1-Phenylethyl | 2-Cl | H | OCH$_2$C≡CH | H |
| A.1829 | Methyl | 2-Cl | H | OCH$_2$CH$_2$C$_6$H$_5$ | H |
| A.1830 | Ethyl | 2-Cl | H | OCH$_2$CH$_2$C$_6$H$_5$ | H |
| A.1831 | 2-Propenyl | 2-Cl | H | OCH$_2$CH$_2$C$_6$H$_5$ | H |
| A.1832 | 2-Propynyl | 2-Cl | H | OCH$_2$CH$_2$C$_6$H$_5$ | H |
| A.1833 | 1-(tert-Butoxycarbonyl)-ethyl | 2-Cl | H | OCH$_2$CH$_2$C$_6$H$_5$ | H |
| A.1834 | 3-Methylbenzyl | 2-Cl | H | OCH$_2$CH$_2$C$_6$H$_5$ | H |
| A.1835 | 1-Phenylethyl | 2-Cl | H | OCH$_2$CH$_2$C$_6$H$_5$ | H |
| A.1836 | Methyl | 2-Cl | H | SCH$_2$CH$_3$ | H |
| A.1837 | Ethyl | 2-Cl | H | SCH$_2$CH$_3$ | H |
| A.1838 | 2-Propenyl | 2-Cl | H | SCH$_2$CH$_3$ | H |
| A.1839 | 2-Propynyl | 2-Cl | H | SCH$_2$CH$_3$ | H |
| A.1840 | 1-(tert-Butoxycarbonyl)-ethyl | 2-Cl | H | SCH$_2$CH$_3$ | H |
| A.1841 | 3-Methylbenzyl | 2-Cl | H | SCH$_2$CH$_3$ | H |
| A.1842 | 1-Phenylethyl | 2-Cl | H | SCH$_2$CH$_3$ | H |
| A.1843 | Methyl | 2-Cl | H | NH—CH$_3$ | H |
| A.1844 | Ethyl | 2-Cl | H | NH—CH$_3$ | H |
| A.1845 | 2-Propenyl | 2-Cl | H | NH—CH$_3$ | H |
| A.1846 | 2-Propynyl | 2-Cl | H | NH—CH$_3$ | H |
| A.1847 | 1-(tert-Butoxycarbonyl)-ethyl | 2-Cl | H | NH—CH$_3$ | H |
| A.1848 | 3-Methylbenzyl | 2-Cl | H | NH—CH$_3$ | H |
| A.1849 | 1-Phenylethyl | 2-Cl | H | NH—CH$_3$ | H |
| A.1850 | Methyl | 2-Cl | H | N(CH$_3$)$_2$ | H |
| A.1851 | Ethyl | 2-Cl | H | N(CH$_3$)$_2$ | H |
| A.1852 | 2-Propenyl | 2-Cl | H | N(CH$_3$)$_2$ | H |
| A.1853 | 2-Propynyl | 2-Cl | H | N(CH$_3$)$_2$ | H |
| A.1854 | 1-(tert-Butoxycarbonyl)-ethyl | 2-Cl | H | N(CH$_3$)$_2$ | H |
| A.1855 | 3-Methylbenzyl | 2-Cl | H | N(CH$_3$)$_2$ | H |
| A.1856 | 1-Phenylethyl | 2-Cl | H | N(CH$_3$)$_2$ | H |
| A.1857 | Methyl | 2-Cl | H | OC$_6$H$_5$ | H |
| A.1858 | Ethyl | 2-Cl | H | OC$_6$H$_5$ | H |
| A.1859 | 2-Propenyl | 2-Cl | H | OC$_6$H$_5$ | H |
| A.1860 | 2-Propynyl | 2-Cl | H | OC$_6$H$_5$ | H |
| A.1861 | 1-(tert-Butoxycarbonyl)-ethyl | 2-Cl | H | OC$_6$H$_5$ | H |
| A.1862 | 3-Methylbutyl | 2-Cl | H | OC$_6$H$_5$ | H |
| A.1863 | 1-Phenethyl | 2-Cl | H | OC$_6$H$_5$ | H |
| A.1864 | Methyl | 2-Cl | H | SC$_6$H$_5$ | H |
| A.1865 | Ethyl | 2-Cl | H | SC$_6$H$_5$ | H |
| A.1866 | 2-Propenyl | 2-Cl | H | SC$_6$H$_5$ | H |
| A.1867 | 2-Propynyl | 2-Cl | H | SC$_6$H$_5$ | H |
| A.1868 | 1-(tert-Butoxycarbonyl)-ethyl | 2-Cl | H | SC$_6$H$_5$ | H |
| A.1869 | 3-Methylbenzyl | 2-Cl | H | SC$_6$H$_5$ | H |
| A.1870 | 1-Phenylethyl | 2-Cl | H | SC$_6$H$_5$ | H |
| A.1871 | Methyl | 2-F | H | OCH$_3$ | H |
| A.1872 | Methyl | 2-F | H | SCH$_3$ | H |
| A.1873 | Methyl | 2-F | H | Cl | H |
| A.1874 | Methyl | 2-F | H | Br | H |
| A.1875 | Methyl | 2-F | H | OC$_6$H$_5$ | H |
| A.1876 | Methyl | 2-F | H | SC$_6$H$_5$ | H |
| A.1877 | Ethyl | 2-F | H | OCH$_3$ | H |
| A.1878 | Ethyl | 2-F | H | OCH$_3$ | 3-Cl |
| A.1879 | Ethyl | 2-F | H | OCH$_3$ | 3-OCH$_3$ |
| A.1880 | Ethyl | 2-F | H | SCH$_3$ | H |
| A.1881 | Ethyl | 2-F | H | Cl | H |
| A.1882 | Ethyl | 2-F | H | Br | H |
| A.1883 | Ethyl | 2-F | H | OC$_6$H$_5$ | H |
| A.1884 | Ethyl | 2-F | H | SC$_6$H$_5$ | H |
| A.1885 | 2-Propenyl | 2-F | H | OCH$_3$ | H |
| A.1886 | 2-Propenyl | 2-F | H | SCH$_3$ | H |
| A.1887 | 2-Propenyl | 2-F | H | Cl | H |
| A.1888 | 2-Propenyl | 2-F | H | Br | H |
| A.1889 | Benzyl | 2-F | H | OCH$_3$ | H |
| A.1890 | Benzyl | 2-F | H | SCH$_3$ | H |
| A.1891 | Benzyl | 2-F | H | Cl | H |
| A.1892 | Benzyl | 2-F | H | Br | H |
| A.1893 | Methyl | 2-CN | H | OCH$_3$ | H |
| A.1894 | Methyl | 2-CN | H | SCH$_3$ | H |
| A.1895 | Methyl | 2-CN | H | Cl | H |
| A.1896 | Methyl | 2-CN | H | Br | H |
| A.1897 | Methyl | 2-CN | H | OC$_6$H$_5$ | H |
| A.1898 | Methyl | 2-CN | H | SC$_6$H$_5$ | H |
| A.1899 | Ethyl | 2-CN | H | OCH$_3$ | H |
| A.1900 | Ethyl | 2-CN | H | OCH$_3$ | 3-Cl |
| A.1901 | Ethyl | 2-CN | H | OCH$_3$ | 3-OCH$_3$ |
| A.1902 | Ethyl | 2-CN | H | SCH$_3$ | H |
| A.1903 | Ethyl | 2-CN | H | Cl | H |
| A.1904 | Ethyl | 2-CN | H | Br | H |
| A.1905 | Ethyl | 2-CN | H | OC$_6$H$_5$ | H |
| A.1906 | Ethyl | 2-CN | H | SC$_6$H$_5$ | H |
| A.1907 | 2-Propenyl | 2-CN | H | OCH$_3$ | H |
| A.1908 | 2-Propenyl | 2-CN | H | SCH$_3$ | H |
| A.1909 | 2-Propenyl | 2-CN | H | Cl | H |
| A.1910 | 2-Propenyl | 2-CN | H | Br | H |
| A.1911 | Benzyl | 2-CN | H | OCH$_3$ | H |
| A.1912 | Benzyl | 2-CN | H | SCH$_3$ | H |
| A.1913 | Benzyl | 2-CN | H | Cl | H |
| A.1914 | Benzyl | 2-CN | H | Br | H |
| A.1915 | Methyl | 5-CH$_3$ | H | OCH$_3$ | H |
| A.1916 | Methyl | 5-CH$_3$ | H | SCH$_3$ | H |
| A.1917 | Methyl | 5-CH$_3$ | H | Cl | H |
| A.1918 | Methyl | 5-CH$_3$ | H | Br | H |
| A.1919 | Methyl | 5-CH$_3$ | H | OC$_6$H$_5$ | H |
| A.1920 | Methyl | 5-CH$_3$ | H | SC$_6$H$_5$ | H |
| A.1921 | Ethyl | 5-CH$_3$ | H | OCH$_3$ | H |
| A.1922 | Ethyl | 5-CH$_3$ | H | OCH$_3$ | 3-Cl |
| A.1923 | Ethyl | 5-CH$_3$ | H | OCH$_3$ | 3-OCH$_3$ |
| A.1924 | Ethyl | 5-CH$_3$ | H | SCH$_3$ | H |
| A.1925 | Ethyl | 5-CH$_3$ | H | Cl | H |
| A.1926 | Ethyl | 5-CH$_3$ | H | Br | H |
| A.1927 | Ethyl | 5-CH$_3$ | H | OC$_6$H$_5$ | H |
| A.1928 | Ethyl | 5-CH$_3$ | H | SC$_6$H$_5$ | H |
| A.1929 | 2-Propenyl | 5-CH$_3$ | H | OCH$_3$ | H |
| A.1930 | 2-Propenyl | 5-CH$_3$ | H | SCH$_3$ | H |
| A.1931 | 2-Propenyl | 5-CH$_3$ | H | Cl | H |
| A.1932 | 2-Propenyl | 5-CH$_3$ | H | Br | H |
| A.1933 | Benzyl | 5-CH$_3$ | H | OCH$_3$ | H |
| A.1934 | Benzyl | 5-CH$_3$ | H | SCH$_3$ | H |
| A.1935 | Benzyl | 5-CH$_3$ | H | Cl | H |
| A.1936 | Benzyl | 5-CH$_3$ | H | Br | H |
| A.1937 | Methyl | 2-Cl | 5-Cl | OCH$_3$ | H |
| A.1938 | Methyl | 2-Cl | 5-Cl | SCH$_3$ | H |
| A.1939 | Methyl | 2-Cl | 5-Cl | Cl | H |
| A.1940 | Methyl | 2-Cl | 5-Cl | Br | H |
| A.1941 | Methyl | 2-Cl | 5-Cl | OC$_6$H$_5$ | H |
| A.1942 | Methyl | 2-Cl | 5-Cl | SC$_6$H$_5$ | H |
| A.1943 | Methyl | 2-Cl | 5-Cl | OCH$_3$ | H |
| A.1944 | Methyl | 2-Cl | 5-Cl | OCH$_3$ | 3-Cl |
| A.1945 | Methyl | 2-Cl | 5-Cl | OCH$_3$ | 3-OCH$_3$ |

TABLE A-continued

| No. | R¹ | R² | R³ | R⁴ | (R⁵)n |
|---|---|---|---|---|---|
| A.1946 | Methyl | 2-Cl | 5-Cl | SCH₃ | H |
| A.1947 | Methyl | 2-Cl | 5-Cl | Cl | H |
| A.1948 | Methyl | 2-Cl | 5-Cl | Br | H |
| A.1949 | Methyl | 2-Cl | 5-Cl | OC₆H₅ | H |
| A.1950 | Methyl | 2-Cl | 5-Cl | SC₆H₅ | H |
| A.1951 | 2-Propenyl | 2-Cl | 5-Cl | OCH₃ | H |
| A.1952 | 2-Propenyl | 2-Cl | 5-Cl | SCH₃ | H |
| A.1953 | 2-Propenyl | 2-Cl | 5-Cl | Cl | H |
| A.1954 | 2-Propenyl | 2-Cl | 5-Cl | Br | H |
| A.1955 | Benzyl | 2-Cl | 5-Cl | OCH₃ | H |
| A.1956 | Benzyl | 2-Cl | 5-Cl | SCH₃ | H |
| A.1957 | Benzyl | 2-Cl | 5-Cl | Cl | H |
| A.1958 | Benzyl | 2-Cl | 5-Cl | Br | H |

TABLE B

| No. | R¹ | R² | R³ | R⁴ | (R⁵)n |
|---|---|---|---|---|---|
| B.001 | Methyl | 2-CH₃ | H | OCH₃ | H |
| B.002 | Methyl | 2-CH₃ | H | OCH₃ | 3-Cl |
| B.003 | Methyl | 2-CH₃ | H | OCH₃ | 4-Cl |
| B.004 | Methyl | 2-CH₃ | H | OCH₃ | 6-Cl |
| B.005 | Methyl | 2-CH₃ | H | OCH₃ | 3-OCH₃ |
| B.006 | methyl | 2-CH₃ | H | OCH₃ | 6-CH₃ |
| B.007 | Ethyl | 2-CH₃ | H | OCH₃ | H |
| B.008 | i-Propyl | 2-CH₃ | H | OCH₃ | H |
| B.009 | 2-Propenyl | 2-CH₃ | H | OCH₃ | H |
| B.010 | 2-Propenyl | 2-CH₃ | H | OCH₃ | 3-Cl |
| B.011 | (E)-3-Chloro-2-propenyl | 2-CH₃ | H | OCH₃ | H |
| B.012 | 2-Propynyl | 2-CH₃ | H | OCH₃ | H |
| B.013 | 2-Propynyl | 2-CH₃ | H | OCH₃ | 3-Cl |
| B.014 | 2-Propynyl | 2-CH₃ | H | OCH₃ | 3-OCH₃ |
| B.015 | 2-Propynyl | 2-CH₃ | H | OCH₃ | 6-CH₃ |
| B.016 | Cyanomethyl | 2-CH₃ | H | OCH₃ | H |
| B.017 | 1-(tert-Butoxycarbonyl)-ethyl | 2-CH₃ | H | OCH₃ | H |
| B.018 | Cyclopropylmethyl | 2-CH₃ | H | OCH₃ | H |
| B.019 | Benzyl | 2-CH₃ | H | OCH₃ | H |
| B.020 | 3-Methylbenzyl | 2-CH₃ | H | OCH₃ | H |
| B.021 | 3-Methylbenzyl | 2-CH₃ | H | OCH₃ | 3-Cl |
| B.022 | 1-(4-Chlorophenyl)-ethyl | 2-CH₃ | H | OCH₃ | H |
| B.023 | 4-(4-Chlorophenyl)-2-butenyl | 2-CH₃ | H | OCH₃ | H |
| B.024 | Methyl | 2-CH₃ | H | OC₂H₅ | H |
| B.025 | Methyl | 2-CH₃ | H | OC₂H₅ | 3-Cl |
| B.026 | Methyl | 2-CH₃ | H | OC₂H₅ | 4-Cl |
| B.027 | Methyl | 2-CH₃ | H | OC₂H₅ | 6-Cl |
| B.028 | Methyl | 2-CH₃ | H | OC₂H₅ | 3-OCH₃ |
| B.029 | Methyl | 2-CH₃ | H | OC₂H₅ | 6-CH₃ |
| B.030 | Ethyl | 2-CH₃ | H | OC₂H₅ | H |
| B.031 | i-Propyl | 2-CH₃ | H | OC₂H₅ | H |
| B.032 | 2-Propenyl | 2-CH₃ | H | OC₂H₅ | H |
| B.033 | 2-Propenyl | 2-CH₃ | H | OC₂H₅ | 3-Cl |
| B.034 | (E)-3-Chloro-2-propenyl | 2-CH₃ | H | OC₂H₅ | H |
| B.035 | 2-Propynyl | 2-CH₃ | H | OC₂H₅ | H |
| B.036 | 2-Propynyl | 2-CH₃ | H | OC₂H₅ | 3-Cl |
| B.037 | 2-Propynyl | 2-CH₃ | H | OC₂H₅ | 3-OCH₃ |
| B.038 | 2-Propynyl | 2-CH₃ | H | OC₂H₅ | 6-CH₃ |
| B.039 | Cyanomethyl | 2-CH₃ | H | OC₂H₅ | H |
| B.040 | 1-(tert-Butoxycarbonyl)-ethyl | 2-CH₃ | H | OC₂H₅ | H |
| B.041 | Cyclopropylmethyl | 2-CH₃ | H | OC₂H₅ | H |
| B.042 | Benzyl | 2-CH₃ | H | OC₂H₅ | H |
| B.043 | 3-Methylbenzyl | 2-CH₃ | H | OC₂H₅ | H |
| B.044 | 3-Methylbenzyl | 2-CH₃ | H | OC₂H₅ | 3-Cl |
| B.045 | 1-(4-Chlorophenyl)-ethyl | 2-CH₃ | H | OC₂H₅ | H |
| B.046 | 4-(4-Chlorophenyl)-2-butenyl | 2-CH₃ | H | OC₂H₅ | H |
| B.047 | Methyl | 2-CH₃ | H | Cl | H |
| B.048 | Methyl | 2-CH₃ | H | Cl | 3-Cl |
| B.049 | Methyl | 2-CH₃ | H | Cl | 4-Cl |
| B.050 | Methyl | 2-CH₃ | H | Cl | 6-Cl |
| B.051 | Methyl | 2-CH₃ | H | Cl | 3-CH₃ |
| B.052 | Methyl | 2-CH₃ | H | Cl | 6-CH₃ |
| B.053 | Ethyl | 2-CH₃ | H | Cl | H |
| B.054 | i-Propyl | 2-CH₃ | H | Cl | H |
| B.055 | 2-Propenyl | 2-CH₃ | H | Cl | H |
| B.056 | 2-Propenyl | 2-CH₃ | H | Cl | 3-Cl |
| B.057 | (E)-3-Chloro-2-propenyl | 2-CH₃ | H | Cl | H |
| B.058 | 2-Propynyl | 2-CH₃ | H | Cl | H |
| B.059 | 2-Propynyl | 2-CH₃ | H | Cl | 3-Cl |
| B.060 | 2-Propynyl | 2-CH₃ | H | Cl | 3-OCH₃ |
| B.061 | 2-Propynyl | 2-CH₃ | H | Cl | 6-CH₃ |
| B.062 | Cyanomethyl | 2-CH₃ | H | Cl | H |
| B.063 | 1-(tert-Butoxycarbonyl)-ethyl | 2-CH₃ | H | Cl | H |
| B.064 | Cyclopropylmethyl | 2-CH₃ | H | Cl | H |
| B.065 | Benzyl | 2-CH₃ | H | Cl | H |
| B.066 | 3-Methylbenzyl | 2-CH₃ | H | Cl | H |
| B.067 | 3-Methylbenzyl | 2-CH₃ | H | Cl | 3-Cl |
| B.068 | 1-(4-Chlorophenyl)-ethyl | 2-CH₃ | H | Cl | H |
| B.069 | 4-(4-Chlorophenyl)-2-butenyl | 2-CH₃ | H | Cl | H |
| B.070 | Methyl | 2-CH₃ | H | SCH₃ | H |
| B.071 | Methyl | 2-CH₃ | H | SCH₃ | 3-Cl |
| B.072 | Methyl | 2-CH₃ | H | SCH₃ | 4-Cl |
| B.073 | Methyl | 2-CH₃ | H | SCH₃ | 6-Cl |
| B.074 | Methyl | 2-CH₃ | H | SCH₃ | 3-OCH₃ |
| B.075 | Methyl | 2-CH₃ | H | SCH₃ | 6-CH₃ |
| B.076 | Ethyl | 2-CH₃ | H | SCH₃ | H |
| B.077 | i-Propyl | 2-CH₃ | H | SCH₃ | H |
| B.078 | 2-Propenyl | 2-CH₃ | H | SCH₃ | H |
| B.079 | 2-Propenyl | 2-CH₃ | H | SCH₃ | 3-Cl |
| B.080 | (E)-3-Chloro-2-propenyl | 2-CH₃ | H | SCH₃ | H |
| B.081 | 2-Propynyl | 2-CH₃ | H | SCH₃ | H |
| B.082 | 2-Propynyl | 2-CH₃ | H | SCH₃ | 3-Cl |
| B.083 | 2-Propynyl | 2-CH₃ | H | SCH₃ | 3-OCH₃ |
| B.084 | 2-Propynyl | 2-CH₃ | H | SCH₃ | 6-CH₃ |

TABLE B-continued

| No. | R¹ | R² | R³ | R⁴ | (R⁵)n |
|---|---|---|---|---|---|
| B.085 | Cyanomethyl | 2-CH₃ | H | SCH₃ | H |
| B.086 | 1-(tert-Butoxycarbonyl)-ethyl | 2-CH₃ | H | SCH₃ | H |
| B.087 | Cyclopropylmethyl | 2-CH₃ | H | SCH₃ | H |
| B.088 | Benzyl | 2-CH₃ | H | SCH₃ | H |
| B.089 | 3-Methylbenzyl | 2-CH₃ | H | SCH₃ | H |
| B.090 | 3-Methylbenzyl | 2-CH₃ | H | SCH₃ | 3-Cl |
| B.091 | 1-(4-Chlorophenyl)-ethyl | 2-CH₃ | H | SCH₃ | H |
| B.092 | 4-(4-Chlorophenyl)-2-butenyl | 2-CH₃ | H | SCH₃ | H |
| B.093 | Methyl | 6-CH₃ | H | SCH₃ | H |
| B.094 | Methyl | 6-CH₃ | H | OCH₃ | 3-Cl |
| B.095 | Methyl | 6-CH₃ | H | OCH₃ | 4-Cl |
| B.096 | Methyl | 6-CH₃ | H | OCH₃ | 6-Cl |
| B.097 | Methyl | 6-CH₃ | H | OCH₃ | 3-OCH₃ |
| B.098 | Methyl | 6-CH₃ | H | OCH₃ | 6-CH₃ |
| B.099 | Ethyl | 6-CH₃ | H | OCH₃ | H |
| B.100 | i-Propyl | 6-CH₃ | H | OCH₃ | H |
| B.101 | 2-Propenyl | 6-CH₃ | H | OCH₃ | H |
| B.102 | 2-Propenyl | 6-CH₃ | H | OCH₃ | 3-Cl |
| B.103 | (E)-3-Chloro-2-propenyl | 6-CH₃ | H | OCH₃ | H |
| B.104 | 2-Propynyl | 6-CH₃ | H | OCH₃ | H |
| B.105 | 2-Propynyl | 6-CH₃ | H | OCH₃ | 3-Cl |
| B.106 | 2-Propynyl | 6-CH₃ | H | OCH₃ | 3-OCH₃ |
| B.107 | 2-Propynyl | 6-CH₃ | H | OCH₃ | 6-CH₃ |
| B.108 | Cyanomethyl | 6-CH₃ | H | OCH₃ | H |
| B.109 | 1-(t-Butoxycarbonyl)-ethyl | 6-CH₃ | H | OCH₃ | H |
| B.110 | Cyclopropylmethyl | 6-CH₃ | H | OCH₃ | H |
| B.111 | Benzyl | 6-CH₃ | H | OCH₃ | H |
| B.112 | 3-Methylbenzyl | 6-CH₃ | H | OCH₃ | H |
| B.113 | 3-Methylbenzyl | 6-CH₃ | H | OCH₃ | 3-Cl |
| B.114 | 1-(4-Chlorophenyl)-ethyl | 6-CH₃ | H | OCH₃ | H |
| B.115 | 4-(4-Chlorophenyl)-2-butenyl | 6-CH₃ | H | OCH₃ | H |
| B.116 | Methyl | 6-CH₃ | H | OC₂H₅ | H |
| B.117 | Methyl | 6-CH₃ | H | OC₂H₅ | 3-Cl |
| B.118 | Methyl | 6-CH₃ | H | OC₂H₅ | 4-Cl |
| B.119 | Methyl | 6-CH₃ | H | OC₂H₅ | 6-Cl |
| B.120 | Methyl | 6-CH₃ | H | OC₂H₅ | 3-OCH₃ |
| B.121 | Methyl | 6-CH₃ | H | OC₂H₅ | 6-CH₃ |
| B.122 | Ethyl | 6-CH₃ | H | OC₂H₅ | H |
| B.123 | i-Propyl | 6-CH₃ | H | OC₂H₅ | H |
| B.124 | 2-Propenyl | 6-CH₃ | H | OC₂H₅ | H |
| B.125 | 2-Propenyl | 6-CH₃ | H | OC₂H₅ | 3-Cl |
| B.126 | (E)-3-Chloro-2-propenyl | 6-CH₃ | H | OC₂H₅ | H |
| B.127 | 2-Propynyl | 6-CH₃ | H | OC₂H₅ | H |
| B.128 | 2-Propynyl | 6-CH₃ | H | OC₂H₅ | 3-Cl |
| B.129 | 2-Propynyl | 6-CH₃ | H | OC₂H₅ | 3-OCH₃ |
| B.130 | 2-Propynyl | 6-CH₃ | H | OC₂H₅ | 6-CH₃ |
| B.131 | Cyanomethyl | 6-CH₃ | H | OC₂H₅ | H |
| B.132 | 1-(tert-Butoxycarbonyl)-ethyl | 6-CH₃ | H | OC₂H₅ | H |
| B.133 | Cyclopropylmethyl | 6-CH₃ | H | OC₂H₅ | H |
| B.134 | Benzyl | 6-CH₃ | H | OC₂H₅ | H |
| B.135 | 3-Methylbenzyl | 6-CH₃ | H | OC₂H₅ | H |
| B.136 | 3-Methylbenzyl | 6-CH₃ | H | OC₂H₅ | 3-Cl |
| B.137 | 1-(4-Chlorophenyl)-ethyl | 6-CH₃ | H | OC₂H₅ | H |
| B.138 | 4-(4-Chlorophenyl)-2-butenyl | 6-CH₃ | H | OC₂H₅ | H |
| B.139 | Methyl | 6-CH₃ | H | SCH₃ | H |
| B.140 | Methyl | 6-CH₃ | H | SCH₃ | 3-Cl |
| B.141 | Methyl | 6-CH₃ | H | SCH₃ | 4-Cl |
| B.142 | Methyl | 6-CH₃ | H | SCH₃ | 6-Cl |
| B.143 | Methyl | 6-CH₃ | H | SCH₃ | 3-OCH₃ |
| B.144 | Methyl | 6-CH₃ | H | SCH₃ | 6-CH₃ |
| B.145 | Ethyl | 6-CH₃ | H | SCH₃ | H |
| B.146 | i-Propyl | 6-CH₃ | H | SCH₃ | H |
| B.147 | 2-Propenyl | 6-CH₃ | H | SCH₃ | H |
| B.148 | 2-Propenyl | 6-CH₃ | H | SCH₃ | 3-Cl |
| B.149 | (E)-3-Chloro-2-propenyl | 6-CH₃ | H | SCH₃ | H |
| B.150 | 2-Propynyl | 6-CH₃ | H | SCH₃ | H |
| B.151 | 2-Propynyl | 6-CH₃ | H | SCH₃ | 3-Cl |
| B.152 | 2-Propynyl | 6-CH₃ | H | SCH₃ | 3-OCH₃ |
| B.153 | 2-Propynyl | 6-CH₃ | H | SCH₃ | 6-CH₃ |
| B.154 | Cyanomethyl | 6-CH₃ | H | SCH₃ | H |
| B.155 | 1-(tert-Butoxycarbonyl)-ethyl | 6-CH₃ | H | SCH₃ | H |
| B.156 | Cyclopropylmethyl | 6-CH₃ | H | SCH₃ | H |
| B.157 | Benzyl | 6-CH₃ | H | SCH₃ | H |
| B.158 | 3-Methylbenzyl | 6-CH₃ | H | SCH₃ | H |
| B.159 | 3-Methylbenzyl | 6-CH₃ | H | SCH₃ | 3-Cl |
| B.160 | 1-(4-Chlorophenyl)-ethyl | 6-CH₃ | H | SCH₃ | H |
| B.161 | 4-(4-Chlorophenyl)-2-butenyl | 6-CH₃ | H | SCH₃ | H |
| B.162 | Methyl | 6-CH₃ | H | Cl | H |
| B.163 | Methyl | 6-CH₃ | H | Cl | 3-Cl |
| B.164 | Methyl | 6-CH₃ | H | Cl | 4-Cl |
| B.165 | Methyl | 6-CH₃ | H | Cl | 6-Cl |
| B.166 | Methyl | 6-CH₃ | H | Cl | 3-OCH₃ |
| B.167 | Methyl | 6-CH₃ | H | Cl | 6-CH₃ |
| B.168 | Ethyl | 6-CH₃ | H | Cl | H |
| B.169 | i-Propyl | 6-CH₃ | H | Cl | H |
| B.170 | 2-Propenyl | 6-CH₃ | H | Cl | H |
| B.171 | 2-Propenyl | 6-CH₃ | H | Cl | 3-Cl |
| B.172 | (E)-3-Chloro-2-propenyl | 6-CH₃ | H | Cl | H |
| B.173 | 2-Propynyl | 6-CH₃ | H | Cl | H |
| B.174 | 2-Propynyl | 6-CH₃ | H | Cl | 3-Cl |

TABLE B-continued

| No. | R¹ | R² | R³ | R⁴ | (R⁵)n |
|---|---|---|---|---|---|
| B.175 | 2-Propynyl | 6-CH₃ | H | Cl | 3-OCH₃ |
| B.176 | 2-Propynyl | 6-CH₃ | H | Cl | 6-CH₃ |
| B.177 | Cyanomethyl | 6-CH₃ | H | Cl | H |
| B.178 | 1-(tert-Butoxycarbonyl)-ethyl | 6-CH₃ | H | Cl | H |
| B.179 | Cyclopropylmethyl | 6-CH₃ | H | Cl | H |
| B.180 | Benzyl | 6-CH₃ | H | Cl | H |
| B.181 | 3-Methylbenzyl | 6-CH₃ | H | Cl | H |
| B.182 | 3-Methylbenzyl | 6-CH₃ | H | Cl | 3-Cl |
| B.183 | 1-(4-Chlorophenyl)-ethyl | 6-CH₃ | H | Cl | H |
| B.184 | 4-(4-Chlorophenyl)-2-butenyl | 6-CH₃ | H | Cl | H |
| B.185 | Methyl | 4-OCH₃ | H | OCH₃ | H |
| B.186 | Methyl | 4-OCH₃ | H | OCH₃ | 3-Cl |
| B.187 | Methyl | 4-OCH₃ | H | OCH₃ | 4-Cl |
| B.188 | Methyl | 4-OCH₃ | H | OCH₃ | 6-Cl |
| B.189 | Methyl | 4-OCH₃ | H | OCH₃ | 3-OCH₃ |
| B.190 | Methyl | 4-OCH₃ | H | OCH₃ | 6-CH₃ |
| B.191 | Ethyl | 4-OCH₃ | H | OCH₃ | H |
| B.192 | i-Propyl | 4-OCH₃ | H | OCH₃ | H |
| B.193 | 2-Propenyl | 4-OCH₃ | H | OCH₃ | H |
| B.194 | 2-Propenyl | 4-OCH₃ | H | OCH₃ | 3-Cl |
| B.195 | (E)-3-Chloro-2-propenyl | 4-OCH₃ | H | OCH₃ | H |
| B.196 | 2-Propynyl | 4-OCH₃ | H | OCH₃ | H |
| B.197 | 2-Propynyl | 4-OCH₃ | H | OCH₃ | 3-Cl |
| B.198 | 2-Propynyl | 4-OCH₃ | H | OCH₃ | 3-OCH₃ |
| B.199 | 2-Propynyl | 4-OCH₃ | H | OCH₃ | 6-CH₃ |
| B.200 | Cyanomethyl | 4-OCH₃ | H | OCH₃ | H |
| B.201 | 1-(tert-Butoxycarbonyl)-ethyl | 4-OCH₃ | H | OCH₃ | H |
| B.202 | Cyclopropylmethyl | 4-OCH₃ | H | OCH₃ | H |
| B.203 | Benzyl | 4-OCH₃ | H | OCH₃ | H |
| B.204 | 3-Methylbenzyl | 4-OCH₃ | H | OCH₃ | H |
| B.205 | 3-Methylbenzyl | 4-OCH₃ | H | OCH₃ | 3-Cl |
| B.206 | 1-(4-Chlorophenyl)-ethyl | 4-OCH₃ | H | OCH₃ | H |
| B.207 | 4-(4-Chlorophenyl)-2-butenyl | 4-OCH₃ | H | OCH₃ | H |
| B.208 | Methyl | 4-OCH₃ | H | Cl | H |
| B.209 | Methyl | 4-OCH₃ | H | Cl | 3-Cl |
| B.210 | Methyl | 4-OCH₃ | H | Cl | 4-Cl |
| B.211 | Methyl | 4-OCH₃ | H | Cl | 6-Cl |
| B.212 | Methyl | 4-OCH₃ | H | Cl | 3-OCH₃ |
| B.213 | Methyl | 4-OCH₃ | H | Cl | 6-CH₃ |
| B.214 | Ethyl | 4-OCH₃ | H | Cl | H |
| B.215 | i-Propyl | 4-OCH₃ | H | Cl | H |
| B.216 | 2-Propenyl | 4-OCH₃ | H | Cl | H |
| B.217 | 2-Propenyl | 4-OCH₃ | H | Cl | 3-Cl |
| B.218 | (E)-3-Chloro-2-propenyl | 4-OCH₃ | H | Cl | H |
| B.219 | 2-Propynyl | 4-OCH₃ | H | Cl | H |
| B.220 | 2-Propynyl | 4-OCH₃ | H | Cl | 3-Cl |
| B.221 | 2-Propynyl | 4-OCH₃ | H | Cl | 3-OCH₃ |
| B.222 | 2-Propynyl | 4-OCH₃ | H | Cl | 6-CH₃ |
| B.223 | Cyanomethyl | 4-OCH₃ | H | Cl | H |
| B.224 | 1-(tert-Butoxycarbonyl)-ethyl | 4-OCH₃ | H | Cl | H |
| B.225 | Cyclopropylmethyl | 4-OCH₃ | H | Cl | H |
| B.226 | Benzyl | 4-OCH₃ | H | Cl | H |
| B.227 | 3-Methylbenzyl | 4-OCH₃ | H | Cl | H |
| B.228 | 3-Methylbenzyl | 4-OCH₃ | H | Cl | 3-Cl |
| B.229 | 1-(4-Chlorophenyl)-ethyl | 4-OCH₃ | H | Cl | H |
| B.230 | 4-(4-Chlorophenyl)-2-butenyl | 4-OCH₃ | H | Cl | H |
| B.231 | Methyl | 6-Cl | H | OCH₃ | H |
| B.232 | Methyl | 6-Cl | H | OCH₃ | 3-Cl |
| B.233 | Methyl | 6-Cl | H | OCH₃ | 4-Cl |
| B.234 | Methyl | 6-Cl | H | OCH₃ | 6-Cl |
| B.235 | Methyl | 6-Cl | H | OCH₃ | 3-OCH₃ |
| B.236 | Methyl | 6-Cl | H | OCH₃ | 6-CH₃ |
| B.237 | Ethyl | 6-Cl | H | OCH₃ | H |
| B.238 | i-Propyl | 6-Cl | H | OCH₃ | H |
| B.239 | 2-Propenyl | 6-Cl | H | OCH₃ | H |
| B.240 | 2-Propenyl | 6-Cl | H | OCH₃ | 3-Cl |
| B.241 | (E)-3-Chloro-2-propenyl | 6-Cl | H | OCH₃ | H |
| B.242 | 2-Propynyl | 6-Cl | H | OCH₃ | H |
| B.243 | 2-Propynyl | 6-Cl | H | OCH₃ | 3-Cl |
| B.244 | 2-Propynyl | 6-Cl | H | OCH₃ | 3-OCH₃ |
| B.245 | 2-Propynyl | 6-Cl | H | OCH₃ | 6-CH₃ |
| B.246 | Cyanomethyl | 6-Cl | H | OCH₃ | H |
| B.247 | 1-(tert-Butoxycarbonyl)-ethyl | 6-Cl | H | OCH₃ | H |
| B.248 | Cyclopropylmethyl | 6-Cl | H | OCH₃ | H |
| B.249 | Benzyl | 6-Cl | H | OCH₃ | H |
| B.250 | 3-Methylbenzyl | 6-Cl | H | OCH₃ | H |
| B.251 | 3-Methylbenzyl | 6-Cl | H | OCH₃ | 3-Cl |
| B.252 | 1-(4-Chlorophenyl)-ethyl | 6-Cl | H | OCH₃ | H |
| B.253 | 4-(4-Chlorophenyl)-2-butenyl | 6-Cl | H | OCH₃ | H |
| B.254 | Methyl | 6-Cl | H | OC₂H₅ | H |
| B.255 | Methyl | 6-Cl | H | OC₂H₅ | 3-Cl |
| B.256 | Methyl | 6-Cl | H | OC₂H₅ | 4-Cl |
| B.257 | Methyl | 6-Cl | H | OC₂H₅ | 6-Cl |
| B.258 | Methyl | 6-Cl | H | OC₂H₅ | 3-OCH₃ |
| B.259 | Methyl | 6-Cl | H | OC₂H₅ | 6-CH₃ |
| B.260 | Ethyl | 6-Cl | H | OC₂H₅ | H |
| B.261 | i-Propyl | 6-Cl | H | OC₂H₅ | H |
| B.262 | 2-Propenyl | 6-Cl | H | OC₂H₅ | H |
| B.263 | 2-Propenyl | 6-Cl | H | OC₂H₅ | 3-Cl |
| B.264 | (E)-3-Chloro-2-propenyl | 6-Cl | H | OC₂H₅ | H |

TABLE B-continued

| No. | R¹ | R² | R³ | R⁴ | (R⁵)n |
|---|---|---|---|---|---|
| B.265 | 2-Propynyl | 6-Cl | H | OC₂H₅ | H |
| B.266 | 2-Propynyl | 6-Cl | H | OC₂H₅ | 3-Cl |
| B.267 | 2-Propynyl | 6-Cl | H | OC₂H₅ | 3-OMe |
| B.268 | 2-Propynyl | 6-Cl | H | OC₂H₅ | 6-CH₃ |
| B.269 | Cyanomethyl | 6-Cl | H | OC₂H₅ | H |
| B.270 | 1-(tert-Butoxycarbonyl)-ethyl | 6-Cl | H | OC₂H₅ | H |
| B.271 | Cyclopropylmethyl | 6-Cl | H | OC₂H₅ | H |
| B.272 | Benzyl | 6-Cl | H | OC₂H₅ | H |
| B.273 | 3-Methylbenzyl | 6-Cl | H | OC₂H₅ | H |
| B.274 | 3-Methylbenzyl | 6-Cl | H | OC₂H₅ | 3-Cl |
| B.275 | 1-(4-Chlorophenyl)-ethyl | 6-Cl | H | OC₂H₅ | H |
| B.276 | 4-(4-Chlorophenyl)-2-butenyl | 6-Cl | H | OC₂H₅ | H |
| B.277 | Methyl | 6-Cl | H | SCH₃ | H |
| B.278 | Methyl | 6-Cl | H | SCH₃ | 3-Cl |
| B.279 | Methyl | 6-Cl | H | SCH₃ | 4-Cl |
| B.280 | Methyl | 6-Cl | H | SCH₃ | 6-Cl |
| B.281 | Methyl | 6-Cl | H | SCH₃ | 3-OCH₃ |
| B.282 | Methyl | 6-Cl | H | SCH₃ | 6-CH₃ |
| B.283 | Ethyl | 6-Cl | H | SCH₃ | H |
| B.284 | i-Propyl | 6-Cl | H | SCH₃ | H |
| B.285 | 2-Propenyl | 6-Cl | H | SCH₃ | H |
| B.286 | 2-Propenyl | 6-Cl | H | SCH₃ | 3-Cl |
| B.287 | (E)-3-Chloro-2-propenyl | 6-Cl | H | SCH₃ | H |
| B.288 | 2-Propynyl | 6-Cl | H | SCH₃ | H |
| B.289 | 2-Propynyl | 6-Cl | H | SCH₃ | 3-Cl |
| B.290 | 2-Propynyl | 6-Cl | H | SCH₃ | 3-OCH₃ |
| B.291 | 2-Propynyl | 6-Cl | H | SCH₃ | 6-CH₃ |
| B.292 | Cyanomethyl | 6-Cl | H | SCH₃ | H |
| B.293 | 1-(tert-Butoxycarbonyl)-ethyl | 6-Cl | H | SCH₃ | H |
| B.294 | Cyclopropylmethyl | 6-Cl | H | SCH₃ | H |
| B.295 | Benzyl | 6-Cl | H | SCH₃ | H |
| B.296 | 3-Methylbenzyl | 6-Cl | H | SCH₃ | H |
| B.297 | 3-Methylbenzyl | 6-Cl | H | SCH₃ | 3-Cl |
| B.298 | 1-(4-Chlorophenyl)-ethyl | 6-Cl | H | SCH₃ | H |
| B.299 | 4-(4-Chlorophenyl)-2-butenyl | 6-Cl | H | SCH₃ | H |
| B.300 | Methyl | 6-Cl | H | Cl | H |
| B.301 | Methyl | 6-Cl | H | Cl | 3-Cl |
| B.302 | Methyl | 6-Cl | H | Cl | 4-Cl |
| B.303 | Methyl | 6-Cl | H | Cl | 6-Cl |
| B.304 | Methyl | 6-Cl | H | Cl | 3-OCH₃ |
| B.305 | Methyl | 6-Cl | H | Cl | 6-CH₃ |
| B.306 | Ethyl | 6-Cl | H | Cl | H |
| B.307 | i-Propyl | 6-Cl | H | Cl | H |
| B.308 | 2-Propenyl | 6-Cl | H | Cl | H |
| B.309 | 2-Propenyl | 6-Cl | H | Cl | 3-Cl |
| B.310 | (E)-3-Chloro-2-propenyl | 6-Cl | H | Cl | H |
| B.311 | 2-Propynyl | 6-Cl | H | Cl | H |
| B.312 | 2-Propynyl | 6-Cl | H | Cl | 3-Cl |
| B.313 | 2-Propynyl | 6-Cl | H | Cl | 3-OCH₃ |
| B.314 | 2-Propynyl | 6-Cl | H | Cl | 6-CH₃ |
| B.315 | Cyanomethyl | 6-Cl | H | Cl | H |
| B.316 | 1-(tert-Butoxycarbonyl)-ethyl | 6-Cl | H | Cl | H |
| B.317 | Cyclopropylmethyl | 6-Cl | H | Cl | H |
| B.318 | Benzyl | 6-Cl | H | Cl | H |
| B.319 | 3-Methylbenzyl | 6-Cl | H | Cl | H |
| B.320 | 3-Methylbenzyl | 6-Cl | H | Cl | 3-Cl |
| B.321 | 1-(4-Chlorophenyl)-ethyl | 6-Cl | H | Cl | H |
| B.322 | 4-(4-Chlorophenyl)-2-butenyl | 6-Cl | H | Cl | H |
| B.323 | Methyl | 6-CH₃ | 4-CH₃ | OCH₃ | H |
| B.324 | Methyl | 6-CH₃ | 4-CH₃ | OCH₃ | 3-Cl |
| B.325 | Methyl | 6-CH₃ | 4-CH₃ | OCH₃ | 4-Cl |
| B.326 | Methyl | 6-CH₃ | 4-CH₃ | OCH₃ | 6-Cl |
| B.327 | Methyl | 6-CH₃ | 4-CH₃ | OCH₃ | 3-OCH₃ |
| B.328 | Methyl | 6-CH₃ | 4-CH₃ | OCH₃ | 6-CH₃ |
| B.329 | Ethyl | 6-CH₃ | 4-CH₃ | OCH₃ | H |
| B.330 | i-Propyl | 6-CH₃ | 4-CH₃ | OCH₃ | u |
| B.331 | 2-Propenyl | 6-CH₃ | 4-CH₃ | OCH₃ | H |
| B.332 | 2-Propenyl | 6-CH₃ | 4-CH₃ | OCH₃ | 3-Cl |
| B.333 | (E)-3-Chloro-2-propenyl | 6-CH₃ | 4-CH₃ | OCH₃ | H |
| B.334 | 2-Propynyl | 6-CH₃ | 4-CH₃ | OCH₃ | H |
| B.335 | 2-Propynyl | 6-CH₃ | 4-CH₃ | OCH₃ | 3-Cl |
| B.336 | 2-Propynyl | 6-CH₃ | 4-CH₃ | OCH₃ | 3-OCH₃ |
| B.337 | 2-Propynyl | 6-CH₃ | 4-CH₃ | OCH₃ | 6-CH₃ |
| B.338 | Cyanomethyl | 6-CH₃ | 4-CH₃ | OCH₃ | H |
| B.339 | 1-(tert-Butoxycarbonyl)-ethyl | 6-CH₃ | 4-CH₃ | OCH₃ | H |
| B.340 | Cyclopropylmethyl | 6-CH₃ | 4-CH₃ | OCH₃ | H |
| B.341 | Benzyl | 6-CH₃ | 4-CH₃ | OCH₃ | H |
| B.342 | 3-Methylbenzyl | 6-CH₃ | 4-CH₃ | OCH₃ | H |
| B.343 | 3-Methylbenzyl | 6-CH₃ | 4-CH₃ | OCH₃ | 3-Cl |
| B.344 | 1-(4-Chlorophenyl)-ethyl | 6-CH₃ | 4-CH₃ | OCH₃ | H |
| B.345 | 4-(4-Chlorophenyl)-2-butenyl | 6-CH₃ | 4-CH₃ | OCH₃ | H |
| B.346 | Methyl | 6-CH₃ | 4-CH₃ | Cl | H |
| B.347 | Methyl | 6-CH₃ | 4-CH₃ | Cl | 3-Cl |
| B.348 | Methyl | 6-CH₃ | 4-CH₃ | Cl | 4-Cl |
| B.349 | Methyl | 6-CH₃ | 4-CH₃ | Cl | 6-Cl |
| B.350 | Methyl | 6-CH₃ | 4-CH₃ | Cl | 3-OCH₃ |
| B.351 | Methyl | 6-CH₃ | 4-CH₃ | Cl | 6-CH₃ |
| B.352 | Ethyl | 6-CH₃ | 4-CH₃ | Cl | H |
| B.353 | i-Propyl | 6-CH₃ | 4-CH₃ | Cl | H |
| B.354 | 2-Propenyl | 6-CH₃ | 4-CH₃ | Cl | H |
| B.355 | 2-Propenyl | 6-CH₃ | 4-CH₃ | Cl | 3-Cl |
| B.356 | (E)-3- | 6-CH₃ | 4-CH₃ | Cl | H |

TABLE B-continued

| No. | R¹ | R² | R³ | R⁴ | (R⁵)n |
|---|---|---|---|---|---|
| B.357 | Chloro-2-propenyl 2-Propynyl | 6-CH₃ | 4-CH₃ | Cl | H |
| B.358 | 2-Propynyl | 6-CH₃ | 4-CH₃ | Cl | 3-Cl |
| B.359 | 2-Propynyl | 6-CH₃ | 4-CH₃ | Cl | 3-OCH₃ |
| B.360 | 2-Propynyl | 6-CH₃ | 4-CH₃ | Cl | 6-CH₃ |
| B.361 | Cyano-methyl | 6-CH₃ | 4-CH₃ | Cl | H |
| B.362 | 1-(tert-Butoxy-carbonyl)-ethyl | 6-CH₃ | 4-CH₃ | Cl | H |
| B.363 | Cyclo-propyl-methyl | 6-CH₃ | 4-CH₃ | Cl | H |
| B.364 | Benzyl | 6-CH₃ | 4-CH₃ | Cl | H |
| B.365 | 3-Methyl-benzyl | 6-CH₃ | 4-CH₃ | Cl | H |
| B.366 | 3-Methyl-benzyl | 6-CH₃ | 4-CH₃ | Cl | 3-Cl |
| B.367 | 1-(4-Chloro-phenyl)-ethyl | 6-CH₃ | 4-CH₃ | Cl | H |
| B.368 | 4-(4-Chloro-phenyl)-2-butenyl | 6-CH₃ | 4-CH₃ | Cl | H |
| B.369 | Methyl | 2-F | H | OCH₃ | H |
| B.370 | Methyl | 2-F | H | OCH₃ | 3-Cl |
| B.371 | Methyl | 2-F | H | OCH₃ | 4-Cl |
| B.372 | Methyl | 2-F | H | OCH₃ | 6-Cl |
| B.373 | Methyl | 2-F | H | OCH₃ | 3-OCH₃ |
| B.374 | Methyl | 2-F | H | OCH₃ | 6-CH₃ |
| B.375 | Ethyl | 2-F | H | OCH₃ | H |
| B.376 | i-Propyl | 2-F | H | OCH₃ | H |
| B.377 | 2-Propenyl | 2-F | H | OCH₃ | H |
| B.378 | 2-Propenyl | 2-F | H | OCH₃ | 3-Cl |
| B.379 | (E)-3-Chloro-2-propenyl | 2-F | H | OCH₃ | H |
| B.380 | 2-Propynyl | 2-F | H | OCH₃ | H |
| B.381 | 2-Propynyl | 2-F | H | OCH₃ | 3-Cl |
| B.382 | 2-Propynyl | 2-F | H | OCH₃ | 3-OCH₃ |
| B.383 | 2-Propynyl | 2-F | H | OCH₃ | 6-CH₃ |
| B.384 | Cyano-methyl | 2-F | H | OCH₃ | H |
| B.385 | 1-(tert-Butoxy-carbonyl)-ethyl | 2-F | H | OCH₃ | H |
| B.386 | Cyclo-propyl-methyl | 2-F | H | OCH₃ | H |
| B.387 | Benzyl | 2-F | H | OCH₃ | H |
| B.388 | 3-Methyl-benzyl | 2-F | H | OCH₃ | H |
| B.389 | 3-Methyl-benzyl | 2-F | H | OCH₃ | 3-Cl |
| B.390 | 1-(4-Chloro-phenyl)-ethyl | 2-F | H | OCH₃ | H |
| B.391 | 4-(4-Chloro-phenyl)-2-butenyl | 2-F | H | OCH₃ | H |
| B.392 | Methyl | 2-F | H | Cl | H |
| B.393 | Methyl | 2-F | H | Cl | 3-Cl |
| B.394 | Methyl | 2-F | H | Cl | 4-Cl |
| B.395 | Methyl | 2-F | H | Cl | 6-Cl |
| B.396 | Methyl | 2-F | H | Cl | 3-OCH₃ |
| B.397 | Methyl | 2-F | H | Cl | 6-CH₃ |
| B.398 | Ethyl | 2-F | H | Cl | H |
| B.399 | i-Propyl | 2-F | H | Cl | H |
| B.400 | 2-Propenyl | 2-F | H | Cl | H |
| B.401 | 2-Propenyl | 2-F | H | Cl | 3-Cl |
| B.402 | (E)-3-Chloro-2-propenyl | 2-F | H | Cl | H |
| B.403 | 2-Propynyl | 2-F | H | Cl | H |
| B.404 | 2-Propynyl | 2-F | H | Cl | 3-Cl |
| B.405 | 2-Propynyl | 2-F | H | Cl | 3-OCH₃ |
| B.406 | 2-Propynyl | 2-F | H | Cl | 6-CH₃ |
| B.407 | Cyano-methyl | 2-F | H | Cl | H |
| B.408 | 1-(tert-Butoxy-carbonyl)-ethyl | 2-F | H | Cl | H |
| B.409 | Cyclo-propyl-methyl | 2-F | H | Cl | H |
| B.410 | Benzyl | 2-F | H | Cl | H |
| B.411 | 3-Methyl-benzyl | 2-F | H | Cl | H |
| B.412 | 3-Methyl-benzyl | 2-F | H | Cl | 3-Cl |
| B.413 | 1-(4-Chloro-phenyl)-ethyl | 2-F | H | Cl | H |
| B.414 | 4-(4-Chloro-phenyl)-2-butenyl | 2-F | H | Cl | H |
| B.415 | Methyl | 6-CN | H | OCH₃ | H |
| B.416 | Methyl | 6-CN | H | OCH₃ | 3-Cl |
| B.417 | Methyl | 6-CN | H | OCH₃ | 4-Cl |
| B.418 | Methyl | 6-CN | H | OCH₃ | 6-Cl |
| B.419 | Methyl | 6-CN | H | OCH₃ | 3-OCH₃ |
| B.420 | Methyl | 6-CN | H | OCH₃ | 6-CH₃ |
| B.421 | Ethyl | 6-CN | H | OCH₃ | H |
| B.422 | i-Propyl | 6-CN | H | OCH₃ | H |
| B.423 | 2-Propenyl | 6-CN | H | OCH₃ | H |
| B.424 | 2-Propenyl | 6-CN | H | OCH₃ | 3-Cl |
| B.425 | (E)-3-Chloro-2-propenyl | 6-CN | H | OCH₃ | H |
| B.426 | 2-Propynyl | 6-CN | H | OCH₃ | H |
| B.427 | 2-Propynyl | 6-CN | H | OCH₃ | 3-Cl |
| B.428 | 2-Propynyl | 6-CN | H | OCH₃ | 3-OCH₃ |
| B.429 | 2-Propynyl | 6-CN | H | OCH₃ | 6-CH₃ |
| B.430 | Cyano-methyl | 6-CN | H | OCH₃ | H |
| B.431 | 1-(tert-Butoxy-carbonyl)-ethyl | 6-CN | H | OCH₃ | H |
| B.432 | Cyclo-propyl-methyl | 6-CN | H | OCH₃ | H |
| B.433 | Benzyl | 6-CN | H | OCH₃ | H |
| B.434 | 3-Methyl-benzyl | 6-CN | H | OCH₃ | H |
| B.435 | 3-Methyl-benzyl | 6-CN | H | OCH₃ | 3-Cl |
| B.436 | 1-(4-Chloro-phenyl)-ethyl | 6-CN | H | OCH₃ | H |
| B.437 | 4-(4-Chloro-phenyl)-2-butenyl | 6-CN | H | OCH₃ | H |
| B.438 | Methyl | 6-CN | H | Cl | H |
| B.439 | Methyl | 6-CN | H | Cl | 3-Cl |
| B.440 | Methyl | 6-CN | H | Cl | 4-Cl |
| B.441 | Methyl | 6-CN | H | Cl | 6-Cl |
| B.442 | Methyl | 6-CN | H | Cl | 3-OCH₃ |
| B.443 | Methyl | 6-CN | H | Cl | 6-CH₃ |
| B.444 | Ethyl | 6-CN | H | Cl | H |
| B.445 | i-Propyl | 6-CN | H | Cl | H |
| B.446 | 2-Propenyl | 6-CN | H | Cl | H |

TABLE B-continued

| No. | R¹ | R² | R³ | R⁴ | (R⁵)n |
|---|---|---|---|---|---|
| B.447 | 2-Propenyl | 6-CN | H | Cl | 3-Cl |
| B.448 | (E)-3-Chloro-2-propenyl | 6-CN | H | Cl | H |
| B.449 | 2-Propynyl | 6-CN | H | Cl | H |
| B.450 | 2-Propynyl | 6-CN | H | Cl | 3-Cl |
| B.451 | 2-propynyl | 6-CN | H | Cl | 3-OCH₃ |
| B.452 | 2-Propynyl | 6-CN | H | Cl | 6-CH₃ |
| B.453 | Cyanomethyl | 6-CN | H | Cl | H |
| B.454 | 1-(tert-Butoxycarbonyl)-ethyl | 6-CN | H | Cl | H |
| B.455 | Cyclopropylmethyl | 6-CN | H | Cl | H |
| B.456 | Benzyl | 6-CN | H | Cl | H |
| B.457 | 3-Methylbenzyl | 6-CN | H | Cl | H |
| B.458 | 3-Methylbenzyl | 6-CN | H | Cl | 3-Cl |
| B.459 | 1-(4-Chlorophenyl)-ethyl | 6-CN | H | Cl | H |
| B.460 | 4-(4-Chlorophenyl)-2-butenyl | 6-CN | H | Cl | H |
| B.461 | Methyl | 2-CH₃ | H | Br | H |
| B.462 | Methyl | 2-CH₃ | H | CN | H |
| B.463 | Methyl | 2-CH₃ | H | SC₆H₅ | H |
| B.464 | Methyl | 2-CH₃ | H | OC₆H₅ | H |
| B.465 | Methyl | 6-CH₃ | H | Br | H |
| B.466 | Methyl | 6-CH₃ | H | CN | H |
| B.467 | Methyl | 6-CH₃ | H | SC₆H₅ | H |
| B.468 | Methyl | 6-CH₃ | H | OC₆H₅ | H |
| B.469 | Methyl | 4-CH₃ | H | Br | H |
| B.470 | Methyl | 4-CH₃ | H | CN | H |
| B.471 | Methyl | 4-CH₃ | H | SC₆H₅ | H |
| B.472 | Methyl | 4-CH₃ | H | OC₆H₅ | H |
| B.473 | Methyl | 6-Cl | H | Br | H |
| B.474 | Methyl | 6-Cl | H | CN | H |
| B.475 | Methyl | 6-Cl | H | SC₆H₅ | H |
| B.476 | Methyl | 6-Cl | H | OC₆H₅ | H |
| B.477 | Methyl | 6-CH₃ | 4-CH₃ | Br | H |
| B.478 | Methyl | 6-CH₃ | 4-CH₃ | CN | H |
| B.479 | Methyl | 6-CH₃ | 4-CH₃ | SC₆H₅ | H |
| B.480 | Methyl | 6-CH₃ | 4-CH₃ | OC₆H₅ | H |
| B.481 | Methyl | 2-F | H | Br | H |
| B.482 | Methyl | 2-F | H | CN | H |
| B.483 | Methyl | 2-F | H | SC₆H₅ | H |
| B.484 | Methyl | 2-F | H | OC₆H₅ | H |
| B.485 | Methyl | 6-CN | H | Br | H |
| B.486 | Methyl | 6-CN | H | CN | H |
| B.487 | Methyl | 6-CN | H | SC₆H₅ | H |
| B.488 | Methyl | 6-CN | H | SC₆H₅ | H |
| B.489 | Ethyl | 2-CH₃ | H | Br | H |
| B.490 | Ethyl | 2-CH₃ | H | CN | H |
| B.491 | Ethyl | 2-CH₃ | H | SC₆H₅ | H |
| B.492 | Ethyl | 2-CH₃ | H | OC₆H₅ | H |
| B.493 | Ethyl | 6-CH₃ | H | Br | H |
| B.494 | Ethyl | 6-CH₃ | H | CN | H |
| B.495 | Ethyl | 6-CH₃ | H | SC₆H₅ | H |
| B.496 | Ethyl | 6-CH₃ | H | OC₆H₅ | H |
| B.497 | Ethyl | 4-CH₃ | H | Br | H |
| B.498 | Ethyl | 4-CH₃ | H | CN | H |
| B.499 | Ethyl | 4-CH₃ | H | SC₆H₅ | H |
| B.500 | Ethyl | 4-CH₃ | H | OC₆H₅ | H |
| B.501 | Ethyl | 6-Cl | H | Br | H |
| B.502 | Ethyl | 6-Cl | H | CN | H |
| B.503 | Ethyl | 6-Cl | H | SC₆H₅ | H |
| B.504 | Ethyl | 6-Cl | H | OC₆H₅ | H |
| B.505 | Ethyl | 6-CH₃ | 4-CH₃ | Br | H |
| B.506 | Ethyl | 6-CH₃ | 4-CH₃ | CN | H |
| B.507 | Ethyl | 6-CH₃ | 4-CH₃ | SC₆H₅ | H |
| B.508 | Ethyl | 6-CH₃ | 4-CH₃ | OC₆H₅ | H |
| B.509 | Ethyl | 2-F | H | Br | H |
| B.510 | Ethyl | 2-F | H | CN | H |
| B.511 | Ethyl | 2-F | H | SC₆H₅ | H |
| B.512 | Ethyl | 2-F | H | OC₆H₅ | H |
| B.513 | Ethyl | 6-CN | H | Br | H |
| B.514 | Ethyl | 6-CN | H | CN | H |
| B.515 | Ethyl | 6-CN | H | SC₆H₅ | H |
| B.516 | Ethyl | 6-CN | H | OC₆H₅ | H |
| B.517 | 2-Propenyl | 2-CH₃ | H | Br | H |
| B.518 | 2-Propenyl | 2-CH₃ | H | CN | H |
| B.519 | 2-Propenyl | 2-CH₃ | H | SC₆H₅ | H |
| B.520 | 2-Propenyl | 2-CH₃ | H | OC₆H₅ | H |
| B.521 | 2-Propenyl | 6-CH₃ | H | Br | H |
| B.522 | 2-Propenyl | 6-CH₃ | H | CN | H |
| B.523 | 2-Propenyl | 6-CH₃ | H | SC₆H₅ | H |
| B.524 | 2-Propenyl | 6-CH₃ | H | OC₆H₅ | H |
| B.525 | 2-Propenyl | 4-CH₃ | H | Br | H |
| B.526 | 2-Propenyl | 4-CH₃ | H | CN | H |
| B.527 | 2-Propenyl | 4-CH₃ | H | SC₆H₅ | H |
| B.528 | 2-Propenyl | 4-CH₃ | H | OC₆H₅ | H |
| B.529 | 2-Propenyl | 6-Cl | H | Br | H |
| B.530 | 2-Propenyl | 6-Cl | H | CN | H |
| B.531 | 2-Propenyl | 6-Cl | H | SC₆H₅ | H |
| B.532 | 2-Propenyl | 6-Cl | H | OC₆H₅ | H |
| B.533 | 2-Propenyl | 6-CH₃ | 4-CH₃ | Br | H |
| B.534 | 2-Propenyl | 6-CH₃ | 4-CH₃ | CN | H |
| B.535 | 2-Propenyl | 6-CH₃ | 4-CH₃ | SC₆H₅ | H |
| B.536 | 2-Propenyl | 6-CH₃ | 4-CH₃ | OC₆H₅ | H |
| B.537 | 2-Propenyl | 2-F | H | Br | H |
| B.538 | 2-Propenyl | 2-F | H | CN | H |
| B.539 | 2-Propenyl | 2-F | H | SC₆H₅ | H |
| B.540 | 2-Propenyl | 2-F | H | OC₆H₅ | H |
| B.541 | 2-Propenyl | 6-CN | H | Br | H |
| B.542 | 2-Propenyl | 6-CN | H | CN | H |
| B.543 | 2-Propenyl | 6-CN | H | SC₆H₅ | H |
| B.544 | 2-Propenyl | 6-CN | H | OC₆H₅ | H |

The novel substituted benzoxyphenyl derivatives I are obtainable in various ways, to be specific preferably by one of the following processes:

A) Reaction of a phenol II or its alkali metal, alkaline earth metal, silver or ammonium salt with phenyl compounds III to give substituted phenoxymethylphenyl derivatives I, Y being oxygen:

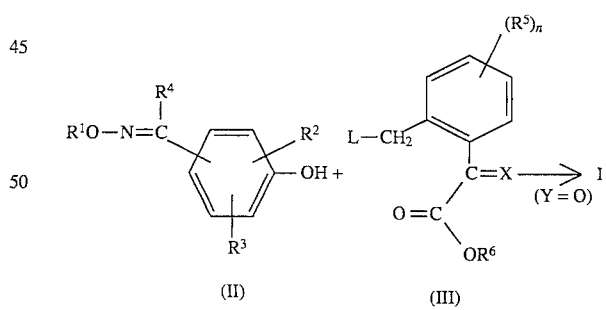

L is a customary leaving group such as chlorine, bromine, iodine, mesylate, trifluoromethylsulfonate or toluenesulfonate.

The reaction is customarily carried out in an inert solvent or diluent, eg. in acetone, dimethylformamide or toluene, or in a two-phase system of water and eg. dichloromethane using a phase-transfer catalyst.

Suitable phase-transfer catalysts are eg. ammonium, sulfonium or phosphonium salts, the type of anion being of secondary importance. Examples which have proven expedient are benzyltrimethylammonium salts such as benzyltrimethylammonium hydroxide and tetrabutylammonium salts.

The reaction is normally carried out at a reaction temperature of from 0° to 100° C., in particular from 20° to 60° C.

The starting materials II and III are normally reacted with one another in approximately equimolar amounts. With respect to the yield, however, it may be advantageous to employ III in an excess of from approximately 1 to 20 mol %, preferably from 1 to 10 mol %, based on II.

In general, a catalytic amount of phase-transfer catalyst, approximately from 1 to 10 mol %, based on II or III is adequate.

The phenyl compounds III in which X is =CH—OCH$_3$ or =N—OCH$_3$ are disclosed in EP-A 386 561 and the phenyl compounds III in which X is =CH—CH$_3$ are disclosed in EP-A 513 580. Both European applications also disclose processes by which the benzoxyphenyl derivatives I where Y=oxygen can be prepared.

Starting from the benzoxyphenyl derivatives I where Y=oxygen and R$^6$=C$_1$–C$_4$-alkyl, the corresponding compounds I where R$^6$=hydrogen can be prepared by processes of ester cleavage known per se (cf. eg. Houben-Weyl, Methoden der Organischen Chemie (Methods of Organic Chemistry), vol. E 5, pp. 223–254; Org. Reactions 24, (1976), pp. 187–224).

B) Alkylation of hydroximic acid (thio)esters IVa or of hydroxamic acid esters IVb

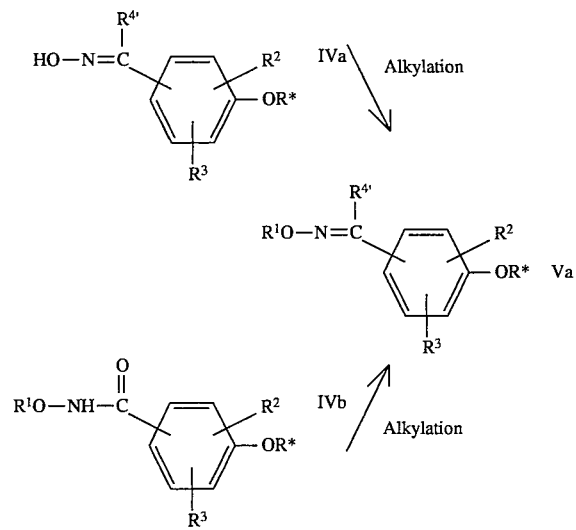

R$^{4'}$ is alkoxy;

R* is hydrogen, a phenol protective group such as methoxymethyl, allyl, phenacyl, acetyl, tert-butyl or benzyl or the radical:

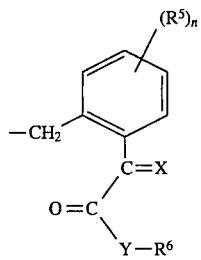

Alkylation is carried out in a manner known per se. With respect to the alkylation of the hydroximic acid (thio)ester IVa, reference may be made, for example, to Houben-Weyl, Methoden der Organischen Chemie (Methods of Organic Chemistry), volume 10/1, p. 1190; J. Org. Chem. 46 (1981), pp. 3623–3629.

Suitable alkylating agents are in particular alkyl halides, alkylsulfonates, dialkyl sulfates or Meerwein salts (cf. for this eg. J. Org. Chem. 36 (1971), pp. 284–294), alkyl triflates (cf. eg. J. Org. Chem. 54 (1989), p. 1736ff) and also diazomethane (cf. eg. Austr. J. Chem. 27 (1974), pp. 1341–1349).

The reaction is customarily carried out at from 0° to 60° C., preferably from 0° to 20° C.

Suitable solvents are, for example, ethers such as diethyl ether, dioxane, ketones such as acetone, methyl ethyl ketone, alcohols such as methanol, ethanol, and also acetonitrile, dimethyl sulfoxide, dimethylformamide and N-methylpyrrolidinone. Acetone, dimethyl sulfoxide and dimethylformamide are particularly preferred.

Compounds Va in which R* is a phenol protective group can be converted into compounds Va where R*=hydrogen by removal of the protective group (cf. eg. Th. W. Green "Protective Groups in Organic Synthesis", Wiley+Sons, pp. 87–108).

The compounds Va where R*=hydrogen can be reacted with phenyl compounds III in a similar manner to method A) to give the substituted benzoxyphenyl derivatives I where Y=oxygen.

C) Halogenation of hydroxamic acid esters IVb to hydroximic acid ester chlorides or bromides Vb and subsequent nucleophilic substitution of the halogen (cf. for this eg. J. Org. Chem. 50 (1985), pp. 3348–3355) to give compounds Vc:

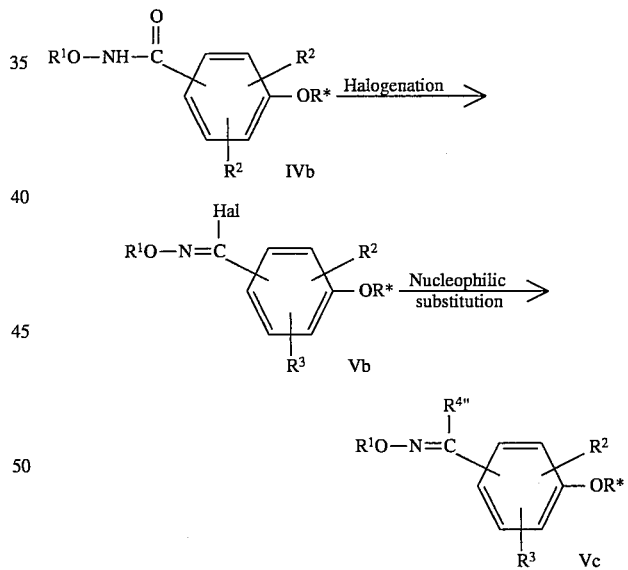

Hal is chlorine or bromine and R$^{4'''}$ is R$^4$, excluding chlorine and bromine.

Suitable halogenating agents are, for example, elemental chlorine or bromine, hypohalites, thionyl chloride, sulfuryl chloride, N-chlorosuccinimide, phosphorus tribromide, phosphorus pentachloride, triphenylphosphine in tetrachloromethane or triphenylphosphine in tetrabromomethane (cf. eg. EP-A 158 153; Houben-Weyl, Methoden der Organischen Chemie (Methods of Organic Chemistry), Vol. VIII, p. 691; Synth. Commun. 16 (1986), 763–765; Gazz. Chim. Ital. 114 (1984), pp. 131–132).

The halogenation is carried out in an inert solvent or diluent such as tetrachloromethane, benzene, diethyl ether, dimethylformamide, dioxane or dioxane/water.

The optimum reaction temperature depends on the halogenating agent. In most cases, a temperature of from approximately 10° to 30° C., in particular from 0° to 10° C., is adequate. Higher temperatures, approximately of from 20° to 80° C., in particular from 40° to 80° C., have proven advantageous in halogenation with triphenylphosphine in tetrachloromethane or tetrabromomethane.

The amount of halogenating agent is not particularly critical. In general, from 0.8 to 2.0, preferably from 0.95 to 1.2, mol of halogenating agent per mole of IVb are adequate.

Suitable nucleophiles are in particular alkoxides (cf. for this eg. EP-A 158 153), alkylamines (cf. eg. J. Org. Chem. 45 (1980), p. 4198 ff und Heterocycles 26 (1987), p. 188) thiophenols and alkylmercaptides (cf. eg. EP-A 426 460).

Suitable solvents for the nucleophilic substitution are the alkylamines themselves and also eg. ethers such as diethyl ether and tetrahydrofuran, alcohols such as ethanol, dimethylformamide, dimethyl sulfoxide and acetonitrile.

Normally from 0.8 to 2.0, in particular from approximately 1.0 to 1.2, mol of nucleophile per mole of Vb are adequate. A larger excess of nucleophile, which in the case of the alkylamines can even be an amount of up to 20-fold per mole of Vb, in general provides no additional advantages.

According to present knowledge, the reaction proceeds at from 0° to 80° C., preferably from 0° to 30° C., at an adequate rate.

Compounds Vb and Vc in which R* is a phenol protective group can be converted into compounds Vb or Vc where R*=hydrogen by removal of the protective group (cf. eg. Th. W. Green "Protective Groups in Organic Synthesis", Wiley+Sons, pp. 87–108).

The compounds Vb and Vc where R*=hydrogen can be reacted with phenyl compounds III in a similar manner to method A) to give the substituted benzoxyphenyl derivatives I where Y=oxygen.

D)—nucleophilic substitution of chlorine or bromine in hydroximic acid chlorides or bromides IVc and alkylation of the products IVd or —alkylation of the hydroximic acid chlorides or bromides IVc and, if desired, nucleophilic substition of the products Vb

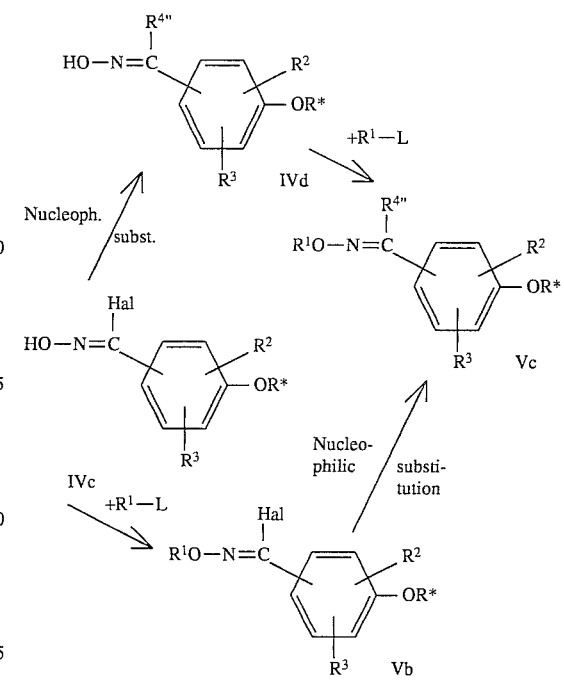

Suitable nucleophiles are in particular alkoxides (cf. for this eg. EP-A 158 153), alkylamines (cf. eg. J. Org. Chem. 45 (1980), p. 4198 ff und Heterocycles 26 (1987), p. 188) and alkylmercaptides (cf. eg. EP-A 426 460).

The explanations given under B) likewise apply here to the alkylation reactions. For the definition of L reference may be made to A).

With respect to the nucleophilic substitution, reference may be made to the explanations under C). The further reaction of the compounds Vb and Vc to give benzoxyphenyl derivatives of the formula I in which Y is oxygen is also described there.

E) Alkylation of hydroximic acid cyanides IVe {cf. eg. Liebigs Ann. Chem. 10, 1623–1629 (1989)}:

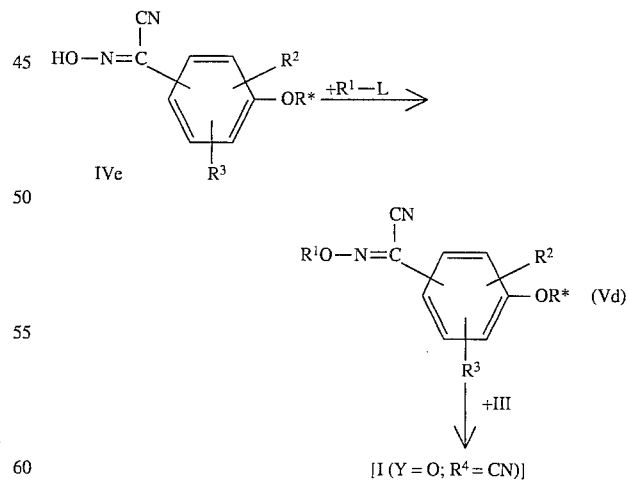

The explanations given under B) with respect to the alkylation reaction there likewise apply here. L was defined under A).

With respect to the further reaction of the compounds Vd with phenyl compounds III to give substituted phenoxymethylphenyl derivatives I where Y is oxygen and $R^4$ is cyano, reference may be made to the details under C).

F) By reaction of the substituted phenoxymethylphenyl derivatives of the formula I in which Y is oxygen, or of activated carboxylic acid derivatives VI with primary ($H_2N$—$R^6$) or secondary amines ($HN(CH_3)$—$R^6$), the corresponding compounds I where Y=—NH— or —N($CH_3$)— can be prepared:

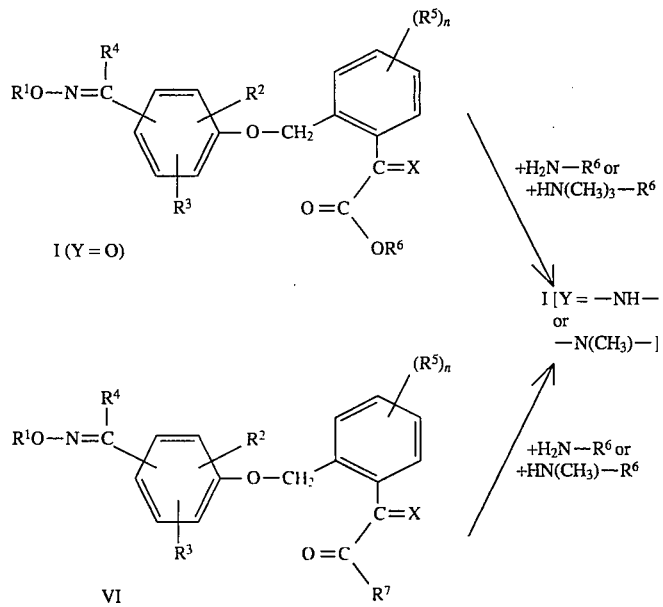

$R^7$ is a carbonyl-activating radical, eg. chlorine, bromine or 1-imidazolyl.

As a rule, the reactions can be performed in a manner known per se (cf. eg. Houben Weyl, Methoden der Organischen Chemie (Methods of Organic Chemistry), vol. E 5, S 941–977, pp. 983–991; Houben Weyl, Methoden der Organischen Chemie, vol. VIII, p. 654 ff).

The reaction is normally carried out in an inert solvent or diluent at from −10° to 60° C.

If the compounds I where Y=oxygen are used as starting materials, it has proven particularly advantageous to work at a reaction temperature of from 10° to 30° C. and with an approximately equimolar amount of amine or with an excess of amine up to a 10-fold amount, in each case based on I (Y=O). Suitable solvents in this connection are especially ethers such as tetrahydrofuran and dioxane, and alcohols such as methanol and ethanol. If desired, water can additionally be added to the solvents mentioned.

In the variant which starts from activated carboxylic acid derivatives VI, a reaction temperature of from −10° to 5° C. is particularly to be recommended, an amount of amine of from 0.9 to 5 mol, in particular from 0.95 to 2 mol, per mole of VI customarily being adequate for an optimum conversion. Suitable solvents in this case are especially ethers such as diethyl ether and tetrahydrofuran, aromatic hydrocarbons such as toluene, chlorinated hydrocarbons such as dichloromethane, or pyridine.

The activated carboxylic acid derivatives VI in turn are obtainable from the phenoxymethylphenyl derivatives I where —$YR^6$=OH (cf. for this eg. Houben Weyl, Methoden der Organischen Chemie (Methods of Organic Chemistry), vol. VIII, p. 463 ff).

The initial products of the formulae IVa, IVb and IVc are obtainable, for example, by the following processes:

G) preparation of the hydroximic acid esters IVa by reaction of benzonitriles VII with alcohols or thiols according to the Pinner reaction and subsequent reaction of the resulting imines with hydroxylamine (cf. eg. U.S. Pat. No. 4,743,701 and EP-A 158 153):

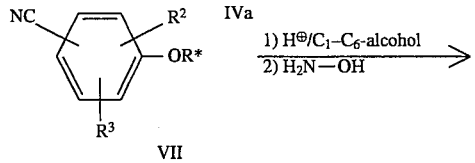

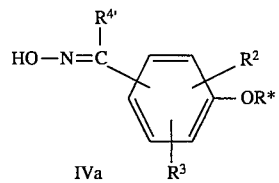

The reaction is normally carried out in an inert solvent or diluent. Suitable solvents are particularly ethers such as dioxane and chlorinated hydrocarbons such as chloroform. The reaction of VII with an alcohol can also be carried out in an excess of alcohol without additional solvent.

The amount of alcohol is not critical. Normally from 1 to 10 mol of alcohol per mole of VII are adequate for optimum reaction of VII. If the reaction is carried out without solvent in the alcohol concerned, this can also be present in a greater excess.

The amount of hydroxylamine is preferably from 0.9 to 10 mol, in particular from 1 to 2 mol, per mole of VII. The Pinner reaction is customarily performed at from 20° to 150° C., preferably from 40° to 80° C., against which from 0° to 60° C., preferably from 20° to 40° C., are to be recommended for the subsequent reaction with hydroxylamine.

H) Preparation of hydroximic acid halides IVc by oxidative halogenation of aldoximes IX:

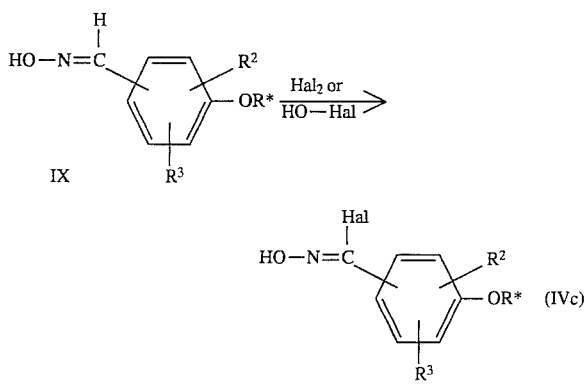

Suitable halogenating agents are, for example, elemental chlorine or bromine or hypohalites (cf. eg. EP-A 158 153; Houben-Weyl, Methoden der Organischen Chemie (Methods of Organic Chemistry), vol. VIII, p. 691; Synth. Commun. 16 (1986), 763–765; Gazz. Chim. Ital. 114 (1984), pp. 131–132).

Suitable solvents or diluents are eg. ethers such as diethyl ether and dioxane, chlorinated hydrocarbons such as dichloromethane, and also dimethylformamide or acetic acid.

In general, from 0.9 to 5, in particular from 1.0 to 1.5, mol of the halogenating agent per mole of IX are adequate for an optimum conversion.

It is recommended to perform the halogenation at a reaction temperature of from −10° to 60° C., in particular from −5° to 20° C.

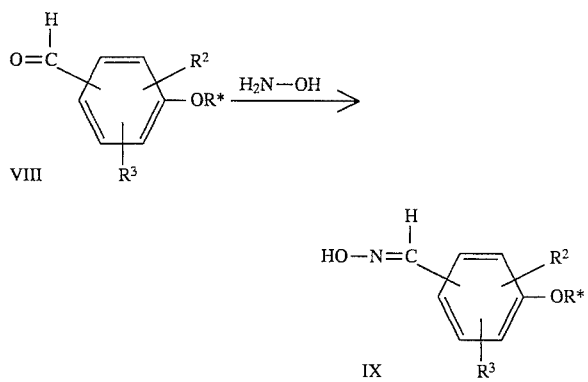

The aldoximes IX are in turn obtainable by reaction of benzaldehydes VIII with hydroxylamine (cf. eg. Houben-Weyl, Methoden der Organischen Chemie (Methods of Organic Chemistry), volume 10/4, 4th edtion, 1968, Georg-Thieme Verlag, Stuttgart, pages 55–66).

Suitable solvents or diluents are water, alcohols such as methanol and ethanol or mixtures of water and alcohol.

The hydroxylamine is preferably employed as the hydroxylammonium salt, in particular as the hydrochloride, acetate or sulfate, to be specific in an amount of from approximately 0.8 to 2.0, in particular from 0.95 to 1.2, mol per mole of VIII.

To neutralize the resulting acid it may be expedient to work in the presence of a base. Suitable bases are eg. alkali metal hydrogencarbonates such as sodium hydrogencarbonate, alkali metal acetates such as sodium acetate, ammonia and organic bases such as pyridine.

In general, from 1.0 to 1.7 mol of base per mole of hydroxylammonium salt are adequate.

The temperature range is normally from 0° to 80° C., in particular from 20° to 60° C.

J) Preparation of the hydroxamic acid esters IVb by reaction of benzoic acid derivatives XI with hydroxylamines $H_2N-OR^1$ (cf. for this Houben-Weyl, Methoden der Organischen Chemie (Methods of Organic Chemistry), vol. E5, pp. 1144–1146):

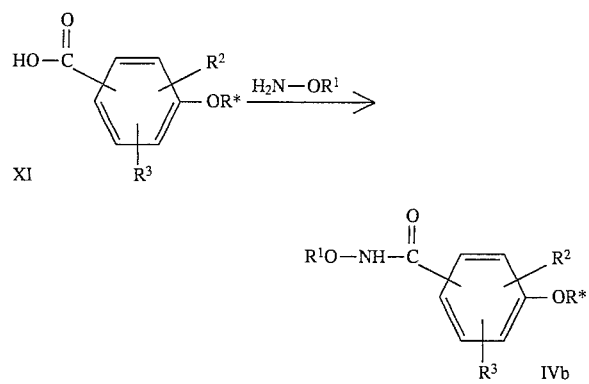

The benzoic acid derivatives XI in which R* is the radical

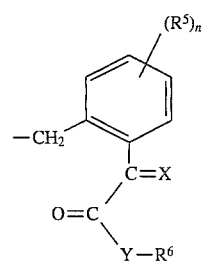

are novel (=α-methoxyiminophenylacetic acid methylamides XI').

Also novel are the compounds IVb in which R* is the radical

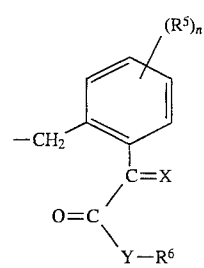

(=2-(phenoxymethyl)phenylacetic acid derivatives IVb')

The benzoic acid derivatives XI and the α-methoxyiminophenylacetic acid methylamides XI' are in turn obtainable by, for example — subjecting acetophenones X or X' to the haloform reaction (cf. for this eg. J. Am. Chem. Soc. 68 (1946), p. 1648 ff and J. Org. Chem. 12 (1947), p. 603 ff; Helv. Chim. Acta 49 (1966), p. 561 ff):

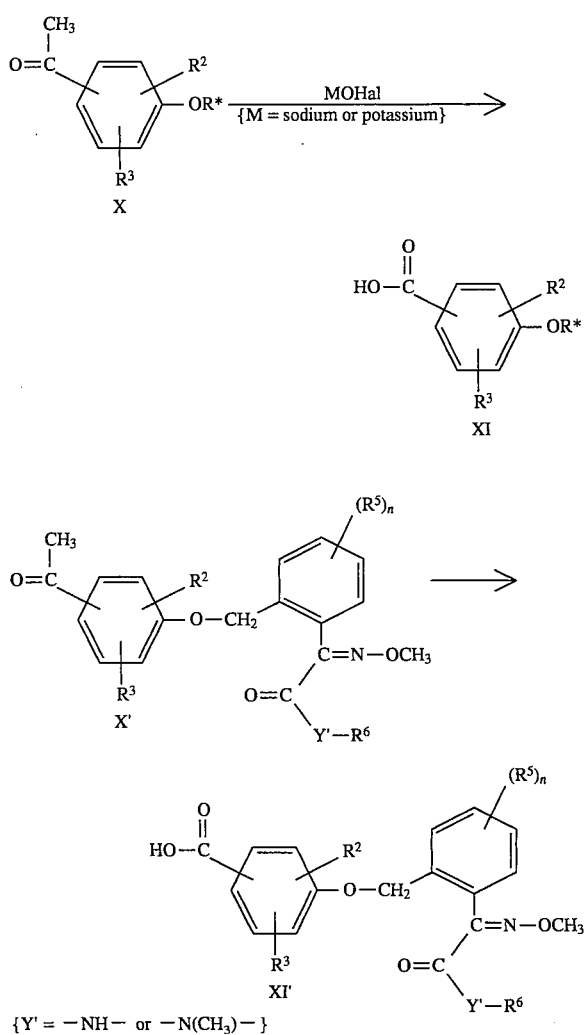

{Y' = —NH— or —N(CH₃)—}

Reagents which have proven particularly suitable are the alkali metal hypohalites such as sodium hypochlorite, potassium hypochlorite and sodium hypobromite. The amount of hypohalite is not particularly critical; it is expediently from 0.8 to 20 mol, in particular from approximately 1.0 to 10 mol, per mole of X or X'.

The reaction is advantageously carried out in water or water-dioxane mixtures at a reaction temperature of from approximately 0° to 100° C., particularly preferably from 5° to 30° C.

—or by carbonylating haloaromatics XII, advantageously with Pd catalysis (cf. for this J. Org. Met. Chem. 358 (1988), pp. 563–565; J. Org. Chem. 56 (1991), pp. 4320–4322 and U.S. Pat. No. 4,990,657):

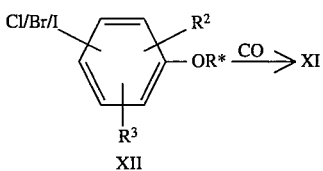

The carbonylation is preferably performed in a mixture of water and eg. tetramethylurea, toluene or dimethylformamide.

Catalysts which have proven suitable are palladium(II) compounds such as PdClhd 2, Pd(O—COCH₃)₂ and Pd[P(C₆H₅)₃]₂Cl₂, if desired with addition of P(C₆H₅)₃, a catalytic amount of catalyst, eg. from 0.01 to 0.1 mol, preferably from 0.01 to 0.05 mol per mole of XII, normally being adequate for the reaction.

The reaction is customarily carried out in the presence of a base, eg. of an alkali metal carbonate such as potassium carbonate, or of an organic base such as triethylamine or pyridine, the amount of base preferably being from approximately 1 to 10, in particular from 2 to 4, mol per mole of XII.

The reaction temperature is generally from 30° to 200° C., in particular from 100° to 150° C.

The carbonylation is particularly advantageously performed under a carbon monoxide overpressure of from 2 to 200 bar, in particular of approximately 50 bar.

Apart from the carbonylation of the haloaromatics XII, all reactions described above are expediently performed at atmospheric pressure or under the autogenous pressure of the respective diluent.

PREPARATION EXAMPLES

Example 1

E-2-Methoximino-2-[2-(4-[ethoximinomethoxymethyl]-2,5-dimethylphenoxymethyl)phenyl]acetic acid methylamide (Tab. 1, No. 1.004)

1.6 g of dimethyl sulfate were added dropwise at 20°–25° C. to a suspension of 3.1 g of 3.1 g of E-2-methoximino-2-[2-(4-ethoxyaminocarbonyl-2,5-dimethylphenoxymethyl)phenyl]acetic acid methylamide (prepared according to Example 5) and 1.74 g of finely powdered potassium carbonate in 60 ml of anhydrous acetone. After stirring for 16 hours, the reaction mixture was poured into 100 ml of ice water, which was mixed with 20 ml of dil. ammonia water. The mixture was extracted three times with methyl tert-butyl ether, after which the combined organic phases were washed with sat. sodium chloride solution, then dried over sodium sulfate and finally concentrated to dryness. The crude product was purified by medium pressure chromatography on silica gel (eluent: n-heptane/ethyl acetate 1:1 v/v). Yield: 0.45 g of the desired O-alkylated product as an oil.

¹H-NMR (in CDCl₃, TMS as internal standard): δ [ppm] =1.35(t,3H); 2.2(s,3H); 2.35(s,3H); 2.9(d,3H); 3.6(s,3H); 3.95(s,3H); 4.2(q,2H); 5.0(s,2H); 6.6(s,1H); 6.7(broad,NH); 7.1(s,1H); 0 7.2–7.6(m,4H)

Example 2

E-2-Methoximino-2-[2-(4-[chloroethoximinomethyl]-2,5-dimethylphenoxymethyl)phenyl]acetic acid methylamide (Tab. 1, No. 1.008)

3.3 g of E-2-methoximino-2-[2-(4-ethoxyaminocarbonyl-2,5-dimethylphenoxymethyl)phenyl]acetic acid methylamide (prepared according to Example 5) and 3.1 g of triphenylphosphine were dissolved in 30 ml of acetonitrile under anhydrous conditions. After addition of 3.7 g of tetrachloromethane, the reaction mixture was refluxed for 2 hours. It was then cooled to approximately 20° C. and separated by chromatography on a silica gel column (10 g of silica gel) (eluent: toluene/ethyl acetate 9:1). The eluate was worked up to the product in the customary manner. Yield: 1.9 g; m.p.: 87°–90° C.;

¹H-NMR (in CDCl₃, TMS as internal standard): δ [ppm] =1.35(t,3H); 2.15(s,3H); 2.35(s,3H); 2.9(d,3H); 3.9(s,3H); 4.3(q,2H); 5.0(s,2H); 6.6(s,1H); 6.75(broad,NH); 7.2–7.6(m,5H).

Example 3

E-2-Methoximino-2-[2-(4-[bromoethoximinomethyl]-2,5-dimethylphenoxymethyl)phenyl]acetic acid methylamide (Tab. 1, No. 1.009)

6,6 g of E-2-methoximino-2-[2-(4-ethoxyaminocarbonyl-2,5-dimethylphenoxymethyl)phenyl]acetic acid methylamide (prepared according to Example 5) and 6.2 g of triphenylphosphine were dissolved in 60 ml of acetonitrile under anhydrous conditions. After addition of 8.0 g of tetrabromomethane, the reaction mixture was refluxed for 4 hours, after which it was again treated with 2 g of tetrabromomethane. It was then refluxed for a further hour and then worked up to the product in a similar manner to Example 6. Yield: 4.8 g of crystalline product; m.p.: 74°–77° C.;

¹H-NMR (in CDCl₃, TMS as internal standard): δ [ppm] =1.3(t,3H); 2.15(s,3H); 2.35(s,3H); 2.9(d,3H); 3.95(s,3H); 4.3(q,2H); 4.95(s,2H); 6.6(s,1H); 6.75(broad,NH); 7.2–7.6(m,5H).

Example 4

E-2-Methoximino-2-[2-(4-[ethoximinomethylthiomethyl]-2,5-dimethylphenoxymethyl)phenyl]acetic acid methylamide (Tab. 1, No. 1.010)

0.42 g of solid sodium thiomethylate was added to a solution of 1.9 g of E-2-methoximino-2-[2-(4-[bromoethoximinomethyl]- 2,5-dimethylphenoxymethyl)phenyl]acetic acid methylamide (prepared according to Example 3) in 20 ml of anhydrous dimethylformamide. After stirring at about 20° C. for 16 hours, the reaction mixture was poured onto a mixture of ice water and methyl tert-butyl ether. The phases were separated and the aqueous phase was extracted a further three times with methyl tert-butyl ether.

After this the combined organic phases were washed with 20 ml of 2N sodium hydroxide solution and then with 100 ml of saturated sodium chloride solution, dried over sodium sulfate and concentrated. By triturating the residue with n-heptane/diisopropyl ether, 1.4 g of crystalline product were obtained; m.p.: 146°–148° C.

¹H-NMR (in CDCl₃, TMS as internal standard): δ [ppm] =1.35(t,3H); 1.85(s,3H); 2.2(s,3H); 2.3(s,3H); 2.9(d,3H); 3.95(s,3H); 4.3(q,2H); 5.0(s,2H); 6.65(s,1H); 6.75(broad, NH); 7.0(s,1H); 7.2–7.6(m,4H).

The following Table 1 contains further substituted benzoxyphenyl derivatives I which were prepared or can be prepared in the same manner.

TABLE 1

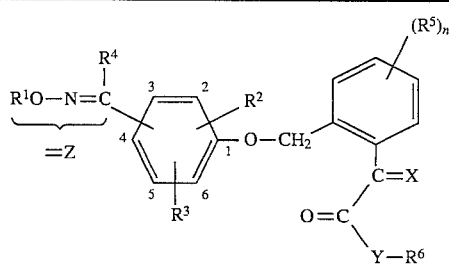

I

| No. | X | Y–R⁶ | (R⁵)ₙ | R² | R³ | Z | Physical data m.p. [°C.]/IR [cm⁻¹] ¹H–NMR [ppm] |
|---|---|---|---|---|---|---|---|
| 1.01 | E–NOCH₃ | NH–CH₃ | H | 2-CH₃ | 5-CH₃ | 4-C(OCH₃)=NOCH₃ | 2.2 (3H); 2.4 (3H); 3.6 (3H); 4.9 (2H); 6.6 (1H); 6.8 (NH); 7.1 (1H); 7.2–7.6 (4H) |
| 1.02 | E–NOCH₃ | NH–CH₃ | H | 2-CH₃ | 5-CH₃ | 4-C(Cl)=NOCH₃ | 3432, 1671, 1660, 1118, 1031 |
| 1.03 | E–NOCH₃ | NH–CH₃ | H | 2-CH₃ | 5-CH₃ | 4-C(OCH₃)=NOC₂H₅ | For NMR data see Example 1 |
| 1.04 | E–NOCH₃ | NH–CH₃ | H | 2-Cl | H | 4-C(OCH₃)=NOC₂H₅ | 80–82 |
| 1.05 | E–NOCH₃ | NH–CH₃ | H | 2-CH₃ | 5-CH₃ | 4-C(OC₂H₅)=NOCH₃ | 1.2 (3H); 2.2 (3H); 2.4 (3H); 2.9 (3H); 3.8 (2H); 3.9 (3H); 4.0 (3H); 4.9 (2H); 6.6 (1H); 6.8 (NH); 7.0 (1H); 7.2–7.5 (4H) |
| 1.06 | E–NOCH₃ | NH–CH₃ | H | 2-CH₃ | 5-CH₃ | 4-C(Br)=NOCH₃ | 98–101 |
| 1.07 | E–NOCH₃ | NH–CH₃ | H | 2-CH₃ | 5-CH₃ | 4-C(SCH₃)=NOCH₃ | 53–55 |
| 1.08 | E–NOCH₃ | NH–CH₃ | H | 2-CH₃ | 5-CH₃ | 4-C(Cl)=NOC₂H₅ | 87–90 |
| 1.09 | E–NOCH₃ | NH–CH₃ | H | 2-CH₃ | 5-CH₃ | 4-C(Br)=NOC₂H₅ | 79–77 |

TABLE 1-continued

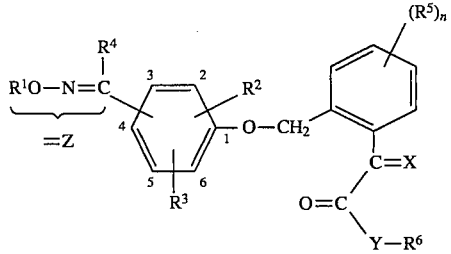

| No. | X | Y–R⁶ | (R⁵)ₙ | R² | R³ | Z | Physical data m.p. [°C.]/IR [cm⁻¹] ¹H–NMR [ppm] |
|---|---|---|---|---|---|---|---|
| 1.10 | E–NOCH₃ | NH–CH₃ | H | 2-CH₃ | 5-CH₃ | 4-C(SCH3)=NOC₂H₅ | 100–148 |
| 1.11 | E–NOCH₃ | NH–CH₃ | H | 2-CH₃ | 5-CH₃ | 4-C(Cl)=NOCH(CH₃)₂ | 3435, 1661, 1529, 1123, 981 |
| 1.12 | E–NOCH₃ | NH–CH₃ | H | 2-CH₃ | 5-CH₃ | 4-C(Br)=NOCH(CH₃)₂ | 65–67 |
| 1.13 | E–NOCH₃ | NH–CH₃ | H | 2-CH₃ | 5-CH₃ | 4-C(SCH3)=NOCH(CH₃)₂ | 123–126 |
| 1.14 | E–NOCH₃ | NH–CH₃ | H | 2-CH₃ | 5-CH₃ | 4-C(Cl)=NOCH₂CH=CH₂ | 92–95 |
| 1.15 | E–NOCH₃ | NH–CH₃ | H | 2-CH₃ | 5-CH₃ | 4-C(Br)=NOCH₂CH=CH₂ | 72–75 |
| 1.16 | E–NOCH₃ | NH–CH₃ | H | 2-CH₃ | 5-CH₃ | 4-C(SCH₃)=NOCH₂CH=CH₂ | 87–89 |
| 1.17 | E–NOCH₃ | NH–CH₃ | H | 2-CH₃ | 5-CH₃ | 4-C(SC₂H₅)=NOC₂H₅ | 150–152 |
| 1.18 | E–NOCH₃ | NH–CH₃ | H | 2-CH₃ | H | 4-C(Cl)=NOC₂H₅ | 89–92 |
| 1.19 | E–NOCH₃ | NH–CH₃ | H | 2-CH₃ | H | 4-C(Cl)=NOCH₂CH=CH₂ | 86–89 |
| 1.20 | E–NOCH₃ | NH–CH₃ | H | 2-CH₃ | H | 4-C(SC₆H₅)=NOCH₂CH=CH₂ | 59–61 |
| 1.21 | E–NOCH₃ | NH–CH₃ | H | 2-CH₃ | H | 4-C[S(4-Cl–C₆H₄)]=NOCH₂CH=CH₂ | 2.15 (3H); 2.9 (3H); 4.8 (2H); 4.9 (2H); 5.25 (1H); 5.35 (1H); 6.0 (1H); 6.6 (1H); 6.8 (NH); 7.0–7.5 (10H) |
| 1.22 | E–NOCH₃ | NH–CH₃ | H | 2-CH₃ | 5-CH₃ | 4-C(OC₂H₅)=NOCH(CH₃)₂ | 100–102 |
| 1.23 | E–NOCH₃ | NH–CH₃ | H | 2-CH₃ | 5-CH₃ | 4-C(OC₂H₅)=NOC₂H₅ | 3340, 2960, 1673, 1509, 1326, 1037 |
| 1.24 | E–NOCH₃ | NH–CH₃ | H | 2-CH₃ | 5-CH₃ | 4-C(SC₆H₅)=NOC₂H₅ | 3360, 2920, 1673, 1505, 1035 |
| 1.25 | E–NOCH₃ | NH–CH₃ | H | 2-CH₃ | 5-CH₃ | 4-C[S(4-Cl–C₆H₄)]=NOC₂H₅ | 3410, 2920, 1674, 1505, 1036 |
| 1.26 | E–NOCH₃ | NH–CH₃ | H | 2-CH₃ | H | 4-C(Cl)=NOCH₃ | 3350, 2945, 1671, 1500, 1236, 1133, 1037 |
| 1.27 | E–CHCH₃ | OCH₃ | H | 2-CH₃ | 5-CH₃ | 4-C(OCH₃)=NOC₂H₅ | 1.25 (3H); 1.5 (3H); 2.1 (3H); 2.2 (3H); 3.5 (3H); 3.65 (3H); 4.0 (2H); 4.8 (2H); 6.5 (1H); 7.0 (2H); 7.2 (1H); 7.3 (2H); 7.5 (1H) |
| 1.28 | E–CHCH₃ | OCH₃ | H | 2-CH₃ | 5-CH₃ | 4-C(Cl)=NOC₂H₅ | 1.27 (3H); 1.65 (3H); 2.2 (3H); 2.36 (3H); 3.7 (3H); 4.3 (2H); 4.9 (2H); 6.58 (1H); 7.0–7.6 (6H) |
| 1.29 | E–CHCH₃ | OCH₃ | H | 2-CH₃ | 5-CH₃ | 4-C(Cl)=NOCH₃ | 1.65 (3H); 2.2 (3H); 2.36 (3H); 3.7 (3H); 4.9 (2H); 6.6 (1H); 7.1–7.6 (6H) |
| 1.30 | E–CHCH₃ | OCH₃ | H | 2-CH₃ | 5-CH₃ | 4-C(1-triazolyl)=NOCH₃ | 1.4 (3H); 2.0 (3H); 2.2 (3H); 2.9 (3H); 3.95 (3H); 4.35 (2H); 4.97 (2H); 6.65 (1H); 6.75 (1H); 7.15 (1H); 7.2–7.6 (4H); 7.95 (1H); 9.24 (1H) |

Example 5

E-2-Methoximino-2-[2-(4-ethoxyaminocarbonyl-2,5-dimethylphenoxymethyl)phenyl]acetic acid methylamide (Tab. 2, No. 2.003)

A suspension of 5.15 g of O-ethylhydroxylamine hydrochloride and 50 ml of anhydrous dichloromethane was treated at 0° C. with 10.0 g of N-methylmorpholine. A solution of 18.6 g of 2-methoximino- 2-[2-(4-chlorocarbonyl-2,5-dimethylphenoxymethyl)phenyl]acetic acid methylamide (prepared according to Example 3) in 50 ml of dichloromethane was added dropwise to this mixture with ice cooling. After addition was complete, the reaction mixture was allowed to warm to 20°–25° C. and was stirred for a further 12 hours at this temperature. The solid fraction was then separated off and the solution obtained was concentrated to dryness. The residue obtained was stirred with ethyl acetate, after which the insoluble fraction here was separated off and dissolved in dichloromethane. The solution was extracted with dil. hydrochloric acid and water, then dried over sodium sulfate and concentrated. Yield: 17.4 g of the hydroxamide; m.p.: 177°–180° C.;

¹H-NMR (in CDCl₃, TMS as internal standard): δ [ppm] =1.3 (t,3H); 2,15 (s,3H); 2.4 (s,3H); 2.9 (d,3H); 3.95 (s,3H); 4.05 (q,2H); 4.95 (s,2H); 6.6 (s,1H); 6.75 (broad,NH); 7.2 (s,1H); 7.2–7.6 (m,4H); 8.5 (s,1H).

Example 6

E-2-Methoxyimino-2-[2-(4-ethoxyaminocarbonyl-2-methyphenoxymethyl)phenyl]acetic acid methylamide (Tab. 2, No. 2.06)

30 g of 2-Methoximino-2[2-(4-chlorocarbonyl-2-methylphenoxymethylphenyl]acetic acid amide were reacted with 8.6 g of O-ethylhydroxylamine hydrochloride in a similar manner to Example 5. After stirring at room temperature for 18 h, the mixture was worked up as described above. Yield 19.1 g of the hydroxamide; m.p.: 142°–145° C.

$^1$H-NMR (in CDCl$_3$, TMS as internal standard): δ [ppm] =1,2 (t,3H); 2.2(s,3H); 2.8 (d,3H); 3.9 (s,3H); 3.95 (q,2H); 4.9 (s,2H); 6.7 (d,1H); 6.9 (broad,NH); 7.1–7.6 (m,6H); 9.6 (broad,NH).

Example 7

E-2-Methoximino-2-[2-(4-[ethoxyimino-(4-chlorophenylthio)methyl]-2,5-dimethylphenoxymethyl)phenyl]acetic acid methylamide (Tab. 1, No. 1.21)

1.8 g of potassium carbonate and 1.44 g of 4-chlorothiophenol were added to a solution of 2.4 g of E-2-methoximino-2-[2-(4-(bromoethoximinomethyl)-2,5-dimethylphenoxymethyl)phenyl]acetic acid methylamide (prepared according to Example 3) in 20 ml of anhydrous dimethylformamide. After warming at 60° C. for 5 h, a further 1.4 g of 3-chlorothiophenol were metered in and the mixture was left at 60° C. for 1 h more. To work up the mixture, it was stirred into ice water and extracted with methyl tert-butyl ether. The combined organic phases were washed with sodium carbonate solution and water, dried over sodium sulfate and concentrated on a rotary evaporator. The residue was chromatographed on a silica gel column (eluent toluene/ethyl acetate 95:5): 1.7 g of the title compound were obtained as a yellow oil.

$^1$H-NMR (in CDCl$_3$, TMS as internal standard): δ [ppm] =1.35 (t,3H); 2.0 (s,3H); 2.1 (s,3H); 2.9 (d,3H); 3.9 (s,3H); 4.3 (q,2H); 4.8 (s,2H); 6.4 (s,1H); 6.7 (broad,NH); 6.8 (s,1H); 7.0–7.5 (m,8H).

Precursor α)

E-2-Methoximino-2-[2-(4-acetyl-2,5-dimethylphenoxymethyl)phenyl]acetic acid methylamide 8.5 ml of a 40% strength by weight aqueous methylamine solution were added to a mixture of 18.45 g of methyl 2-methoxyimino- 2-[2-(4-acetyl-2,5-dimethylphenoxymethyl)phenyl]acetate and 180 ml of tetrahydrofuran. After stirring at 20°–25° C. for 16 hours, the reaction mixture was poured onto 200 ml of ice water/100 ml of methyl tert-butyl ether. Dilute hydrochloric acid was subsequently added to this mixture until the aqueous phase had a pH of from 2 to 3. After separation of the phases, the aqueous phase was extracted several times with methyl tert-butyl ether. The combined organic phases were washed with saturated sodium chloride solution until neutral, dried and concentrated. Yield: 17.6 g; m.p.: 146°–148° C.;

$^1$H-NMR (in CDCl$_3$, TMS as internal standard): δ [ppm] =2.2 (s,3H); 2.5 (s,3H); 2.55 (s,3H); 2.9 (d,3H); 3.95 (s,3H); 5.0(s,2H); 6.65(s,1H); 6.75(broad,NH); 7.2–7.6(m,5H).

Precursor β)

E-2-Methoximino-2-[2-(4-carboxy-2,5-dimethylphenoxymethyl)phenyl]acetic acid methylamide 24 g of bromine were slowly added dropwise to a solution of 20 g of sodium hydroxide in 120 ml of water cooled to 10° C. such that the temperature did not exceed 10° C. The bromoform solution obtained was treated with ice cooling with a solution of 17 g of the E-2-methoximino-2-[2-(4-acetyl-2,5-dimethylphenoxymethyl)phenyl]acetic acid methylamide obtained from precursor α) in 150 ml of dioxane. After stirring at 20°–25° C. for a further hour, 50 ml of 20% strength by weight sodium hydrogen sulfite solution were added to remove excess bromoform. The solid product was obtained by acidifying the reaction mixture to a pH of 2 with conc. hydrochloric acid. It was separated off, stirred twice with petroleum ether and dried at 60° C. Yield: 18.5 g; m.p.: 195°–197° C.

$^1$H-NMR (in CDCl$_3$, TMS as internal standard): δ [ppm] =2.2 (s,3H); 2.6 (s,3H); 2.9 (d,3H); 3.95 (s,3H); 5.0 (s,2H); 6.6 (s,1H); 6.75 (broad,NH); 7.2–7.6 (m,4H); 7.85 (s,1H).

Precursor γ)

2-Methoximino-2-[2-(4-chlorocarbonyl-2,5-dimethylphenoxymethyl) phenyl]acetic acid methylamide A solution of 9.2 g of the E-2-methoximino-2-[2-(4-carboxy- 2,5-dimethylphenoxymethyl)-phenyl]acetic acid methylamide obtained from precursor D) in 100 ml of anhydrous dichloromethane was treated with a few drops of dimethylformamide. 4.5 g of thionyl chloride was then added dropwise to this mixture at 20°–25° C., after which the reaction mixture was refluxed for 1.5 hours. It was then allowed to cool and the readily volatile fractions were removed under reduced pressure. The residue was finally taken up once more with 100 ml of dichloromethane and recovered again by concentrating the solution. Yield: 9.3 g of acid chloride as a pale yellow solid which it was possible to use for subsequent reactions without further purification.

$^1$H-NMR (in CDCl$_3$, TMS as internal standard): δ [ppm] =2.2 (s,3H); 2.6 (s,3H); 2.95 (s,3H); 4.0 (s,3H); 4.95 (s,2H); 6.6 (s,1H); 7.2–7.6 (m,4H); 7.85 (s,1H); 8.1 (broad,1H).

Precursor δ)

E-2-Methoximino-2-[2-(4-carboxy-2-methylphenoxymethyl)phenyl]acetic acid methylamide In a similar manner to the process for precursor β), 145 g of E-2-methoximino-2-[2-(4-acetyl-2-methylphenoxymethyl)phenyl)acetic acid methylamide in 1400 ml of dioxane were reacted to give the carboxylic acid. To work up the mixture, it was adjusted to pH=2 using conc. sulfuric acid and extracted with dichloromethane. The combined organic phases were washed until neutral, dried over sodium sulfate and concentrated on a rotary evaporator. The residual solid was triturated with diisopropyl ether, filtered off with suction and dried. Yield: 110 g, m.p.: 185° C. (dec.)

$^1$H-NMR (in CDCl$_3$, TMS as internal standard): δ [ppm] =2.25 (s,3H); 2.9 (d,3H); 3.95 (s,3H); 5.0 (s,2H); 6.75 (broad,NH); 6.85 (d,1H); 7.1–7.5 (m,4H); 7.9 (m,2H); 11.0 (broad,OH).

Precursor ε)

Methyl 2-[2-(4-carboxy-2,5-dimethylphenoxymethyl)phenyl]E-but-2-enoate

In a similar manner to the process for precursor δ), 9.6 g of methyl 2-[2-(acetyl-2,5-dimethylphenoxymethyl)phenyl] E-but-2-enoate in 60 ml of dioxane were reacted to give the carboxylic acid. After concentrating on a rotary evaporator a yellow oil remained which in addition to 70% of the title compound contained a further 30% of the diacid formed by hydrolysis of the methyl butanoate.

The compounds according to the invention (see eg. Table 1, Nos. 1.29 to 1.32) were obtained from this crude product in a similar manner to the processes described here and after corresponding chromatographic separation of the diacid derivatives $^1$H-NMR (in DMSO, TMS as internal standard): δ [ppm] =1.6 (d,3H); 2.1 (s,3H); 2.5 (s,3H); 3.6 (s,3H); 5.0 (s,2H); 6.8 (s,1H); 7.1 (q,1H); 7.4–7.5 (m,2H); 7.6 (m, 1H); 7.7 (m,2H).

Precursor χ)

Methyl E-2-Methoximino-2-[2-(4-carboxy-2-methylphenoxymethyl)phenyl]acetate 2.2 g of methyl E-2-methoximino-2-[2-(4-iodo-2-methylphenoxymethyl)phenyl]acetate, 0.35 g of bistriphenylphosphinopalladium(II) chloride and 80 ml of tetramethylurea were initially introduced into 50 ml of water in a 300 ml HC autoclave. Carbon monoxide was then injected up to a pressure of 30 bar and the mixture was heated to 100° C. After the heating phase, the CO pressure was adjusted to 100 bar. This pressure was regulated hourly. After 24 h, the mixture was filtered and tetramethylurea was distilled from the filtrate at 75° C. in an oil pump vacuum (0.2 mbar). On taking up the remaining residue in MTBE/aqueous NaHCO$_3$ solution, the product precipitated. After filtering off with suction and drying, 0.9 g of the title compound was obtained. M.p.: 192° C.

$^1$H-NMR (in CDCl$_3$, TMS as internal standard): δ [ppm] =2.1 (s,3H); 3.7 (s,3H); 3.9 (s,3H); 5.0 (s,2H); 7.0 (d,1H); 7.25 (d,1H); 7.45 (m,2H); 7.55 (d,1H); 7.25 (m,2H).

The following Table 2 lists further 2-(phenoxymethyl)phenylacetic acid derivatives IVb' which were prepared or can be prepared in a similar manner to Example 5.

TABLE 2

IVb'

| No. | X | Y–R$^6$ | (R$^5$)$_n$ | R$^2$ | R$^3$ | T | Physical data m.p. [°C.]/ IR [cm$^{-1}$] $^1$H–NMR [ppm] |
|---|---|---|---|---|---|---|---|
| 2.01 | E–NOCH$_3$ | NH–CH$_3$ | H | 2-Cl | H | 4-{–CO–NH–OCH$_3$} | 3340, 1662, 1493, 1270, 1037 |
| 2.02 | E–NOCH$_3$ | NH–CH$_3$ | H | 2-CH$_3$ | 5-CH$_3$ | 4-{–CO–NH–OCH$_3$} | 141–145 |
| 2.03 | E–NOCH$_3$ | NH–CH$_3$ | H | 2-CH$_3$ | 5-CH$_3$ | 4-{–CO–NH–OC$_2$H$_5$} | 177–180 |
| 2.04 | E–NOCH$_3$ | NH–CH$_3$ | H | 2-CH$_3$ | 5-CH$_3$ | 4-{–CO–NH–OCH$_2$CH=CH$_2$} | 130–134 |
| 2.05 | E–NOCH$_3$ | NH–CH$_3$ | H | 2-CH$_3$ | 5-CH$_3$ | 4-{–CO–NH–OCH(CH$_3$)$_2$} | 171–175 |
| 2.06 | E–NOCH$_3$ | NH–CH$_3$ | H | 2-CH$_3$ | H | 4-{–CO–NH–OC$_2$H$_5$} | 142–145 |
| 2.07 | E–NOCH$_3$ | NH–CH$_3$ | H | 2-CH$_3$ | H | 4-{–CO–NH–OCH$_2$CH=CH$_2$} | 127–129 |

The substituted benzoxyphenyl derivatives I are suitable for controlling harmful fungi and pests of the insects, arachnids and nematodes class. They can be employed as fungicides and pesticides in crop protection and in the hygiene, stored material protection and veterinary sectors.

The harmful insects include:

—from the order of the butterflies (Lepidoptera), for example, *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobla brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridromia saucia, Phalera bucephola, Phthorimaea operculella, Phyllocnistis citrella, Pieris brassicae, Plathypena scabra, Plutella xylostella, Pseudoplusia includens, Rhyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni, Zeiraphera canadensis;*

—from the order of the beetles (Coleoptera), for example, *Agrilus sinuatus, Agriotes lineatus, Agriotes obscurus,*

*Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrhynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllophaga sp., Phyllopertha horticola, Phyllotreta chrysocephala, Phyllotreta nemorum, Phyllotreta striolata, Popillia japonica, Sitona lineatus, Sitophilus granaria;*

—from the order of the dipterous insects (Diptera), for example, *Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex pipiens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia cuprina, Lucilia sericata, Lycoria pectoralis, Mayetiola destructor, Musca domestica, Muscina stabulans, Oestrus ovis, Oscinella frit, Pegomya hyoscyami, Phorbia antiqua, Phorbia brassicae, Phorbia coarctata, Rhagoletis cerasi, Rhagoletis pomonella, Tabanus bovinus, Tipula oleracea, Tipula paludosa;*

—from the order of the thrips (Thysanoptera), for example, *Frankliniella fusca, Frankliniella occidentalis, Frankliniella tritici, Scirtothrips citri, Thrips oryzae, Thrips palmi, Thrips tabaci;*

—from the order of the hymenopterous insects (Hymenoptera), for example, *Athalia rosae, Atta cephalotes, Atta sexdens, Atta texana, Hoplocampa minuta, Hoplocampa testudinea, Monomorium pharaonis, Solenopsis geminata, Solenopsis invicta;*

—from the order of the bed bugs (Heteroptera), for example, *Acrosternum hilare, Blissus leucopterus, Cyrtopeltis notatus, Dysdercus cingulatus, Dysdercus intermedius, Eurygaster integriceps, Euchistus impictiventris, Leptoglossus phyllopus, Lygus lineolaris, Lygus pratensis, Nezara viridula, Piesma quadrata, Solubea insularis, Thyanta perditor;*

—from the order of the plant-sucking insects (Homoptera), for example, *Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphumavenae, Macrosiphum euphorbiae, Macrosiphon rosae, Megoura viciae, Metopolophium dirhodum, Myzodes persicae, Myzus cerasi, Nilaparvata lugens, Pemphigus bursarius, Perkinsiella saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum, Viteus vitifolii;*

—from the order of the termites (Isoptera), for example, *Calotermes flavicollis, Leucotermes flavipes, Reticulitermes lucifugus, Termes natalensis;*

—from the order of the orthopterous insects (Orthoptera), for example, *Acheta domestica, Blatta orientalis, Blattella germanica, Forficula auricularia, Gryllotalpa gryllotalpa, Locusta migratoria, Melanoplus birittatus, Melanoplus femur-rubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus, Tachycines asynamorus.*

The harmful arachnids (Acarina) include, for example, *Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Saccoptes scabiei, Tetranychus cinnabarinus, Tetranychus kanzawai, Tetranychus pacificus, Tetranychus telarius, Tetranychus urticae.*

Examples of harmful nematodes are, for example, root gall nematodes, eg. *Meloidogyne hapla, Meloidogyne incognita, Meloidogyne javanica,* cyst-forming nematodes, eg. *Globodera rostochiensis, Heterodera avenae, Heterodera glycinae, Heterodera schatii, Heterodera trifolii,* stem and leaf eelworms, eg. *Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus, Pratylenchus goodeyi.*

The substituted benzoxyphenyl derivatives I are in some cases systemically active as fungicides. They can be employed as foliar and soil fungicides against a broad spectrum of phytopathogenic fungi, in particular from the Ascomycetes, Deuteromycetes, Phycomycetes and Basidiomycetes classes.

They are of particular importance for the control of a multiplicity of fungi on various crop plants such as wheat, rye, barley, oats, rice, corn, grass, cotton, soybeans, coffee, sugar cane, grapes, fruit and decorative plants and vegetable plants such as cucumbers, beans and cucurbits, and on the seeds of these plants.

The compounds I are specifically suitable for the control of the following plant diseases:

* *Erysiphe graminis* (powdery mildew) in cereals,
* *Erysiphe cichoracearum* and *Sphaerotheca fuliginea* on cucurbits,
* *Podosphaera leucotricha* on apples,
* *Uncinula necator* on vines,
* *Puccinia* species on cereals,
* *Rhizoctonia* species on cotton and grass,
* *Ustilago* species on cereals and sugar cane,
* *Venturia inaequalis* (scab) on apples,
* *Helminthosporium* species on cereals,
* *Septoria nodorum* on wheat,
* *Botrytis cinerea* (gray mold) on strawberries, vines,
* *Cercospora arachidicola* on groundnuts,
* *Pseudocercosporella herpotrichoides* on wheat, barley,
* *Pyricularia oryzae* on rice,
* *Phytophthora infestans* on potatoes and tomatoes,

* *Fusarium* and *Verticillium* species on various plants,
* *Plasmopara viticola* on vines,
* *Alternaria* species on vegetables and fruit.

The novel compounds can also be employed in the protection of materials (preservation of wood), eg. against *Paecilomyces variotii*.

They can be converted into the customary formulations, such as solutions, emulsions, suspensions, dusts, powders, pastes or granules. The use forms here depend on the particular intended use; in each case they should if possible guarantee the finest dispersion of the active compounds.

The formulations are prepared in a known manner, eg. by extending the active compound with solvents and/or carriers, if desired using emulsifiers and dispersants, where if water is used as a diluent other organic solvents can also be used as auxiliary solvents.

Suitable auxiliaries for this purpose are mainly:

—solvents such as aromatics (eg. xylene), chlorinated aromatics (eg. chlorobenzenes), paraffins (eg. petroleum fractions), alcohols (eg. methanol, butanol), ketones (eg. cyclohexanone), amines (eg. ethanolamine, dimethylformamide) and water;

—carriers such as ground natural minerals (eg. kaolins, aluminas, talc, chalk) and ground synthetic minerals (eg. highly disperse silica, silicates);

—emulsifiers such as nonionic and anionic emulsifiers (eg. polyoxyethylene fatty alcohol ethers, alkylsulfonates and arylsulfonates) and —dispersants such as lignin-sulfite waste liquors and methylcellulose.

Suitable surface-active substances are the alkali metal, alkaline earth metal and ammonium salts of aromatic sulfonic acids, eg. lignosulfonic, phenolsulfonic, naphthalenesulfonic and dibutylnaphthalenesulfonic acid, and also of fatty acids, alkyl- and alkylarylsulfonates, alkyl-, lauryl ether and fatty alcohol sulfates, as well as salts of sulfated hexa-, hepta- and octadecanols, and also of fatty alcohol glycol ethers, condensation products of sulfonated naphthalene and its derivatives with formaldehyde, condensation products of naphthalene or of the naphthalenesulfonic acids with phenol and formaldehyde, polyoxyethylene octylphenol ether, ethoxylated isooctyl-, octyl- or nonylphenol, alkylphenol or tributylphenylpolyglycol ethers, alkylaryl polyether alcohols, isotridecyl alcohol, fatty alcohol ethylene oxide condensates, ethoxylated castor oil, polyoxyethylene or polyoxypropylenealkyl ethers, lauryl alcohol polyglycol ether acetate, sorbitol esters, lignin-sulfite waste liquors or methylcellulose. Aqueous use forms can be prepared from emulsion concentrates, dispersions, pastes, wettable powders or water-dispersible granules by addition of water. To prepare emulsions, pastes or oil dispersions, the substrates can be homogenized in water as such or dissolved in an oil or solvent, by means of wetting agents, adhesives, dispersants or emulsifiers. However, concentrates consisting of active substance, wetting agent, adhesive, dispersant or emulsifier and possibly solvent or oil can also be prepared which are suitable for dilution with water.

Powder, scattering and dusting compositions can be prepared by mixing or joint grinding of the active substances with a solid carrier.

Granules, eg. coated, impregnated and homogeneous granules, can be prepared by binding the active compounds to solid carriers.

Solid carriers are mineral earths such as silica gel, silicic acids, silicates, talc, kaolin, limestone, lime, chalk, bole, loess, clay, dolomite, diatomaceous earth, calcium sulfate and magnesium sulfate, magnesium oxide, ground synthetic materials, fertilizers, such as ammonium sulfate, ammonium phosphate, ammonium nitrate, ureas and vegetable products, such as cereal flour, tree bark meal, wood meal and nutshell meal, cellulose powder or other solid carriers. The active compound concentrations in the ready-to-use preparations can be varied within relatively wide ranges.

Very generally, the compositions contain from 0.0001 to 95% by weight of active compound.

Formulations containing more than 95% by weight of active compound can be applied highly successfully in the ultra-low volume process (ULV), it even being possible to use the active compound without additives.

For use as fungicides, concentrations of from 0.01 to 95% by weight, preferably of from 0.5 to 90% by weight, of active compound are recommended. For use as insecticides, formulations containing from 0.0001 to 10% by weight, preferably from 0.01 to 1% by weight, are suitable.

The active compounds are normally employed in a purity of from 90% to 100%, preferably from 95% to 100% (according to NMR spectrum).

Examples of such preparations are:

I. a solution of 90 parts by weight of the compound No. I.01 and 10 parts by weight of N-methyl-a-pyrrolidone, which is suitable for application in the form of very small drops;

II. a solution of 20 parts by weight of the compound No. I.02 in a mixture of 80 parts by weight of alkylated benzene, 10 parts by weight of the addition product of from 8 to 10 mol of ethylene oxide to 1 mol of oleic acid N-monoethanolamide, 5 parts by weight of calcium salt of dodecylbenzenesulfonic acid, 5 parts by weight of the addition product of 40 mol of ethylene oxide to 1 mol of Castor oil; a dispersion is obtained by finely dispersing the formulation in water.

III. a solution of 20 parts by weight of the compound No. I.03 in a mixture of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil; a dispersion is obtained by finely dispersing the formulation in water.

IV. an aqueous dispersion of 20 parts by weight of the compound No. I.04 in a mixture of 25 parts by Weight of cyclohexanone, 65 parts by weight of a petroleum fraction of boiling point from 210° to 280° C. and 10 parts by weight of the addition product of 40 mol of ethylene oxide to 1 mol of castor oil; a dispersion is obtained by finely dispersing the formulation in water.

V. a mixture, ground in a hammer mill, of 20 parts by weight of the compound No. I.01, 3 parts by weight of the sodium salt of diisobutylnaphthalene-e-sulfonic acid, 17 parts by weight of the sodium salt of a lignosulfonic acid from a sulfite waste liquor and 60 parts by weight of powdered silica gel; a spray mixture is obtained by finely dispersing the mixture in water;

VI. an intimate mixture of 3 parts by weight of the compound No. I.02 and 97 parts by weight of finely divided kaolin; this dusting composition contains 3% by weight of active compound;

VII. an intimate mixture of 30 parts by weight of the compound No. I.03, 92 parts by weight of powdered silica gel and 8 parts by weight of liquid paraffin which has been sprayed onto the surface of this silica gel; this preparation gives the active compound a good adhesion;

VIII. a stable aqueous dispersion of 40 parts by weight of the compound No. I.04, 10 parts by weight of the sodium salt of a phenolsulfonic acid/urea/formaldehyde condensate, 2 parts by weight of silica gel and 48 parts by weight of water, which can be further diluted;

IX. a stable oily dispersion of 20 parts by weight of the compound No. I.01, 2 parts by weight of the calcium salt of dodecylbenzenesulfonic acid, 8 parts by weight of fatty alcohol polyglycol ether, 2 parts by weight of the sodium salt of a phenolsulfonic acid/urea/formaldehyde condensate and 68 parts by weight of a paraffinic mineral oil;

X. a mixture, ground in a hammer mill, of 10 parts by weight of the compound No. 2.1, 4 parts by weight of the sodium salt of diisobutylnaphthalene-α-sulfonic acid, 20 parts by weight of the sodium salt of a lignosulfonic acid from a sulfite waste liquor, 38 parts by weight of silica gel and 38 parts by weight of kaolin. By finely dispersing the mixture in 10,000 parts by weight of water, a spray mixture is obtained which contains 0.1% by weight of the active compound.

The compounds are applied by treating the fungi or the seeds, plants, materials or the soil to be protected from fungal attack with a fungicidally active amount of the active compounds.

They are applied before or after the infection of the materials, plants or seeds by the fungi.

Depending on the type of effect desired, the application rates are from 0.02 to 3 kg of active compound per ha, preferably from 0.1 to 1 kg/ha.

In seed treatment, amounts of active compound of from 0.001 to 50 g, preferably from 0.01 to 10 g, per kilogram of seed are in general needed.

The application rate of active compound for controlling pests under outdoor conditions is from 0.02 to 10, preferably from 0.1 to 2.0 kg/ha.

The compounds I, on their own or in combination with herbicides or fungicides, can also be applied jointly mixed with further crop protection agents, for example with growth regulators or with agents for controlling pests or bacteria. Of interest is also the miscibility with fertilizers or with mineral salt solutions which are employed for eliminating nutritional and trace element deficiencies.

The crop protection agents and fertilizers can be added to the compositions according to the invention in a weight ratio of from 1:10 to 10:1, if appropriate even immediately before use (tank mix). On mixing with fungicides or insecticides, in many cases an increase in the fungicidal spectrum of action is obtained here.

The following list of fungicides with which the compounds according to the invention can be applied together is intended to illustrate the combination possibilities, but not restrict them:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediamine bisdithiocarbamate,
tetramethylthiuram disulfide,
ammonia complex of zinc N,N-ethylenebisdithiocarbamate,
ammonia complex of zinc N,N'-propylenebisdithiocarbamate,
zinc N,N'-propylenebisdithiocarbamate,
N,N'-polypropylenebis(thiocarbamoyl) disulfide;
nitro derivatives, such as dinitro(1-methylheptyl)phenyl crotonate,
2-sec-butyl-4,6-dinitrophenyl 3,3-dimethylacrylate,
2-sec-butyl-4,6-dinitrophenyl isopropyl carbonate,
diisopropyl 5-nitroisophthalate;
heterocyclic substances, such as 2-heptadecyl-2-imidazoline acetate,
2,4-dichloro-6-(o-chloroanilino)-s-triazine,
O,O-diethyl phthalimidophosphonothioate,
5-amino-1-β-[bis-(dimethylamino)-phosphinyl]-3-phenyl-1,2,4 -triazole,
2,3-dicyano-1,4-dithioanthraquinone, 2-thio-1,3-dithiolo-β-4,5-b]quinoxaline,
methyl 1-(butylcarbamoyl)-2-benzimidazolecarbamate,
2-methoxycarbonylaminobenzimidazole,
2-(fur-2-yl)benzimidazole,
2-(thiazol-4-yl)benzimidazole,
N-(1,1,2,2-tetrachloroethylthio)tetrahydrophthalimide,
N-trichloromethylthiotetrahydrophthalimide,
N-trichloromethylthiophthalimide,
N-dichlorofluoromethylthio-N',N'-dimethyl-N-phenylsulfamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine-1-oxide,
8-hydroxyquinoline or its copper salt,
2,3-dihydro-5-carboxanilido-6-methyl-1,4-oxathiin,
2,3-dihydro-5-carboxanilido-6-methyl-1,4-oxathiin-4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
N-cyclohexyl-2,5-dimethylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethyl acetal,
piperazine-1,4-diylbis(1-(2,2,2-trichloroethyl))formamide,
1-(3,4-dichloroanilino)-1-formylamino-2,2,2-trichloroethane,
2,6-dimethyl-N-tridecylmorpholine or its salts,
2,6-dimethyl-N-cyclododecylmorpholine or its salts,
N-[3-(p-tert-butylphenyl)-2-methylpropyl]-cis-2,6-dimethylmorpholine,
N-[3-(p-tert-butylphenyl)-2-methylpropyl]piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)-2-butanone,
1-(4-chlorophenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-2-dimethylamino-4-hydroxy-6-methylpyrimidine,
bis(p-chlorophenyl)-3-pyridinemethanol,
1,2-bis(3-ethoxycarbonyl-2-thioureido)benzene,
1,2-bis(3-methoxycarbonyl-2-thioureido)benzene, and also various fungicides, such as dodecylguanidine acetate,
3-[3-(3,5-dimethyl-2-oxycyclohexyl)-2-hydroxyethyl]glutarimide, hexachlorobenzene,
DL-methyl-N-(2,6-dimethylphenyl)-N-2-furoyl alaninate,
DL-N-(2,6-dimethylphenyl)-N-(2'-methoxyacetyl)alanine methyl ester,
N-(2,6-dimethylphenyl)-N-chloroacetyl-D,L-2-aminobutyrolactone,
DL-N-(2,6-dimethylphenyl)-N-(phenylacetyl)alanine methyl ester,
5-methyl-5-vinyl-3-(3,5-dichlorophenyl)-2,4-dioxo-1,3-oxazolidine,
3-(3,5-dichlorophenyl)-5-methyl-5-methoxymethyl-1,3-oxazolidine-2,4-dione,
3-(3,5-dichlorophenyl)-1-isopropylcarbamoylhydantoin,
N-(3,5-dichlorophenyl)-1,2-dimethylcyclopropane-1,2-dicarboximide,
2-cyano-[N-ethylaminocarbonyl-2-methoximino]acetamide,
1-[2-(2,4-dichlorophenyl)pentyl]-1H-1,2,4-triazole,
2,4-difluoro-α-(1H-1,2,4-triazolyl-1-methyl)benzhydryl alcohol,
N-(3-chloro-2,6-dinitro-4-trifluoromethylphenyl)-5 -trifluoromethyl-3-chloro-2-aminopyridine,
1-((bis(4-fluorophenyl)methylsilyl)methyl)-1H-1,2,4-triazole.

Use Examples (fungicidal activity)

The comparison substance used was

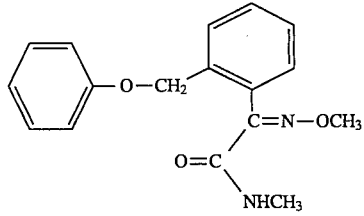

disclosed in EP-A 398 692 (Table 3, No. 46).

Use Example 1

Activity against brown rust of wheat

Leaves of wheat seedlings of the variety Kanzler grown in pots were dusted with spores of brown rust (*Puccinia recondita*). The pots were then placed for 24 hours at from 20° to 22° C. in a chamber having high atmospheric humidity (from 90 to 95%). During this time the spores germinated and the germ tubes penetrated into the leaf tissue. The infected parts were then sprayed with aqueous spray mixtures which contained 80% by weight of active compound and 20% by weight of emulsifier in the dry matter until dripping wet. After the spray coating had dried on, the test plants were placed in a greenhouse at from 20° to 22° C. and from 65 to 70% relative atmospheric humidity. After 8 days, the extent of the rust fungus development on the leaves was determined.

By treatment with aqueous active compound preparations which contained 63 ppm of the compound No. I.01, 1.02, 1.03, 1.04, 1.05, 1.07, 1.08, 1.09, 1.10, 1.11, 1.14, 1.15 or 1.16, it was largely possible to prevent the fungal attack (0–15%).

Plants which were treated with an aqueous preparation of the comparison compound (concentration: 63 ppm) on the other hand showed, like the untreated control plants, 65% fungal attack on the leaves.

Use Example 2

Activity against *Pyricularia oryzae* (protective)

Leaves of rice seedlings of the variety Tai-Nong 67 grown in pots were sprayed with aqueous emulsions which contained 80% by weight of active compound and 20% by weight of emulsifier in the dry matter until dripping wet and inoculated 24 hours later with an aqueous spore suspension of *Pyricularia oryzae*. The test plants were then placed in climatic chambers at 22°–24° C. and 95–99% relative atmospheric humidity. After 6 days the extent of disease attack was determined.

While the leaves of untreated control plants were attacked up to 70% by fungus, the plants treated with aqueous preparations [concentration: 63 ppm] of the compounds Nos. 1.01, 1.03, 1.04, 1.05, 1.07, 1.08, 1.10, 1.11, 1.13, 1.14, 1.15 and 1.16 only showed 0–25% fungal attack on the leaves.

By application of an aqueous preparation of the comparison compound [concentration: 63 ppm], it was not possible to significantly decrease the fungal attack (60% attack of the leaves).

Use Examples (pesticidal activity)

The active compounds were prepared as a 10% strength by weight emulsion in a mixture of 70% by weight of cyclohexanol, 20% by weight of Nekanil® LN*) and 10% by weight of Emulphor® EL**) and diluted with water according to the concentration desired. After

*) Lutensol® AP6=wetting agent having emulsifier and dispersant action based on ethoxylated alkylphenols **) Emulan®L=emulsifier based on ethoxylated fatty alcohols conclusion of the tests, the lowest concentration in each case was determined at which the compounds I still caused an 80–100% mortality in comparison with untreated control tests (action threshold or minimum concentration).

Use Example 3 (insecticidal action)

Activity against *Nephotettix cincticeps* (green rice leaf hopper); contact action Round filters (∅ 9 cm) treated with aqueous active compound preparations were infested with 5 adult leafhoppers. 24 hours later, the mortality was assessed as follows:
100%=no surviving leafhoppers;
80%=1 surviving leafhopper;
60%=2 surviving leafhoppers;
<60%=at least 3 surviving leafhoppers (=without action).

The activity threshold of the compounds Nos. 1.01, 1.02, 1.03, 1.04, 1.08, 1.09, 1.10, 1.11, 1.14, 1.15 and 1.16 was a maximum of 0.4 mg per round filter.

Use Example 4 (insecticidal contact action)

Activity against *Prodenia litura* (Egyptian cotton leafworm)

Filters (∅ about 9 cm) treated with aqueous active compound preparations were infested with 5 caterpillars. The first assessment was carried out after 4 hours. If at least one caterpillar was still living, a feed mixture of the following composition was added.

20 l of water;
800 g of agar-agar;
13 l of water;
1370 g of yeast powder (Engevita yeast);
5150 g of corn meal;
1300 g of wheat germ;
200 g of Wesson salt;
100 g of cellulose powder;
50 g of sorbic acid;
50 g of Nipagin;
10 g of vitamin mixture comprising
  30 g of vitamin B1,
  60 g of vitamin B2,
  30 g of vitamin B6,
  120 g of nicotinic acid/niacin,
  120 g of calcium D-pantothenate,
  30 g of folic acid and
  1,2 g of biotin;
50 ml of antibiotics (1% in alcohol);
180 g of ascorbic acid;
  1.5 l of water for rinsing in the vitamins and rinsing out the vessels.

The mortaility was determined finally after 24 hours.

The activity threshold (=4 caterpillars dead) of the compounds Nos. 1.02, 1.04 and 1.05 was a maximum of 0.4 mg per round filter.

Use Example 5 (acaricidal contact action)

Activity against *Tetranychus telarius* (two-spotted spider mite)

Potted dwarf beans which had formed the second pair of adult leaves and which were heavily infested with the spider mites were sprayed with the aqueous active compound preparations until dripping wet. To do this, the plants were sprayed from all sides on a turntable with about 30 ml of the spray mixture. After 5 days in a greenhouse the control success was determined in % by means of a microscope (binocular).

In this test the compounds Nos. 1.01 to 1.16 showed activity thresholds of a maximum of 400 ppm.

We claim:

1. A substituted phenoxymethylphenyl derivative of the formula I

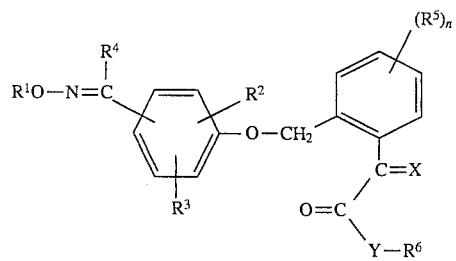

where the variables have the following meanings:

X is =CH—CH$_3$ OR =N—OCH$_3$;

R$^1$ is $C_1$–$C_6$-alkyl, $C_2$–$C_6$-alkenyl, $C_3$–$C_6$-alkynyl, $C_1$–$C_6$-haloalkyl, $C_3$–$C_6$-haloalkenyl, $C_1$–$C_4$-alkoxy-$C_1$–$C_6$-alkyl, cyano-$C_1$–$C_6$-alkyl, $C_1$–$C_6$-alkoxycarbonyl-$C_1$–$C_6$-alkyl, a $C_3$–$C_6$-cycloalkyl or $C_3$–$C_6$-cycloalkyl-$C_1$–$C_4$-alkyl group, phenyl-$C_1$–$C_6$-alkyl, naphthyl-$C_1$–$C_6$-alkyl, phenyl-$C_3$–$C_6$-alkenyl or phenoxy-$C_1$–$C_6$-alkyl group, a saturated or unsaturated 4- to 6-membered heterocyclyl or heterocyclyl-$C_1$–$C_4$-alkyl group or a heteroaryl-$C_1$–$C_6$-alkyl group, the heterocyclic rings in addition to C atoms in each case containing one or two ring members which are selected from the group consisting of an oxygen or sulfur atom and one or two nitrogen atoms and one or two groups —N(CH$_3$)—, it being possible for the cycloalkyl and heterocyclic rings in each case in turn to carry one or more radicals selected from the group consisting of: halogen, $C_1$–$C_4$-alkyl, $C_1$–$C_2$-haloalkyl, $C_3$–$C_6$-cycloalkyl, $C_1$–$C_4$-alkoxy, $C_1$–$C_2$-haloalkoxy, halogen, aryl and aryloxy;

R$^2$ and R$^3$ are hydrogen, halogen, cyano, nitro, $C_1$–$C_4$-alkyl, $C_1$–$C_2$-haloalkyl, $C_1$–$C_4$-alkoxy, $C_1$–$C_2$-haloalkoxy, or, if R$^2$ and R$^3$ are adjacent, together are an oxymethylidenoxy or oxyethylidenoxy bridge, it being possible for each C atom of these bridges if desired to carry one or two halogen atoms and/or methyl radicals;

R$^1$ is cyano, chlorine, bromine, $C_1$–$C_6$-alkoxy, $C_1$–$C_6$-alkylthio, $C_1$–$C_4$-haloalkoxy, $C_1$–$C_4$-alkoxy-$C_1$–$C_4$-alkoxy, $C_3$–$C_6$-cycloalkyl-$C_1$–$C_2$-alkoxy, $C_1$–$C_6$-alkylamino, di-($C_1$–$C_6$-alkyl)amino, $C_3$–$C_6$-alkenyloxy, $C_3$–$C_6$-alkynyloxy, aryloxy, arylthio, it being possible for the aromatic rings to carry one to three radicals selected from the group consisting of $C_1$–$C_4$-alkyl, $C_1$–$C_4$-alkoxy, $C_1$–$C_4$-haloalkyl, $C_1$–$C_4$-haloalkoxy and $C_1$–$C_4$-alkylthio, and it being possible for the aromatic rings additionally to carry sufficient halogen atoms such that the total number of radicals is 4 or 5;

R$^5$ is nitro, cyano, halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl or phenoxy, it being possible for the phenyl or phenoxy rings to carry one to three radicals selected from the group consisting of $C_1$–$C_4$-alkyl, $C_1$–$C_4$-haloalkyl, $C_1$–$C_4$-alkoxy, $C_1$–$C_4$-haloalkoxy and $C_1$–$C_4$-alkylthio, and it being possible for the phenyl or phenoxy rings additionally to carry sufficient halogen atoms such that the total number of radicals is 4 or 5;

or, if n is 2, 3, or 4, is a 1,3-butadiene-1,4-diyl group or a mono- or dihalogenated 1,3-butadiene-1,4-diyl group fused to two adjacent C atoms of the parent substance, it being possible for these fused rings in turn to carry one or two radicals selected from the group consisting of nitro, cyano, halogen, $C_1$–$C_4$-haloalkyl, $C_1$–$C_4$-alkoxy, $C_1$–$C_4$-haloalkoxy and $C_1$–$C_4$-alkylthio;

n is 0, 1, 2, 3 or 4, it being possible for the radicals R$^5$ to be identical or different if n is 2, 3 or 4;

Y is oxygen, —NH— or —N(CH$_3$)—;

R$^6$ is hydrogen or $C_1$–$C_4$-alkyl.

2. An α-methoxyiminophenylacetic acid methylamide of the formula XI'

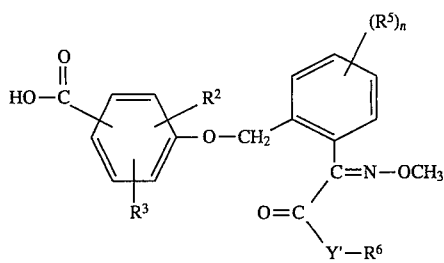

where the variables have the following meanings:

Y' is —NH— or —N(CH$_3$)—;

R$^2$ and R$^3$ independently of one another are hydrogen, halogen, cyano, nitro, C$_1$–C$_4$-alkyl, C$_1$–C$_2$-haloalkyl, C$_1$–C$_4$-alkoxy, C$_1$–C$_2$-haloalkoxy;

R$^5$ is nitro, cyano, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, phenyl or phenoxy, it being possible for the phenyl or phenoxy rings to carry one to three radicals selected from the group consisting of C$_1$–C$_4$-alkyl, C$_1$–C$_4$-haloalkyl, C$_1$–C$_4$-alkoxy, C$_1$–C$_4$-haloalkoxy and C$_1$–C$_4$-alkylthio, and it being possible for the phenyl or phenoxy rings additionally to carry sufficient halogen atoms such that the total number of radicals is 4 or 5;

or, if n is 2, 3, or 4, is a 1,3-butadiene-1,4-diyl group or a mono- or dichlorinated 1,3-butadiene-1,4-diyl group fused to two adjacent C atoms of the parent substance, it being possible for these fused rings in turn to carry one or two radicals selected from the group consisting of nitro, cyano, C$_1$–C$_4$-haloalkyl, C$_1$–C$_4$-alkoxy, C$_1$–C$_4$-haloalkoxy and C$_1$–C$_4$-alkylthio;

n is 0, 1, 2, 3 or 4, it being possible for the radicals R$^5$ to be identical or different if n is 1, 2, 3 or 4;

R$^6$ is hydrogen or C$_1$–C$_4$-alkyl.

3. A 2-(phenoxymethyl)phenylacetic acid derivative of the formula IVb'

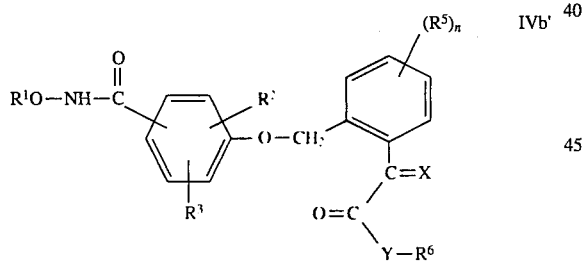

where the variables have the following meanings:

X is =CH—CH$_3$ or =N—OCH$_3$;

Y is oxygen, —NH— or —N(CH$_3$)—;

R$^1$ is

C$_1$–C$_6$-alkyl, C$_2$–C$_6$-alkenyl, C$_3$–C$_6$-alkynyl, C$_1$–C$_6$-haloalkyl, C$_3$–C$_6$-haloalkenyl, C$_1$–C$_4$-alkoxy-C$_1$–C$_6$-alkyl, cyano-C$_1$–C$_6$-alkyl, C$_1$–C$_6$-alkoxycarbonyl-C$_1$–C$_6$-alkyl, a C$_3$–C$_6$-cycloalkyl or C$_3$–C$_6$-cycloalkyl-C$_1$–C$_4$-alkyl group, an aryl-C$_1$–C$_6$-alkyl or aryl-C$_3$–C$_6$-alkenyl or aryloxy-C$_1$–C$_6$-alkyl group, a saturated or unsaturated 4- to 6-membered heterocyclyl or heterocyclyl-C$_1$–C$_4$-alkyl group or a heteroaryl-C$_1$–C$_6$-alkyl group, the heterocyclic rings in addition to C atoms in each case containing one or two ring members which are selected from the group consisting of an oxygen or sulfur atom and one or two nitrogen atoms and one or two groups —N(CH$_3$)—, it being possible for the cycloalkyl and heterocyclic rings in each case in turn to carry one or more radicals selected from the group consisting of: halogen, C$_1$–C$_4$-alkyl, C$_1$–C$_2$-haloalkyl, C$_3$–C$_6$-cycloalkyl, C$_1$–C$_4$-alkoxy, C$_1$–C$_2$-haloalkoxy, halogen, aryl and aryloxy;

R$^2$ and R$^3$ are hydrogen, halogen, cyano, nitro, C$_1$–C$_4$-alkyl, C$_1$–C$_2$-haloalkyl, C$_1$–C$_4$-alkoxy, C$_1$–C$_2$-haloalkoxy, or, if R$^2$ and R$^3$ are adjacent, together are an oxymethylidenoxy or oxyethylidenoxy bridge, each C atom of these bridges one or two halogen atoms and/or methyl radicals;

R$^5$ is nitro, cyano, halogen, C$_1$–C$_4$-alkyl, C$_1$–C$_4$-haloalkyl, C$_1$–C$_4$-alkoxy, C$_1$–C$_4$-haloalkoxy, C$_1$–C$_4$-alkylthio, phenyl or phenoxy, it being possible for the aromatic rings to carry one to three radicals selected from the group consisting of C$_1$–C$_4$-alkyl, C$_1$–C$_4$-haloalkyl, C$_1$–C$_4$-alkoxy, C$_1$–C$_4$-haloalkoxy and C$_1$–C$_4$-alkylthio, and it being possible for the aromatic rings additionally to carry sufficient halogen atoms such that the total number of radicals is 4 or 5;

or, if n is 2, 3, or 4, is a 1,3-butadiene-1,4-diyl group or a mono- or dihalogenated 1,3-butadiene-1,4-diyl group fused to two adjacent C atoms of the parent substance, it being possible for these fused rings in turn to carry one or two radicals selected from the group consisting of nitro, cyano, C$_1$–C$_4$-haloalkyl, C$_1$–C$_4$-alkoxy, C$_1$–C$_4$-haloalkoxy and C$_1$–C$_4$-alkylthio;

n is 0, 1, 2, 3 or 4, it being possible for the radicals R$^5$ to be identical or different if n is 1, 2, 3 or 4;

R$^6$ is hydrogen or C$_1$–C$_4$-alkyl.

4. A phenoxymethylphenyl derivative of the formula I as claimed in claim 1, where n is 0 or 1;

X is =CH—CH$_3$ or =N—OCH$_3$;

Y is oxygen or —NH—;

R$^1$ is C$_1$–C$_6$-alkyl, C$_2$–C$_6$-alkenyl, C$_3$–C$_6$-alkynyl, C$_1$–C$_6$-haloalkyl or C$_3$–C$_6$-haloalkenyl;

R$^2$ is cyano, chlorine, fluorine, methyl, trifluoromethyl or methoxy;

R$^3$ is hydrogen, cyano, chlorine, fluorine, methyl or methoxy;

R$^4$ is cyano, chlorine, bromine, C$_1$–C$_6$-alkoxy, C$_1$–C$_6$-alkylthio, C$_3$–C$_6$-alkenyloxy, aryloxy or arylthio, and R$^5$ is cyano, halogen, C$_1$–C$_6$-alkyl, C$_1$–C$_6$-haloalkyl, C$_1$–C$_6$-alkoxy or phenyl.

5. A phenoxymethylphenyl derivative of the formula I as claimed in claim 1, where n is 0 or 1;

X is =NO—CH$_3$;

Y is —NH—;

R$^1$ is C$_1$–C$_6$-alkyl, C$_2$–C$_6$-alkenyl, C$_3$–C$_6$-alkynyl, C$_1$–C$_6$-haloalkyl or C$_3$–C$_6$-haloalkenyl;

R$^2$ is cyano, chlorine, fluorine, methyl, trifluoromethyl or methoxy;

R$^3$ is hydrogen, cyano, chlorine, fluorine, methyl or methoxy;

R$^4$ is cyano, chlorine, bromine, C$_1$–C$_6$-alkoxy, C$_1$–C$_6$-alkylthio, C$_3$–C$_6$-alkenyloxy, phenyloxy or phenylthio; and R$^5$ is cyano, chlorine, fluorine, methyl, trifluoromethyl; methoxy or phenyl.

6. A fungicidal composition containing solid and/or liquid carriers and a fungicidally active amount of at least one substituted phenoxymethylphenyl derivative of the formula I as defined in claim 1.

7. A method for controlling fungi, which comprises treating the fungi or the materials, plants, seeds or the soil threatened by fungal attack with a fungicidally active amount of at least one substituted phenoxymethylphenyl derivative of the formula I as defined in claim 1.

8. A composition for controlling pests, containing inert additives and a pesticidally active amount of at least one substituted phenoxymethylphenyl derivative of the formula I as defined in claim 1.

9. A method for controlling pests, which comprises treating the pests and/or their habitat with a pesticidally active amount of at least one substituted phenoxymethylphenyl derivative of the formula I as defined in claim 1.

10. A phenoxymethylphenyl compound of the formula I as defined in claim 1, wherein $R^1$ is $C_1$–$C_6$-alkyl, alkenyl, $C_3$–$C_6$-alkynyl, $C_1$–$C_6$-haloalkyl or $C_3$–$C_6$-haloalkenyl.

11. A phenoxymethylphenyl compound of the formula I as defined in claim 1, wherein X is $NOCH_3$, $YR^6$ is $NHCH_3$, $R^2$ is 2-Cl, $R^3$ is H, $R^4$ is $OCH_3$ and $R^1$ is $CH_3$.

12. A phenoxymethylphenyl compound of the formula I as defined in claim 1, wherein X is $NOCH_3$, $YR^6$ is $NHCH_3$, $R^2$ is 2-$CH_3$, $R^3$ is 5-$CH_3$, $R^4$ is $SCH_3$ and $R^1$ is $CH_3$.

13. A phenoxymethylphenyl compound of the formula I as defined in claim 1, wherein X is $NOCH_3$, $YR^6$ is $NHCH_3$, $R^2$ is 2-$CH_3$, $R^3$ is 5-$CH_3$, $R^4$ is Cl and $R^1$ is $CH_2CH_3$.

14. A phenoxymethylphenyl compound of the formula I as defined in claim 1, wherein X is $NOCH_3$, $YR^6$ is $NHCH_3$, $R^2$ is 2-$CH_3$ $R^3$ is 5-$CH_3$, $R^4$ is $SCH_3$ and $R^1$ is $CH_2CH_3$.

15. A phenoxymethylphenyl compound of the formula I as defined in claim 1, wherein X is $NOCH_3$, $YR^6$ is $NHCH_3$, $R^2$ is 2-$CH_3$ $R^3$, is 5-$CH_3$, $R^4$ is $SCH_3$ and $R^1$ is $CH(CH_3)_2$.

16. A phenoxymethylphenyl compound of the formula I as defined in claim 1, wherein X is $NOCH_3$, $YR^6$ is $NHCH_3$, $R^2$ is 2-$CH_3$, $R^3$ is 5-$CH_3$, $R^4$ is Cl and $R^1$ is $CH_2CH=CH_2$.

17. A phenoxymethylphenyl compound of the formula I as defined in claim 1, wherein X is $NOCH_3$, $YR^6$ is $NHCH_3$, $R^2$ is 2-$CH_3$, $R^3$ is 5-$CH_3$, $R^4$ is $SCH_3$ and $R^1$ is $CH_2CH=CH_2$.

18. A phenoxymethylphenyl compound of the formula I as defined in claim 1, wherein X is $NOCH_3$, $YR^6$ is $NHCH_3$, $R^2$ is 2-$CH_3$, $R^3$ is 5-$CH_3$, $R^4$ is $OCH_2CH_3$ and $R^1$ is $CH_2CH_3$.

19. A phenoxymethylphenyl compound of the formula I as defined in claim 1, wherein X is $CHCH_3$, $YR^6$ is $OCH_3$, $R^2$ is 2-$CH_3$, $R^3$ is 5-$CH_3$, $R^4$ is $OCH_3$ and $R^1$ is $CH_2CH_3$.

20. A phenoxymethylphenyl compound of the formula I as defined in claim 1, wherein X is $CHCH_3$, $YR^6$ is $OCH_3$, $R^2$ is 2-$CH_3$, $R^3$ is 5-$CH_3$, $R^4$ is Cl and $R^1$ is $CH_3$.

* * * * *

UNITED STATES PATENT AND TRADEMARK OFFICE
CERTIFICATE OF CORRECTION

PATENT NO.: 5,545,664

DATED: August 13, 1996

INVENTOR(S): KIRSTGEN et al.

It is certified that error appears in the above-identified patent and that said Letters Patent is hereby corrected as shown below:

On the cover page, item [57], line 1 after the formula, "=C—CH$_3$" should be -- =CH—CH$_3$ --.

Column 93, claim 1, line 60, "X is =CH—CH$_3$ OR =N-OCH$_3$;" should read --X is =CH—CH$_3$ or =N-OCH$_3$;--.

Column 94, claim 1, line 26, "R$^1$" should be --R$^4$--.

Column 96, claim 3, line 11, after "bridges" insert --optionally carrying--.

Signed and Sealed this

Nineteenth Day of November, 1996

Attest:

BRUCE LEHMAN

Attesting Officer

Commissioner of Patents and Trademarks